(12) United States Patent
Godowski et al.

(10) Patent No.: US 6,287,784 B1
(45) Date of Patent: *Sep. 11, 2001

(54) KINASE RECEPTOR ACTIVATION ASSAY

(75) Inventors: Paul J. Godowski; Melanie R. Mark, both of Burlingame; Michael Daniel Sadick, El Cerrito; Wai Lee Tan Wong, Los Altos Hills, all of CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/417,381

(22) Filed: Oct. 13, 1999

Related U.S. Application Data

(63) Continuation of application No. 08/374,565, filed as application No. PCT/US94/13329 on Nov. 18, 1994, now Pat. No. 6,025,145, which is a continuation-in-part of application No. 08/157,563, filed on Nov. 23, 1993, now abandoned, which is a continuation-in-part of application No. 08/170,558, filed on Dec. 20, 1993, now Pat. No. 6,001,621, and a continuation-in-part of application No. 08/286,305, filed on Aug. 5, 1995, now Pat. No. 5,766,863.

(51) Int. Cl.$^7$ ......................... G01N 33/53; G01N 33/566; C12Q 1/48; C12N 15/12; C12N 9/12
(52) U.S. Cl. ............................. 435/7.1; 435/7.2; 435/15; 435/69.1; 435/194; 435/325
(58) Field of Search ............................. 435/7.2, 15, 67.1, 435/194, 325, 7.1

(56) References Cited

U.S. PATENT DOCUMENTS 6,025,145 * 2/2000 Godowski et al. .................... 435/7.2

FOREIGN PATENT DOCUMENTS

| 244221 | 4/1987 | (EP) . |
|---|---|---|
| 88/04692 | 6/1988 | (WO) . |
| 93/15201 | 5/1993 | (WO) . |
| 94/19463 | 1/1994 | (WO) . |

OTHER PUBLICATIONS

Cleaveland et al., "A Microtiter–Based Assay for the Detection of Protein Tyrosine Kinase Activity," *Analytical Biochemistry*, 190:249–253 (1990).
Corfas et al., "ARIA, a Protein that Stimulates Acetylcholine Receptor Synthesis, also Induces Tyrosine Phosphorylation of a 185–kDa Muscle Transmembrane Protein," *PNAS, USA*, 90:1624–1628 (Feb. 1993).
Dijke et al., "Serine/Threonine Kinase Receptors," *Progress in Growth Factor Research*, 5:55–72 (1994).
Donato et al., "Tumor Necrosis Factor Regulates Tyrosine Phosphorylation on Epidermal Growth Factor Receptors in A431 Carcinoma Calls: Evidence for a Distinct Mechanism," *Cell Growth and Differentiation*, 3:259–268 (1992).
Fantl et al., "Signalling by Receptor Tyrosine Kinases," *Annual Review in Biochemistry*, 62:453–481 (1993).
Fujimoto, "brt, A Mouse Gene Encoding a Novel Receptor–Type Protein–Tyrosine Kinase, is Preferentially Expressed in the Brain," *Oncogene*, 9:693:698 (1994).
GenBank, "Release 79" (along with hstyro3 and hstyro3y sequences available on GenBank) (Oct. 15, 1993).
Glenney et al., "Monoclonal Antibodies to Phosphotyrosine," *Journal of Immunological Methods* 109:277–285 (1988).
Hagino et al., "Enzyme–Linked Immunosorbent Assay Method for Human Autophosphorylated Insulin Receptor," *Diabetes*, 43:274–280 (Feb. 1994).
Holmes et al., "Identification of Heregulin, a Specific Activator of $p185^{erbB2}$," *Science*, 256:1205–1210 (1992).
Hunter, "Protein Kinase Classification," *Methods in Enzymology*, 200:3–37 (1991).
Hunter, "Synthetic Peptide Substrates for a Tyrosine Protein Kinase," *Journal of Biological Chemistry*, 257(9):4843–4848 (1982).
Hunter et al., "Protein–Tyrosine Kinases," *Annual Review in Biochemistry*, 54:897–930 (1985).

(List continued on next page.)

*Primary Examiner*—Prema Mertz
(74) *Attorney, Agent, or Firm*—David A. Carpenter

(57) ABSTRACT

An assay for measuring activation (i.e., autophosphorylation) of a tyrosine kinase receptor of interest is disclosed.

(a) A first solid phase is coated with a substantially homogeneous population of cells so that the cells adhere to the first solid phase. The cells have either an endogenous tyrosine kinase receptor or have been transformed with DNA encoding a receptor or "receptor construct" and the DNA has been expressed so that the receptor or receptor construct is presented in the cell membranes of the cells.

(b) A ligand is then added to the solid phase having the adhering cells, such that the tyrosine kinase receptor is exposed to the ligand.

(c) Following exposure to the ligand, the adherent cells are solubilized, thereby releasing cell lysate.

(d) A second solid phase is coated with a capture agent which binds specifically to the tyrosine kinase receptor, or, in the case of a receptor construct, to the flag polypeptide.

(e) The cell lysate obtained in step (c) is added to the wells containing the adhering capture agent so as to capture the receptor or receptor construct to the wells.

(f) A washing step is then carried out, so as to remove unbound cell lysate, leaving the captured receptor or receptor construct.

(g) The captured receptor or receptor construct is exposed to a labelled anti-phosphotyrosine antibody which identifies phosphorylated residues in the tyrosine kinase receptor.

(h) Binding of the anti-phosphotyrosine antibody to the captured receptor or receptor construct is measured.

23 Claims, 71 Drawing Sheets

OTHER PUBLICATIONS

Kamps, "Generation and Use of Anti–Phosphotyrosine Antibodies for Immunoblotting," *Methods in Enzymology*, 201:101–110 (1991).

Kasuga et al., "Insulin Stimulation of Phosphorylation of the β Subunit of the Insulin Receptor," *Journal of Biological Chemistry*, 257 (17):9891–9894 (1982).

Kasuga et al., "Phosphorylation of the Insulin Receptor in Cultured Hepatoma Cells and a Solubilized System," *Methods in Enzymology*, 109:609–621 (1985).

King et al., "High Throughput Assay for Inhibitors of the Epidermal Growth Factor Receptor–Associated Tyrosine Kinase" *Life Sciences*, 53:1465–1472 (1993).

Klein et al, "A Microtiter Well Assay System to Measure Insulin Activation of Insulin Receptor Kinase in Intact Human Mononuclear Cells," *Diabetes*, 42:883–890 (Jun. 1993).

Knutson et al., "Comparison of Insulin Receptor Tyrosine Phosphorylation Under in vitro and in situ Conditions: Assessment of Specific Protein Tyrosine Phosphorylation with the Use of $^{32}$P–phosphate–labeled substrates," *Archives of Biochemistry & Biophysics*, 285(2):197–204 (1991).

Kozma et al., "Comparison of Three Methods for Detecting Tyrosine–Phosphorylated Proteins," *Methods in Enzymology*, 201:28–43 (1991).

Lai et al., "An Extended Family of Protein–Tyrosine Kinase Genes Differentially Expressed in the Vertebrate Nervous System" *Neuron*, 6:691–704 (May 1991).

Lai et al., "Structure, Expression, and Activity of Tyro 3, a Neural Adhesion–Related Receptor Tyrosine Kinase," *Oncogene* 9:2567–2578 (1994).

Lazaro et al., "Description of an Enzyme–Linked Immunosorbent Assay for the Detection of Protein Tyrosine Kinase," *Analytical Biochemistry*, 192:257–261 (1991).

MacDonald et al., "Reconstitution of the Raf–1–MEK–ERK signal Transduction Pathway in vitro." *Molecular and Cellular Biology*, 13:6615–6620.

Madden et al., "Two Nonradioactive Assays for Phosphotyrosine Phosphatases with Activity toward the Insulin Receptor," *Analytical Biochemistry*, 199:210–215 (1991).

Mark et al., "rse, a Novel Receptor–Type Tyrosine Kinase with Homology to Axl/Ufo, is Expressed at High Levels in the Brain," *Journal of Biological Chemistry*, 269(14):10720–10728 (Apr. 8, 1994).

Mathews, "Activin Receptors and Cellular Signaling by the Receptor Serine Kinase Family" *Endocrine Review*, 15(3):310–325 (1994).

Meloche, et al., "Functional Expression and Growth Factor Activation of an Epitope–Tagged p44 Mitogen–Activated Protein Kinase, P44$^{mapk}$," *Molecular Biology of the Cell*, 3:63–71 (1992).

O'Bryan et al., "axl, a Transforming Gene Isolated from Primary Human Myeloid Leukemia Cells, Encodes a Novel Receptor Tyrosine Kinase," *Molecular & Cellular Biology*, 11:5016–5031 (1991).

Ohashi et al., "Cloning of the cDNA for a Novel Receptor Tyrosine Kinase, Sky, Predominantly Expressed in Brain," *Oncogene* 9:699–705 (1994).

Paborsky, et al., "Mammalian Cell Transient Expression of Tissue Factor for the Production of Antigen," *Protein Engineering*, 3(6):547–553 (1990).

Park et al., "Sequence of MET Protooncogene cDNA has Features Characteristic of the Tyrosine Kinase Family of Growth–Factor Receptors," *PNAS, USA*, 84:6379–6383 (1987).

Pazin et al., "Triggering Signaling Cascades by Receptor Tyrosine Kinases," *TIBS*, 17:374–378 (1992).

Pike, "Assay of Growth Factor–Stimulated Tyrosine Kinases Using Synthetic Peptide Substrates," *Methods of Enzymology*, 146:353–362 (1987).

Polvi et al., "The Human Tyro3 Gene and Pseudogene are Located in Chromosome 15q14–q25" *Gene*, 134:289–293 (1993).

Sale, "Serine/Threonine Kinases and Tyrosine Phosphatases that Act on the Insulin Receptor," *Biochemical Society Transacations*, 20:664–670 (1992).

Stark et al., "FGFR–4, a new member of the fibroblast growth factor receptor family, expressed in the definitive endoderm and skeletal muscle lineages of the mouse," *Development*, 113:641–651 (1991).

Ullrich and Schlessinger, "Signal Transduction by Receptors with Tyrosine Kinase Activity," *Cell*, 61:203–212 (Apr. 1990).

Wang, "Isolation of Antibodies for Phosphotyrosine by Immunization with a v–abl Oncogene–Encoded Protein," *Molecular & Cellular Biology*, 5(12):3640–3643 (1985).

Wang et al., "Evidence for Association of the Cloned Liver Growth Hormone Receptor with a Tyrosine Kinase," *Journal of Biological Chemistry*, 267(24):17390–17396 (1992).

White et al. "Preparation and Use of Anti–Phosphotyrosine Antibodies to Study Structure and Function of Insulin Receptor," *Methods in Enzymology*, 201:65–79 (1991).

Wilks et al., "The Application of the Polymerase Chain Reaction to Cloning Members of the Protein Tyrosine Kinase Family," *Gene*, 85:67–74 (1989).

* cited by examiner

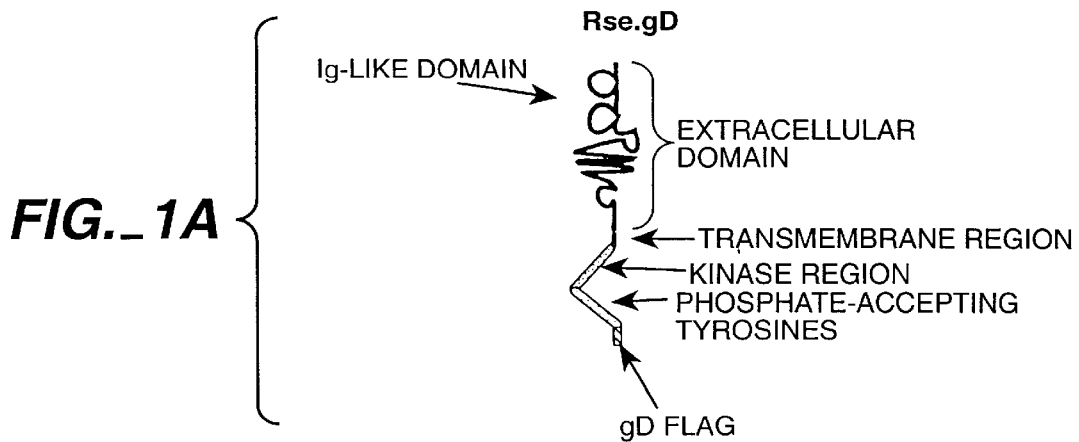
FIG._1A
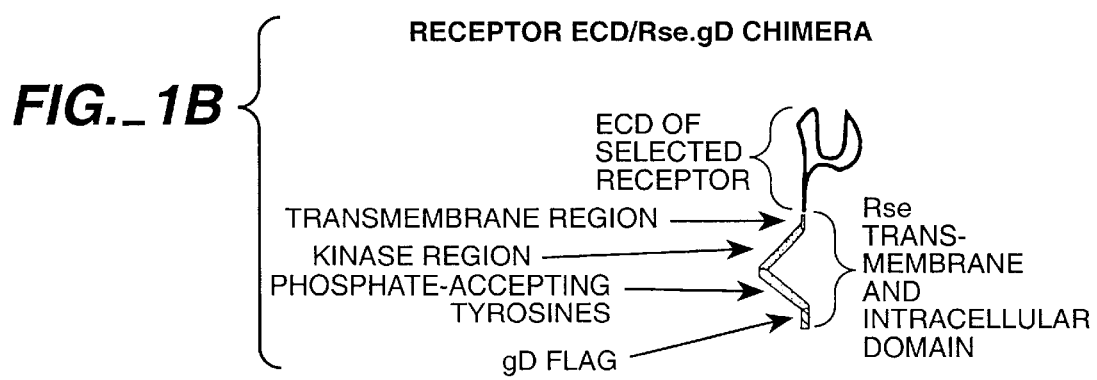
FIG._1B
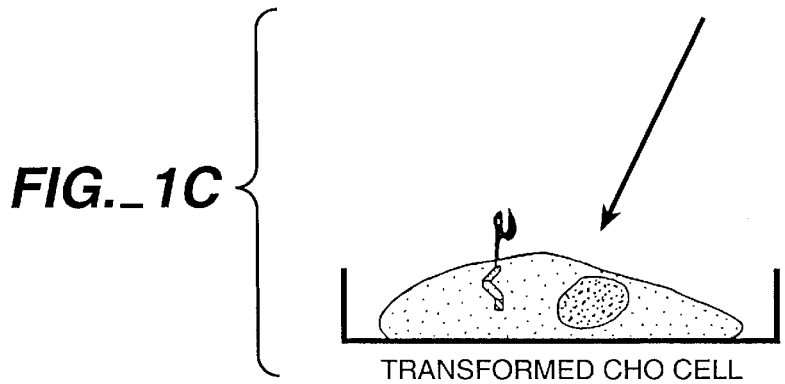
FIG._1C

FIG._2A signal sequence
```
       *    *    *    *    *    *    *    *    *    *    *    *    *    *    *    *    *
       M    A    L    R    R    S    M    G    R    P    G    L    P    P    P    P    R    L    G    L    P    L    P    P    P    R    L    G    L    L    L    A    A    L    A    S    L    L
    1  ATGGGGCTGA GCGGAGCAT GGGGCGGCCG GGGCTCCCCG CCTGCCGCT CCGGGCTCG GCTGCTGCT GCCGGCTCTG GCTTCTCTGC
       *    *    *    *
       L    P    E    S    A    A                     extracellular domain
       A    G    L    K    L    M    G
   35  TGCTCCCCGA GTCCGCCGCC GCAGGTCTGA AGCTCATGGG
       G    M    E    E    P    D    I    Q    W    V    K    D    G    A    V    V    Q    K    L    T    V    S    Q    G    Q    P    V    K    L    N    C    S    V    E
   68  GGGGATGGAG GAGCCTGACA TCCAGTGGGT GAAGGATGGG GCAGTGGTCC AGAAACTTGGA GTGTCTCAGGG GCAGCCGGTG AAGCTCAACT GCAGTGTGGA
       F    L    S    L    K    S    V    E    R    S    D    A    G    R    Y    W    C    Q    V    E    D    G    G    E    T    E    I    S    Q    P    V    W    L    T
  101  TTCCTCAGCC TGAAGTCAGT GGAGCGCTCT GACGCCGGCC GGTACTGGTG CCAGGTGGTG GATGGGGGTG AAACCGAGAT CTCCCAGCCA GTGTGGCTCA
       V    E    G    V    P    F    F    T    V    E    P    K    D    L·A    V    P    P    N    A    P    F    Q    L    S    C    E    A    V    G    P    P    E
  135  CGGTAGAAGG TGTGCCATTT TTCACAGTGG AGCCAAAAGA TCTGGCAGTG CCACCCAATG CCCCTTTCCA ACTGTCTTGT GAGGCTGTGG GTCCCCCTGA
       P    V    T    I    V    W    W    R    G    T    T    K    I    G    G    P    A    P    S    P    S    V    L    N    V    T    G    V    T    Q    S    T    M
  168  ACCTGTTACC ATTGTCTGGT GGAGAGGAAC TACGAAGATC GGGGGACCCG CTCCCTCTCC ATCTGTTTTA AATGTAACAG GGGTGACCA GAGCACCATG
       F    S    C    E    A    H    N    L    K    G    L    A    S    S    R    T    A    T    V    H    L    Q    A    L    P    A    A    P    F    N    I    T    V    T
  201  TTTTCCTGTG AAGCTCACAA CCTAAAAGGC CTGGCCTCTT CTCGCACAGC CACTGTTCAC CTTCAAGCAC TGCCTGCAGC CCCCTTCAAC ATCACCGTGA
       K    L    S    S    N    A    S    V    A    W    M    P    G    A    D    G    R    A    L    L    Q    S    C    T    V    Q    V    T    Q    A    P    G
  235  CAAAGCTTTC CAGCAGCAAC GCTAGTGTGG CCTGGATGCC AGGTGCTGAT GGCCGAGCTC TGCTACAGTC CTGTACAGTT CAGTGACAC AGGCCCCAGG
       G    W    E    V    L    A    V    V    V    P    V    P    P    F    T    C    L    R    D    L    V    P    A    T    N    Y    S    L    R    V    R    C
  268  AGGCTGGGAA GTCCTGGCTG TTGTGGGCCC TGTGCCCCCC CCTTTACCTGC TGCTCCGGGA CCTGGTGCCT GCCACCAACT ACAGCCTCAG GGTGCGCTGT
       A    N    A    L    G    P    S    P    Y    A    D    W    V    P    F    Q    T    K    G    L    A    P    A    S    A    P    Q    N    L    H    A    I    R    T
  301  GCCAATGCCT TGGGGCCCTC TCCCTATGCT GACTGGGTGC CCTTTCAGAC CAAGGGTCTA GCCCCAGCCA GCGCTCCCCA AAACCTCCAT GCCATCCGCA
       D    S    G    L    I    L    E    W    E    E    V    I    P    E    A    P    L    E    G    P    L    G    P    Y    K    L    S    W    V    Q    D    N    G
  335  CAGATTCAGG CCTCATCTTG GAGTGGGAAG AAGTGATCCC CGAGGCCCCT TTGGAAGGCC CCCTGGGACC CTACAAACTG TCCTGGGTTC AAGACAATGG
```

FIG._2B

```
368   T  Q  D   E  L  T  V   E  G  T   R  A  N   L  T  G  W   D  P  Q   K  D  L   I  V  R  V   C  V  S   N  A  V
1101  AACCCAGGAT GAGCTGACAG TGGAGGGGAC CAGGGCCAAT TTGACAGGCT GGGATCCCCA AAAGGACCTG ATCGTAGTG TGTGCGTCTC CAATGCAGTT
                                                                                                    transmembrane domain
401   G  C  G  P   W  S  Q   P  L  V   V  S  S  H   D  R  A   G  Q  Q   G  P  P  H   S  R  T   S  W  V  P  V  V  L
1201  GGCTGTGGAC CCTGGAGTCA GCCACTGGTG GTCTCTTCTC ATGACCGTGC AGGCCAGCAG GGCCCTCCTC ACAGCCCGAC ATCCTGGGTA CCTGTGGTCC 435   G  V  L   T  A  L   V  T  A  A   A  L  A   L  I  L   L   R  K  R   R  K  E   T  R  F   G  Q  A  F   D  S  V
1301  TTGGTGTGCT AACGGCCCTG GTGACGGCTG CTGCCCTGGC CCTCATCCTG CTTCGAAAGA GACGGAAAGA GACGCGGTTT GGGCAAGCCT TTGACAGTGT
                                                intracellular domain 468   M  A  R   G  E  P  A   V  H  F   R  A  A   R  S  F  N   R  E  R   P  E  R   I  E  A  T   L  D  S   L  G  I
1401  CATGGCCCGG GGAGAGCCAG CCGTTCACTT CCGGGCAGCC CGGTCCTTCA ATCGAGAAAG GCCCGAGCGC ATCGAGGCCA CATTGGACAG CTTGGGCATC 501   S  D  E  L   K  E  K   L  E  D   V  L  I  P   E  Q  Q   F  T  L   G  R  M  L   G  K  G   E  F  G   S  V  R  E
1501  AGCGATGAAC TAAAGGAAAA ACTGGAGGAT GTGCTCATCC CAGAGCAGCA GTTCACCCTG GGCCGGATGT TGGGCAAAGG AGAGTTTGGT TCAGTGCGGG 535   A  Q  L   K  Q  E   D  G  S  F   V  K  V   A  V  K   M  L  K  A   D  I  I   A  S  S   R  A  K  G   R  L  P   I  P  M
1601  AGGCCCAGCT GAAGCAAGAG GATGGCTCCT TTGTGAAAGT GGCTGTGAAG ATGCTGAAAG CTGACATCAT TGCCTCAAGC AGGGCTAAAG GCCGTCTCCC CATCCCCATG 568   E  A  A   C  M  K  E   F  D  H   P  H  V   A  K  L  V   G  V  S   L  R  S   G  E  N  P   F  N  L   P  L  Q   T  L  I  R
1701  GAAGCAGCT TGCATGAAGG AGTTTGACCA TCCACACGTG GCCAAACTTG TTGGGGTAAG CCTCCGCTCG GGGAGAACC CCTTTAACCT ACCCCTCCAG ACCCTGATCC 601   V  I  L  P   F  M  K   H  G  D   L  H  A  F   L  L  A   S  R  N   F  I  H  R   D  L  A   A  R  N   C  M  L  A   E  D  M
1801  GTCATCTTGC CCTTCATGAA GCATGGGGAC CTGCATGCCT TCCTGCTCGC CTCTCGGAAC TTCATCCACC GAGACCTGGC TGCTCGGAAT TGCATGCTGG CAGAGGACAT 635   F  M  V   D  I  A   C  G  M  E   Y  L  S   S  R  N   F  I  H  R   Y  Y  R   Q  G  C   A  S  K  L   P  V  K   W  L  A
1901  GTTCATGGTT GGACATTGCC TGCGGCATGG AGTACCTGAG CTCTCGGAAC TTCATCCACC GAGACCTGGC TGCTCGGAAT TGCATGCTGG CAGAGGACAT 668   T  V  C   V  A  D  F   G  L  S   R  K  I   Y  S  G  D   Y  Y  R   Q  G  C   A  S  K  L   P  V  K   W  L  A
2001  GACAGTGTGT GTGGCTGACT TCGGACTCTC CCGGAAGATC TACAGTGGGG ACTACTATCG TCAAGGCTGT GCCTCCAAAC TGCCCGTCAA GTGGCTGGCC
```

FIG._2C

```
701 L  E  S  L    A  D  N    L  Y  T    V  Q  S  D    V  W  A    F  G  V    T  M  W  E    I  M  T    R  G  Q    T  P  Y  A
2101 CTGGAGAGCC TGGCCGACAA CCTGTATACT GTGCAGAGTG ACGTGTGGGC GTTCGGGGTG ACCATGTGGG AGATCATGAC ACGTGGGCAG ACGCCATATG

735  G  I  E    N  A  E    I  Y  N  Y    L  I  G    G  N  R    L  K  Q  P    P  E  C    M  E  D    V  Y  D  L    M  Y  Q
2201 CTGGCATCGA AAACGCTGAG ATTTACAACT ACCTCATTGG CGGGAACCGC CTGAAACAGC CTCCGGAGTG TATGGAGGAC GTGTATGATC TCATGTACCA

768  C  W  S    A  D  P  K    Q  R  P    S  F  T    C  L  R  M    E  L  E    N  I  L    G  Q  L  S    V  L  S    A  S  Q
2301 GTGCTGGAGT GCTGACCCCA AGCAGGCGCC GAGCTTTACT TGTCTGCGAA TGGAACTGGA GAACATCTTG GGCCAGCTGT CTGTGCTATC TGCCAGCCAG

801  D  P  L  Y    I  N  I    E  R  A    E  E  P  T    A  G  G    S  L  E    L  P  G  R    D  Q  P    Y  S  G    A  G  D  G
2401 GACCCCTTAT ACATCAACAT CGAGAGAGCT GAGGAGCCCA CTGCGGGGAG CTACCTGGAG CAGCCTGGCA GGGATCAGCC CTACAGTGGG GCTGGGGATG

835  S  G  M    G  A  V    G  G  T  P    S  D  C    R  Y  I    L  T  P  G    G  L  A    E  Q  P    G  Q  A  E    H  Q  P
2501 GCAGTGGCAT GGGGGCAGTG GGTGGCACTC CCAGTGACTG TCGGTACATA CTCACCCCCG GAGGGCTGGC TGAGCAGCCA GGGCAGGCAG AGCACCAGCC

868  E  S  P    L  N  E  T    Q  R  L    L  L  L    Q  Q  G  L    P  H  S  S  C    L  P  H    S  S  C    gD flag polypeptide
                                                                                                         A  D  A  S    L  K  M    A  D  P
2601 AGAGAGTCCC CTCAATGAGA CACAGAGGCT TTTGCTGCTG CAGCAAGGGC TACTGCCACA CTCGAGCTGC GCAGATGCTA GCCTCAAGAT GGCTGATCCA 901  N  R  F    R  G  K  D    L  P  V    L  Q
2701 AATCGATTCC GCGGCAAAGA TCTTCCGGTC CTGTAGAAGC TT
```

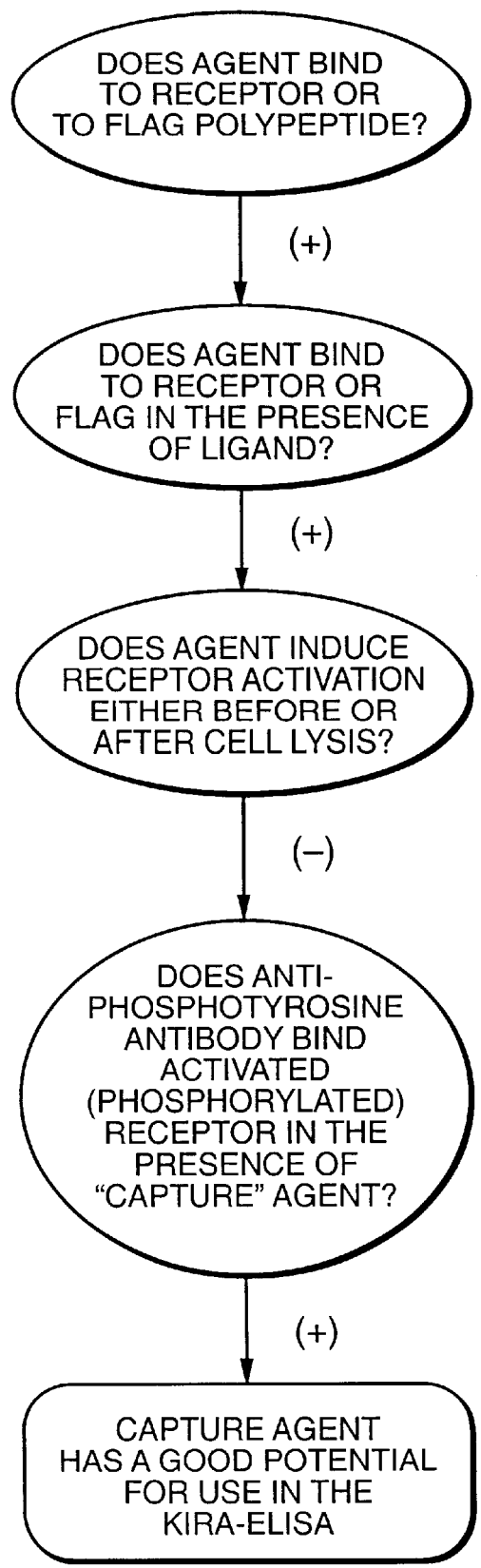
FIG._3

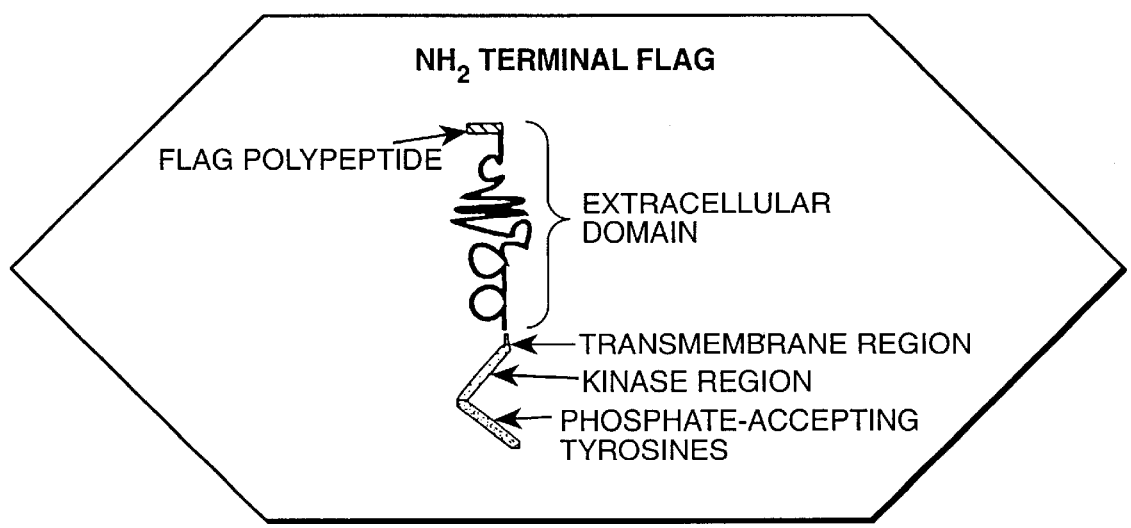
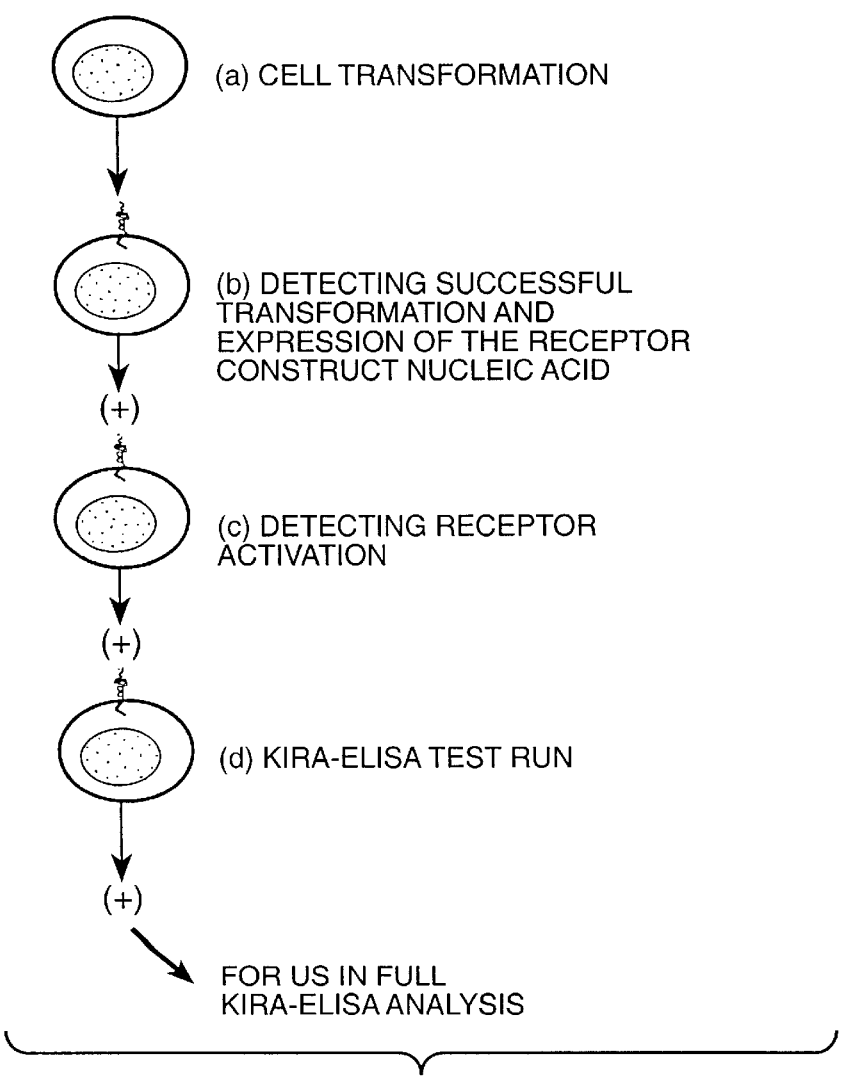
FIG._4

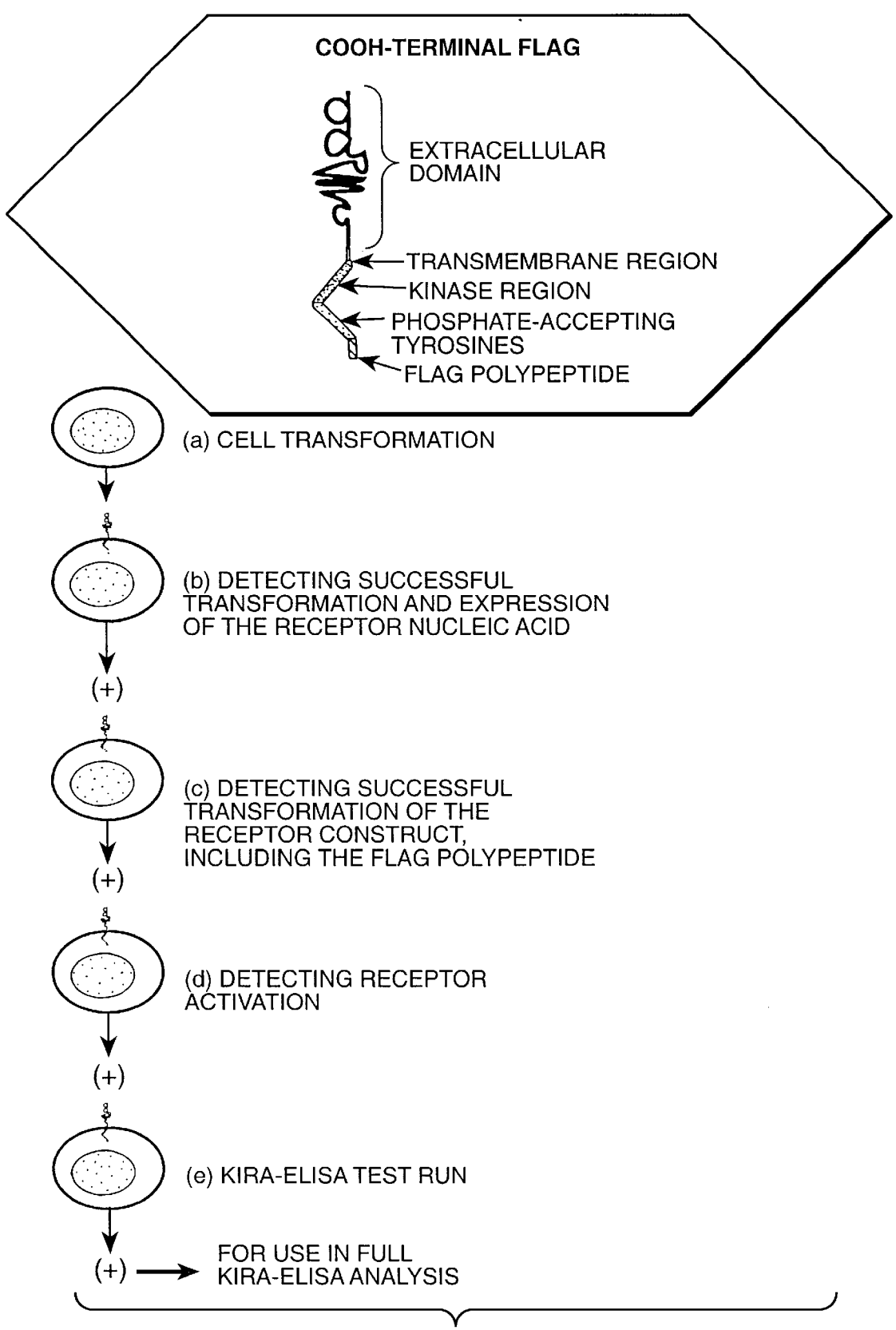
FIG._5

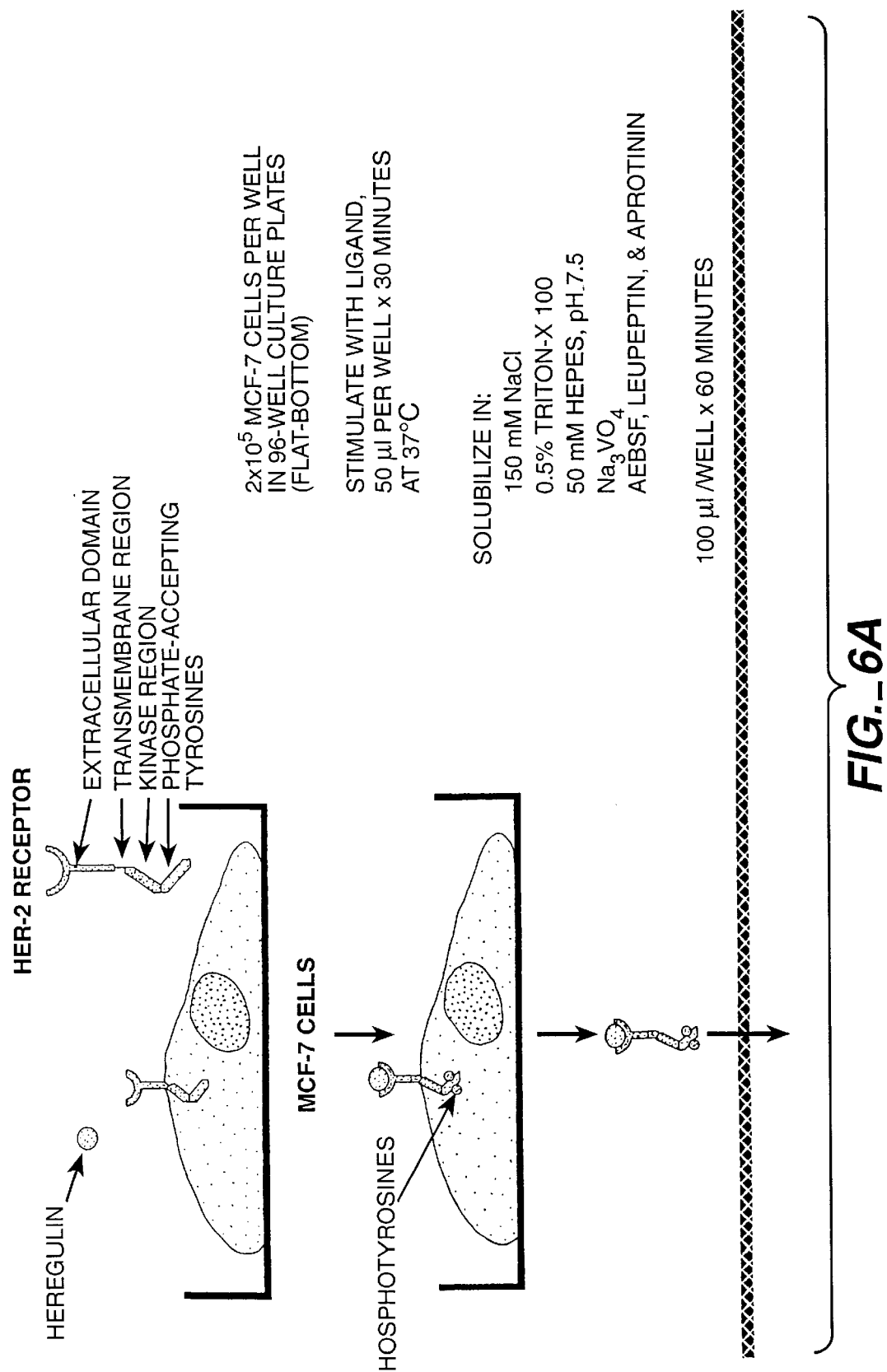
FIG._6A

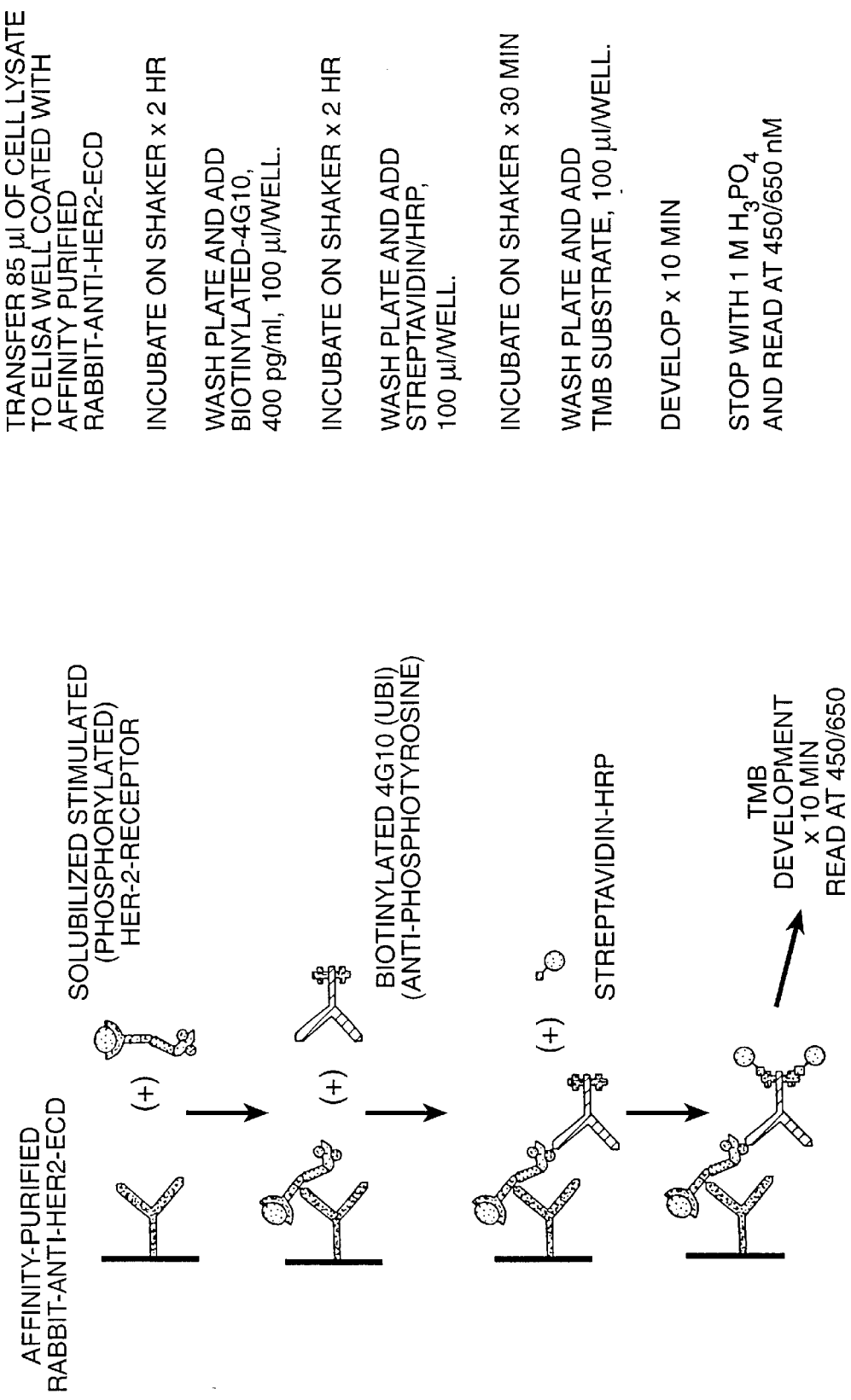
FIG._6B

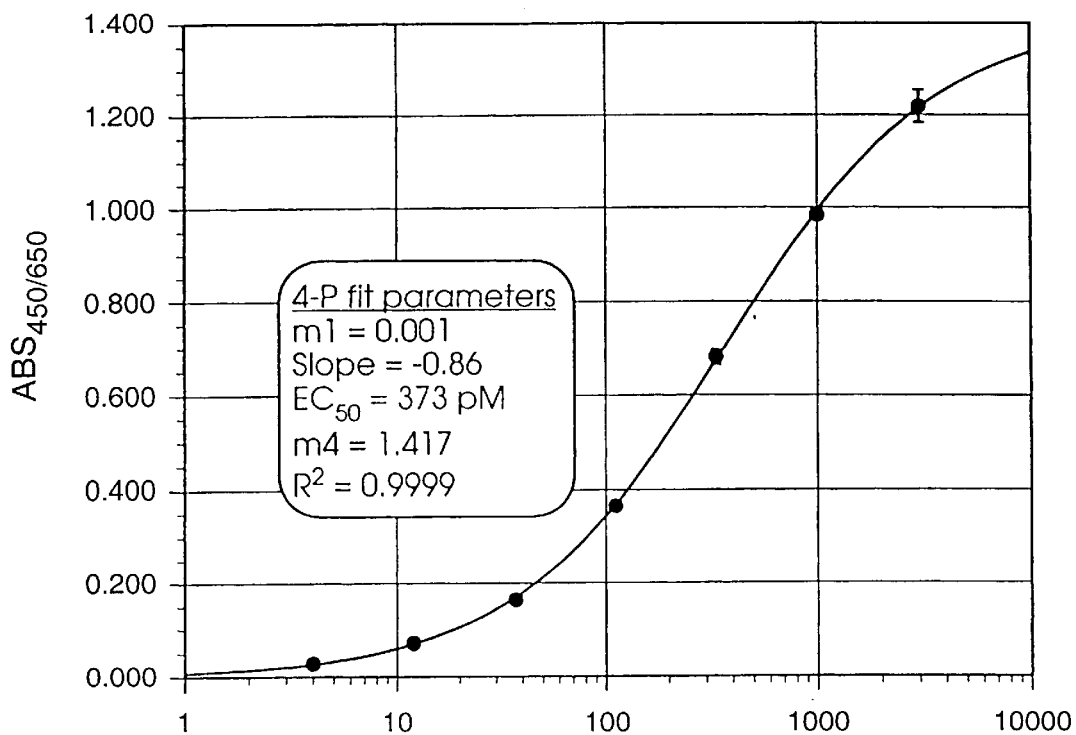
FIG._7
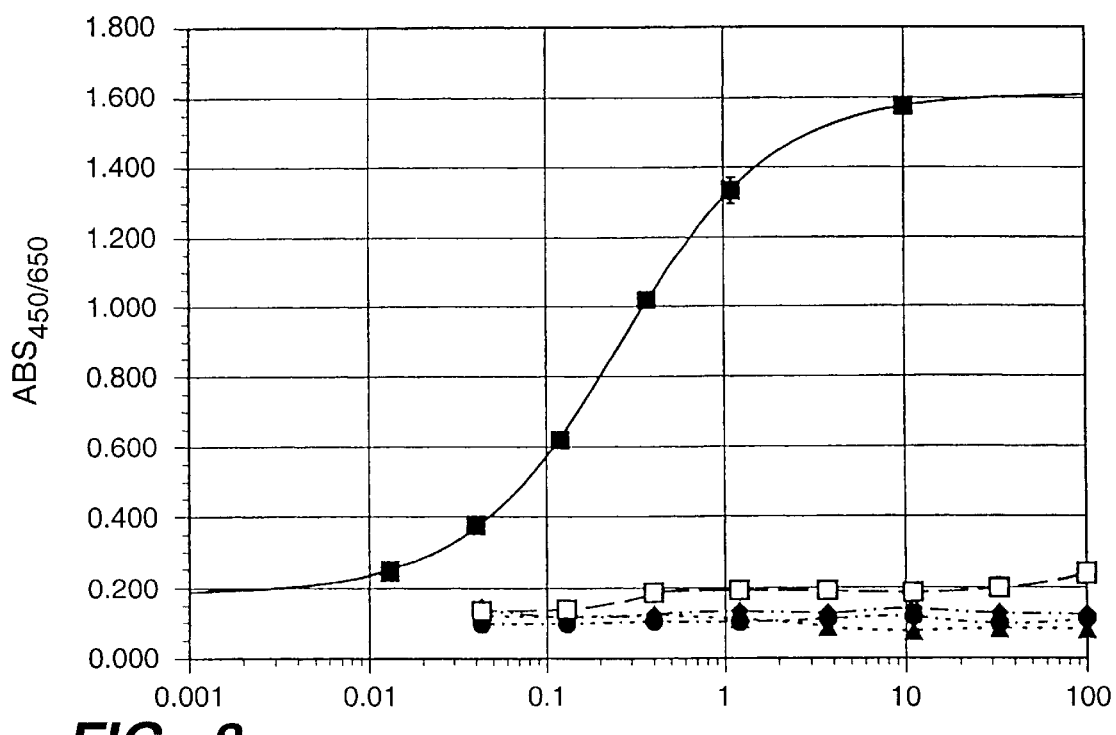
FIG._8

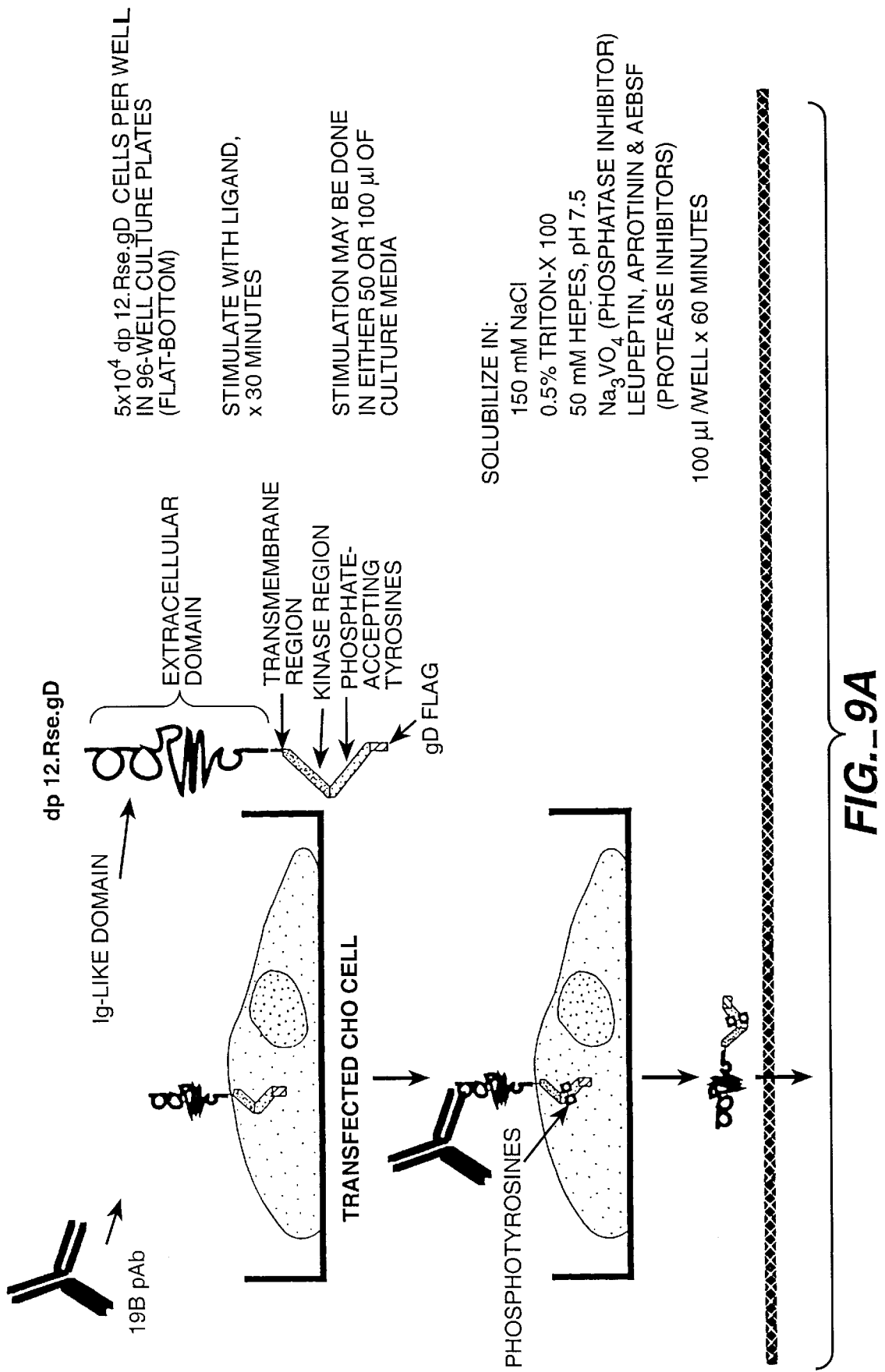
FIG._9A

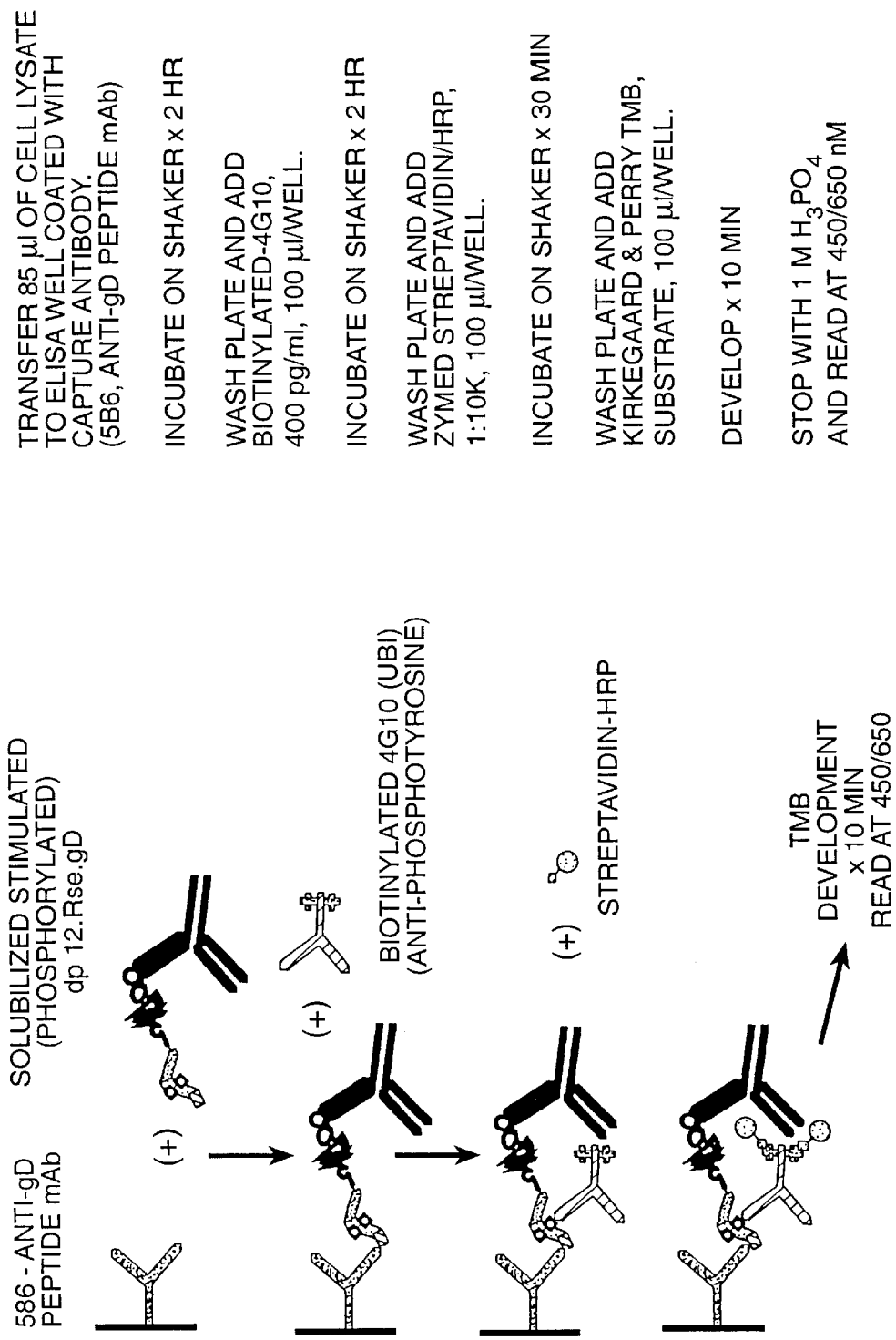
FIG._9B

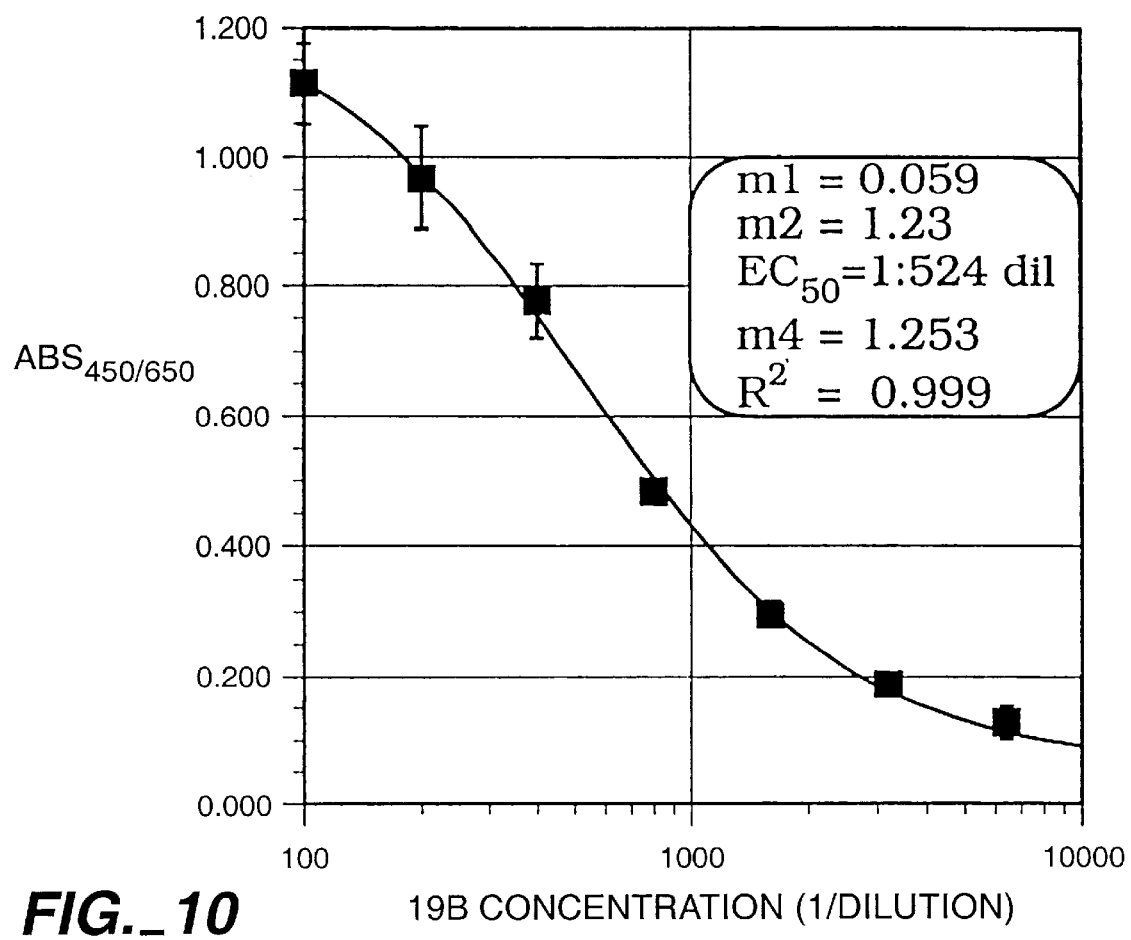
FIG._10  19B CONCENTRATION (1/DILUTION)

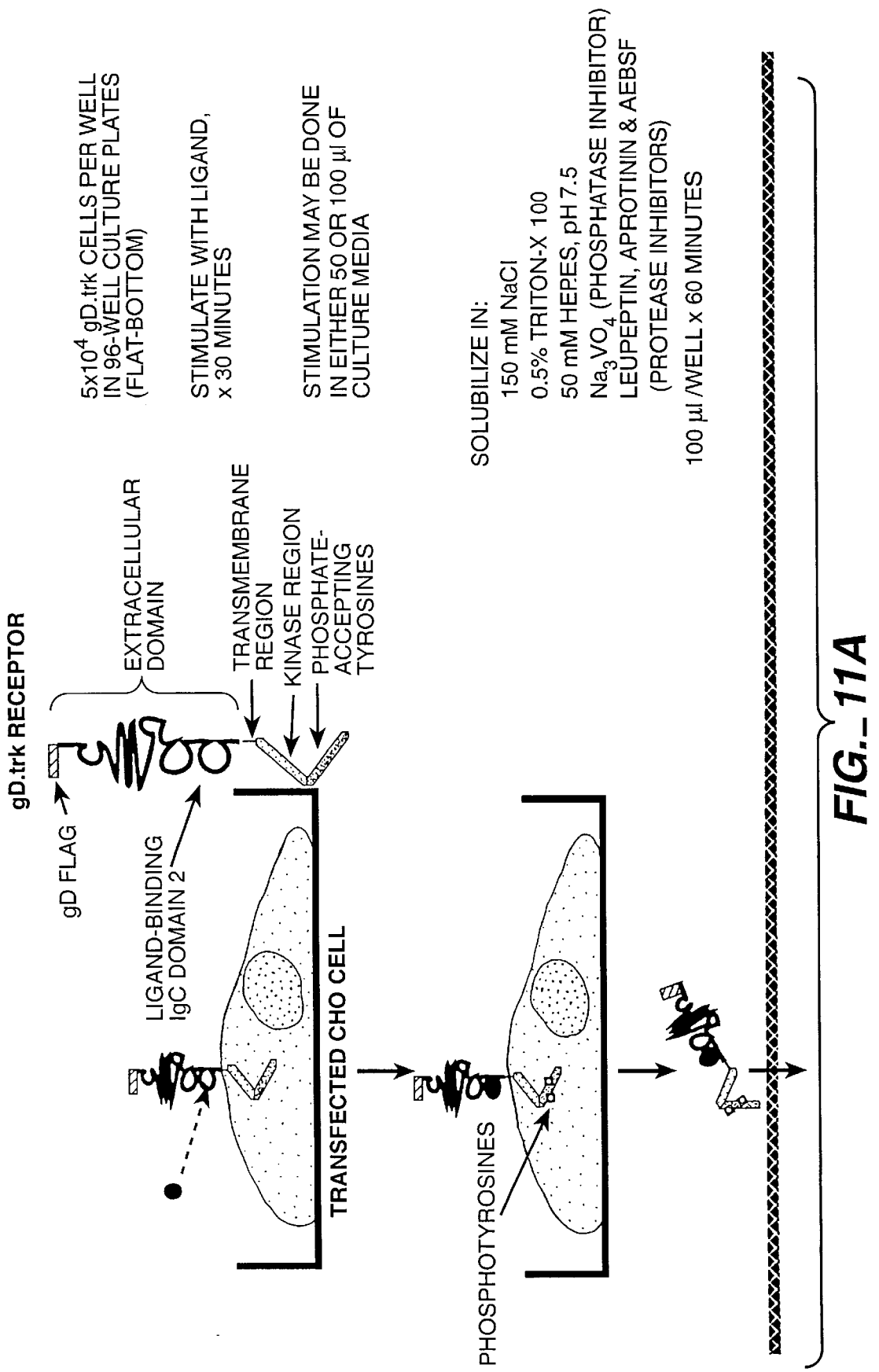
FIG._11A

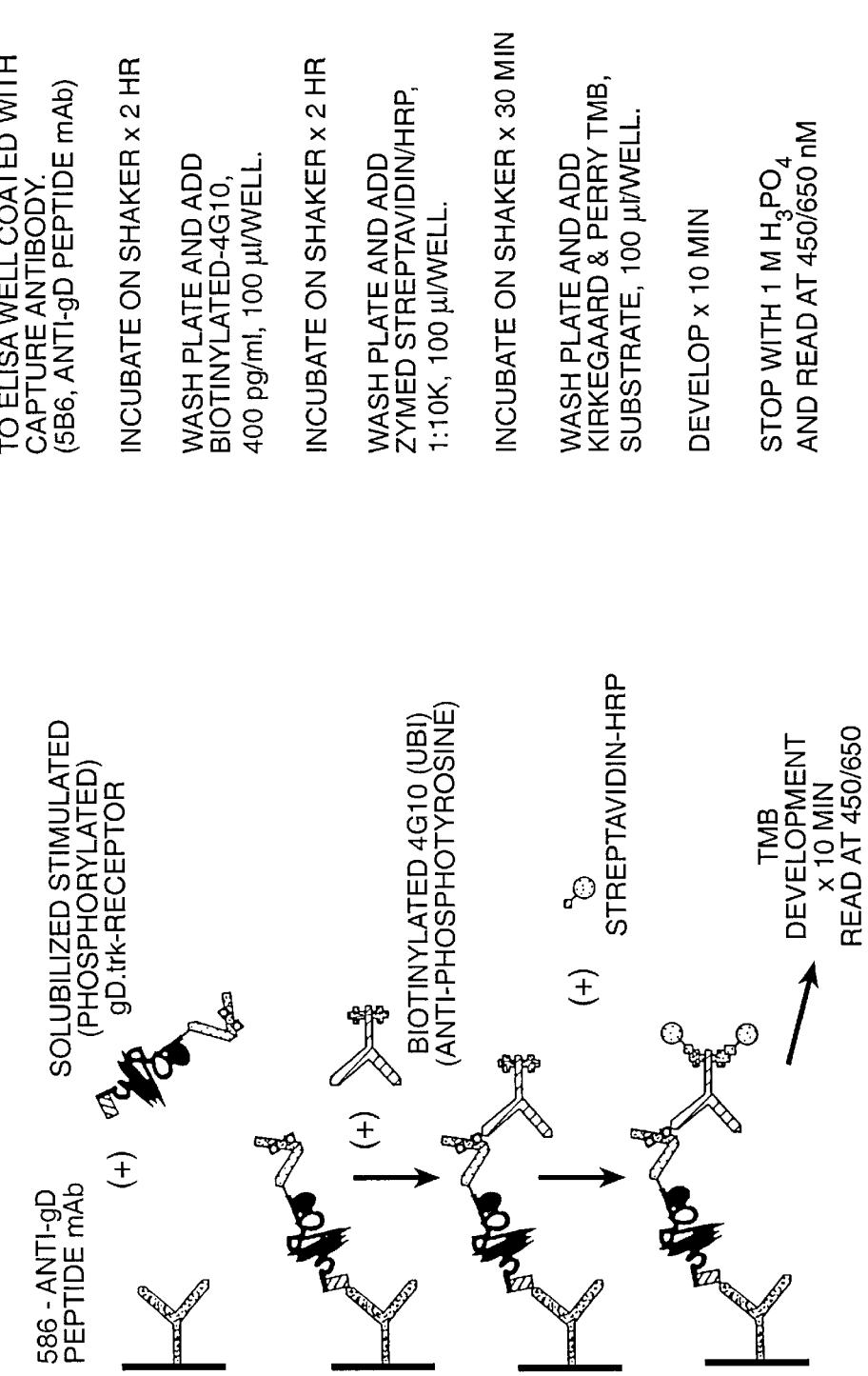
FIG._11B

```
                ^sp6 RNA start
 841   TATAGAATAA CATCCACTTT GCCTTTCTCT CCACAGGTGT CCACTCCCAG GTCCAACTGC
       ATATCTTATT GTAGGTGAAA CGGAAAGAGA GGTGTCCACA GGTGAGGGTC CAGGTTGACG ^cloning linker
                     ^R1 site mutated in
                     ^begin gD from pchadII
 901   ACCTGAATTC CACTGCCTTC CACCAAGCTC TGCAGGATCC CAGAGTCAGG GGTCTGTATC
       TGGACTTAAG GTGACGGAAG GTGGTTCGAG ACGTCCTAGG GTCTCAGTCC CCAGACATAG 961   TTCCTGCTGG TGGCTCCAGT TCAGGAACAG TAAACCCTGC TCCGAATATT GCCTCTCACA
       AAGGACGACC ACCGAGGTCA AGTCCTTGTC ATTTGGGACG AGGCTTATAA CGGAGAGTGT 1021   TCTCGTCAAT CTCCGCGAGG ACTGGGGACC CTGTGACAAG CTTCAGGCGC AACGACCAAC
       AGAGCAGTTA GAGGCGCTCC TGACCCCTGG GACACTGTTC GAAGTCGCGC TTGCTGGTTG ^Start gD
                                                       M* G* G*
1081   TACCCCGATC ATCAGTTATC CTTAAGGTCT CTTTTGTGTG GTGCCGTTCCG GTATGGGGGG
       ATGGGGCTAG TAGTCAATAG GAATTCCAGA GAAAACACAC CACGCAAGGC CATACCCCCC 1     T* A* A*    R* L* G* A*   V* I* L*   F* V* V*   I* V* G* L*   H* G* V*
1141   GACTGCCGCC AGGTTGGGGG CCGTGATTTT GTTGTCGTC ATAGTGGGCC TCCATGGGGT
       CTGACGGCGG TCCAACCCCC GGCACTAAAA CAACAGCAG TATCACCCGG AGGTACCCCA 24    R* G* K*   Y* A* L*    A  D  A  S   L  K  M   A  D  P  N  R  F  R
1201   CCGGGCAAA TATGCCTTGG CGGATGCCTC TCTCAAGATG GCCGACCCCA ATCGATTTCG
       GGCGCCGTTT ATACGGAACC GCCTACGGAG AGAGTTCTAC CGGCTGGGGT TAGCTAAAGC
```

FIG._12A

```
                                    ^Xho and GTA mutated in
                                    ^begin mature trkA
         G  K  D  L  P  V  L  D  Q  L  E  V  A  A  P  C  P  D  A
  44
1261     CGGCAAAGAC CTTCCGGTCC TGGACCAGCT GCTCGAGGTA GCCGCACCCT GCCCCGATGC
         GCCGTTTCTG GAAGGCCAGG ACCTGGTCGA CGAGCTCCAT CGGCGTGGGA CGGGGCTACG C  C  P  H  G  S  S  G  L  R  C  T  R  D  G  A  L  D  S  L
  64
1321     CTGCTGCCCC CACGGGTCCT CGGGACTGCG ATGCACCCGG GATGGGGCCC TGGATAGCCT
         GACGACGGGG GTGCCGAGGA GCCCTGACGC TACGTGGGCC CTACCCCGGG ACCTATCGGA H  H  L  P  G  A  E  N  L  T  E  L  Y  I  E  N  Q  Q  H  L
  84
1381     CCACCACCTG CCCGGCGCAG AGAACCTGAC TGAGCTCTAC ATCGAGAACC AGCAGCATCT
         GGTGGTGGAC GGGCCGCGTC TCTTGGACTG ACTCGAGATG TAGCTCTTGG TCGTCGTAGA Q  H  L  E  L  R  D  L  R  G  L  G  E  L  R  N  L  T  I  V
 104
1441     GCAGCATCTG GAGCTCCGTG ATCTGAGGGG CCTGGGGGAG CTGAGAAACC TCACCATCGT
         CGTCGTAGAC CTCGAGGCAC TAGACTCCCC GGACCCCCTC GACTCTTTGG AGTGGTAGCA K  S  G  L  R  F  V  A  P  D  A  F  H  F  T  P  R  L  S  R
 124
1501     GAAGAGTGGT CTCCGGTTTCG TGGCCGCCAGA TGCCTTCCAT TTCACTCCTC GGCTCAGTCG
         CTTCTCACCA GAGGCAAAGC ACCGCGGTCT ACGGAAGGTA AAGTGAGGAG CCGAGTCAGC L  N  L  S  F  N  A  L  E  S  L  S  W  K  T  V  Q  G  L  S
 144
1561     CCTGAATCTC TCCTTCAACG CTCTGGAGTC CTCTCTCCTG AAAACTGTGC AGGGCCTCTC
         GGACTTAGAG AGGAAGTTGC GAGACCTCAG GAGAGGAGAC TTTTGACACG TCCCGGAGAG L  Q  E  L  V  L  S  G  N  P  L  H  C  S  C  A  L  R  W  L
 164
1621     CTTACAGGAA CTGGTCCTGT CGGGGAACCC TCTGCACTGT TCTTGTGCCC TGCGCTGGCT
         GAATGTCCTT GACCAGGACA GCCCCTTGGG AGACGTGACA AGAACACGGG ACGCGACCGA
```

FIG._12B

```
184   Q   R   W   E   E   E   G   L   G   G   V   P   E   Q   K   L   Q   C   H   G
1681  ACAGCGCTGG GAGGAGGAGG GACTGGGCGG AGTGCCTGAA CAGAAGCTGC AGTGTCATGG
      TGTCGCGACC CTCCTCCTCC CTGACCCGCC TCACGGACTT GTCTTCGACG TCACAGTACC

204   Q   G   P   L   A   H   M   P   N   A   S   C   G   V   P   T   L   K   V   Q
1741  GCAAGGGCCC CTGGCCCACA TGCCCAATGC CAGCTGTGGT GTGCCCACGC TGAAGGTCCA
      CGTTCCCGGG GACCGGGTGT ACGGGTTACG GTCGACACCA CACGGGTGCG ACTTCCAGGT

224   V   P   N   A   S   V   D   V   G   D   D   V   L   L   R   C   Q   V   E   G
1801  GGTGCCCAAT GCCTCGGTGG ATGTGGGGGA CGACGTGCTG CTGCGGTGCC AGGTGGAGGG
      CCACGGGTTA CGGAGCCACC TACACCCCCT GCTGCACGAC GACGCCACGG TCCACCTCCC

244   R   G   L   E   Q   A   G   W   I   L   T   E   L   E   Q   S   A   T   V   M
1861  GCGGGGCCTG GAGCAGGCCG GCTGGATCCT CACAGAGCTG GAGCAGTCAG CCACGGTGAT
      CGCCCCGGAC CTCGTCCGGC CGACCTAGGA GTGTCTCGAC CTCGTCAGTC GGTGCCACTA

264   K   S   G   G   L   P   S   L   G   L   T   L   A   N   V   T   S   D   L   N
1921  GAAATCTGGG GGTCTGCCAT CCCTGGGGCT GACCCTGGCC AATGTCACCA GTGACCTCAA
      CTTTAGACCC CCAGACGGTA GGGACCCCGA CTGGGACCGG TTACAGTGGT CACTGGAGTT

284   R   K   N   L   T   C   W   A   E   N   D   V   G   R   A   E   V   S   V   Q
1981  CAGGAAGAAC TTGACGTGCT GGGCAGAGAA CGATGTGGGC CGGGCAGAGG TCTCTGTTCA
      GTCCTTCTTG AACTGCACGA CCCGTCTCTT GCTACACCCG GCCCGTCTCC AGAGACAAGT

304   V   N   V   S   F   P   A   L   H   T   A   V   E   M   H   H   W
2041  GGTCAACGTC TCCTTCCCGG CCAGTGTGCA GCTGCACACG GCGGTGGAGA TGCACCACTG
      CCAGTTGCAG AGGAAGGGCC GGTCACACGT CGACGTGTGC CGCCACCTCT ACGTGGTGAC
```

*FIG._12C*

```
184        Q   R   W   E   E   G   L   G   G   V   P   E   Q   K   L   Q   C   H   G
1681    ACAGGCTGG GAGGAGGAGG GACTGGGCGG AGTGCCTGAA CAGAAGCTGC AGTGTCATGG
        TGTCGGCGACC CTCCTCCTCC CTGACCCGCC TCACGGACTT GTCTTCGACG TCACAGTACC

204        Q   G   P   L   A   H   M   P   N   A   S   C   G   V   P   T   L   K   V   Q
1741    GCAAGGGCCC CTGGCCCACA TGCCCAATGC CAGCTGTGGT GTGCCCACGC TGAAGGTCCA
        CGTTCCCGGG GACCGGGTGT ACGGGTTACG GTCGACACCA CACGGGTGCG ACTTCCAGGT

224        V   P   N   A   S   V   D   V   G   D   D   V   L   L   R   C   Q   V   E   G
1801    GGTGCCCAAT GCCTCGGTGG ATGTGGGGGA CGACGTGCTG CTGCGGTGCC AGGTGGAGGG
        CCACGGGTTA CGGAGCCACC TACACCCCCT GCTGCACGAC GACGCCACGG TCCACCTCCC

244        R   G   L   E   Q   A   G   W   I   L   T   E   L   E   Q   S   A   T   V   M
1861    GCGGGGCCTG GAGCAGGCCG GCTGGATCCT CACAGAGCTG GAGCAGTCAG CCACGGTGAT
        CGCCCCGGAC CTCGTCCGGC CGACCTAGGA GTGTCTCGAC CTCGTCAGTC GGTGCCACTA

264        K   S   G   G   L   P   S   L   G   L   T   L   A   N   V   T   S   D   L   N
1921    GAAATCTGGG GGTCTGCCAT CCCTGGGGCT GACCCTGGCC AATGTCACCA GTGACCTCAA
        CTTTAGACCC CCAGACGGTA GGGACCCCGA CTGGGACCGG TTACAGTGGT CACTGGAGTT

284        R   K   N   L   T   C   W   A   E   N   D   V   G   R   A   E   V   S   V   Q
1981    CAGGAAGAAC TTGACGTGCT GGGCAGAGAA CGATGTGGGC CGGGCAGAGG TCTCTGTTCA
        GTCCTTCTTG AACTGCACGA CCCGTCTCTT GCTACACCCG GCCCGTCTCC AGAGACAAGT

304        V   N   V   S   F   P   A   S   V   Q   L   H   T   A   V   E   M   H   H   W
2041    GGTCAACGTC TCCTTCCCGG CCAGTGTGCA GCTGCACACG GCGGTGGAGA TGCACCACTG
        CCAGTTGCAG AGGAAGGGCC GGTCACACGT CGACGTGTGC CGCCACCTCT ACGTGGTGAC
```

FIG._12D

```
464        N    K    F         G    I    N    R         P    A    V         L    A    P         E    D    G         L    A    M    S
2521   AAACAAGTTT   GGGATCAAAC   GCCCGGCTGT   GCTGGCTCCA   GAGGATGGGC   TGGCCATGTC
       TTTGTTCAAA   CCCTAGTTGG   CGGGCCGACA   CGACCGAGGT   CTCCTACCCG   ACCGGTACAG

484        L    H    F         M    T    L    G         G    S    S         L    S    P         T    E    G    K         G    S    G
2581   CCTGCATTTC   ATGACATTGG   GTGGCAGCTC   CCTGTCCCCC   ACCGAGGGCA   AAGGCTCTGG
       GGACGTAAAG   TACTGTAACC   CACCGTCGAG   GGACAGGGGG   TGGCTCCCGT   TTCCGAGACC

504        L    Q    G         H    I    I    E         N    P    Q         Y    F    S         D    A    C    V         H    H    I
2641   GCTCCAAGGC   CACATCATCG   AGAACCCACA   ATACTTCAGT   GATGCCTGTG   TTCACCACAT
       CGAGGTTCCG   GTGTAGTAGC   TCTTGGGTGT   TATGAAGTCA   CTACGGACAC   AAGTGGTGTA

524        K    R    R         D    I    V    L         K    W    E         L    P    E         Q    D    K         G    A    F    G         K    V    F
2701   CAAGCGCCGG   GACATCGTGC   TCAAGTGGGA   GCTGCCCTGA   GCAGGACAAG   GGCGCCTTTG   GGAAGGTCTT
       GTTCGCGGCC   CTGTAGCACG   AGTTCACCCT   CGACCCCTC   CGTCCTGTTC   CCGCGGAAAC   CCTTCCAGAA

544        L    A    E         C    H    N    L         A    S    E    S         A    R    Q         R    E    A    E         M    L    V    A         V    K    A
2761   CCTGCTGGAG   TGCCACAACC   TCCTGCCTGA   GCAGGACAAG   GTGCTCGGAGA   GGACTTCCAA   CGTGAGGCTG   ATGCTGGTGG   CTGTCAAGGC
       GGAACGACTC   ACGGTGTTGG   AGGACGGACT   CGTCCTGTTC   CACGAGCCTCT   CCTGAAGGTT   GCACTCCGAC   TACGACCACC   GACAGTTCCG

564        L    K    E         A    S    E    S         A    R    Q         R    E    A    E         M    L    V    A         V    K    A         L    L    T
2821   ACTGAAGGAG   GCGTCCGAGA   GTGCTCGGCA   GGACTTCCAA   CGTGAGGCTG   AGCTGCTCAC
       TGACTTCCTC   CGCAGGCTCT   CACGAGCCGT   CCTGAAGGTT   GCACTCCGAC   TCGACGAGTG

584        M    L    Q         H    Q    H    I         V    R    F         F    G    V         C    T    E    G         R    P    L
2881   CATGCTGCAG   CACCAGCACA   TCGTGCGCTT   CTTCGGCGTC   TGCACCGAGG   GCCGCCCCCT
       GTACGACGTC   GTGGTCGTGT   AGCACGCGAA   GAAGCCGCAG   ACGTGGCTCC   CGGCGGGGGA
```

FIG.—12E

| 604 | L | M | V | F | E | Y | M | R | H | G | D | L | N | R | F | L | R | S | H | G |
|---|---|---|---|---|---|---|---|---|---|---|---|---|---|---|---|---|---|---|---|---|
| 2941 | GCTCATGGTC | | | TTTGAGTATA | | | | TGCGGCACGG | | | GGACCTCAAC | | | CGCTTCCTCC | | | | GATCCCATGG | | |
| | CGAGTACCAG | | | AAACTCATAT | | | | ACGCCGTGCC | | | CCTGGAGTTG | | | GCGAAGGAGG | | | | CTAGGGTACC | | |

| 624 | P | D | A | K | L | L | A | G | G | E | D | V | A | P | G | P | L | G | L | G |
|---|---|---|---|---|---|---|---|---|---|---|---|---|---|---|---|---|---|---|---|---|
| 3001 | ACCTGATGCC | | | AAGCTGCTGG | | | | CTGGTGGGGA | | | GGATGTGGCT | | | CCAGGCCCCC | | | | TGGGTCTGGG | | |
| | TGGACTACGG | | | TTCGACGACC | | | | GACCACCCCT | | | CCTACACCGA | | | GGTCCGGGGG | | | | ACCCAGACCC | | |

| 644 | Q | L | L | A | V | A | S | Q | V | A | A | G | M | V | Y | L | A | G | L | H |
|---|---|---|---|---|---|---|---|---|---|---|---|---|---|---|---|---|---|---|---|---|
| 3061 | GCAGCTGCTG | | | GCCGTGGCTA | | | | GCCAGTCGCG | | | TGCGGGGATG | | | GTGTACCTGG | | | | CGGGTCTGCA | | |
| | CGTCGACGAC | | | CGGCACCGAT | | | | CGGTCAGCGC | | | ACGCCCCTAC | | | CACATGGACC | | | | GCCCAGACGT | | |

| 664 | F | V | H | R | D | L | A | T | R | N | C | L | V | D | Y | S | T | G | Q | L | V | K |
|---|---|---|---|---|---|---|---|---|---|---|---|---|---|---|---|---|---|---|---|---|---|---|
| 3121 | TTTGTGCAC | | | CGGGACCTGG | | | | CCACACGCAA | | | CTGTCTAGTG | | | GGCCAGGGAC | | | | TGGTGGTCAA | | | | |
| | AAAACACGTG | | | GCCCTGGACC | | | | GGTGTGCGTT | | | GACAGATCAC | | | CCGGTCCCTG | | | | ACCACCAGTT | | | | |

| 684 | I | G | D | F | G | M | S | R | D | I | Y | S | T | D | Y | Y | R | V | G | G |
|---|---|---|---|---|---|---|---|---|---|---|---|---|---|---|---|---|---|---|---|---|
| 3181 | GATTGGTGAT | | | TTTGGCATGA | | | | GCAGGGATAT | | | CTACAGCACC | | | GACTATTACC | | | | GTGTGGGAGG | | |
| | CTAACCACTA | | | AAACCGTACT | | | | CGTCCCTATA | | | GATGTCGTGG | | | CTGATAATGG | | | | CACACCCTCC | | |

| 704 | R | T | M | L | P | I | R | W | M | P | P | E | S | I | L | Y | R | K | F | T |
|---|---|---|---|---|---|---|---|---|---|---|---|---|---|---|---|---|---|---|---|---|
| 3241 | CCGCACCATG | | | CTGCCCATTC | | | | GCTGGATGCC | | | GCCCGAGAGC | | | ATCCTGTACC | | | | GTAAGTTCAC | | |
| | GGCGTGGTAC | | | GACGGGTAAG | | | | CGACCTACGG | | | CGGGCTCTCG | | | TAGGACATGG | | | | CATTCAAGTG | | |

| 724 | T | E | S | D | V | W | S | F | G | V | V | L | W | E | I | F | T | Y | G | K |
|---|---|---|---|---|---|---|---|---|---|---|---|---|---|---|---|---|---|---|---|---|
| 3301 | CACCGAGAGC | | | GACGTGTGGA | | | | GCTTCGGCGT | | | GGTGCTCTGG | | | GAGATCTTCA | | | | CCTACGGCAA | | |
| | GTGGCTCTCG | | | CTGCACACCT | | | | CGAAGCCGCA | | | CCACGAGACC | | | CTCTAGAAGT | | | | GGATGCCGTT | | |

| 744 | Q | P | W | Y | Q | L | S | N | T | E | A | I | D | C | I | T | Q | G | R | E |

FIG._12F

```
3361  GCAGCCCTGG TACCAGCTCT CCAACACGGA GGCAATCGAC TGCATCACGC AGGGACGTGA
      CGTCGGGACC ATGGTCGAGA GGTTGTGCCT CCGTTAGCTG ACGTAGTGCG TCCCTGCACT

764     L   E   R   P   R   A   C   P   P   E   V   Y   A   I   M   R   G   C   W   Q
3421  GTTGGAGCGG CCACGTGCCT GCCCACCAGA GGTCTACGCC ATCATGCGGG GCTGCTGGCA
      CAACCTCGCC GGTGCACGGA CGGGTGGTCT CCAGATGCGG TAGTACGCCC CGACGACCGT

784     R   E   P   Q   Q   R   H   S   I   K   D   V   H   A   R   L   Q   A   L   A
3481  GCGGGAGCCC CAGCAACGCC ACAGCATCAA GGATGTGCAC GCCCGGCTGC AAGCCCTGGC
      CGCCCTCGGG GTCGTTGCGG TGTCGTAGTT CCTACACGTG CGGGCCGACG TTCGGGACCG

R1 site added with cloning primer^
                R1 site removed with cut and fill^

804     Q   A   P   P   V   Y   L   D   V   L   G   Q
3541  CCAGGCACCT CCTGTCTACC TGGATGTCCT GGGCTAGAAT TAATTCAATC GATGGCCGCC
      GGTCCGTGGA GGACAGATGG ACCTACAGGA CCCGATCTTA ATTAAGTTAG CTACCGGCGG

^sv40 early poly A
3601  ATGGCCCAAC TTGTTTATTG CAGCTTATAA TGGTTACAAA TAAAGCAATA GCATCACAAA
      TACCGGGTTG AACAAATAAC GTCGAATATT ACCAATGTTT ATTTCGTTAT CGTAGTGTTT
```

FIG._12G

```
      ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker    ^begin gD from pchadII
 901  ACCTCGGTTC TATCGATTGA ATTCCACTGC CTTCCACCAA GCTCTGCAGG ATCCCAGAGT
      TGGAGCCAAG ATAGCTAACT TAAGGTGACG GAAGGTGGTT CGAGACGTCC TAGGGTCTCA 961  CAGGGGTCTG TATCTTCCTG CTGGTGGCTC CAGTTCAGGA ACAGTAAACC CTGCTCCGAA
      GTCCCCAGAC ATAGAAGGAC GACCACCGAG GTCAAGTCCT TGTCATTTGG GACGAGGCTT 1021  TATTGCCTCT CACATCTCGT CAATCTCCGC GAGGACTGGG GACCCTGTGA CAAGCTTCAG
      ATAACGGAGA GTGTAGAGCA GTTAGAGGCG CTCCTGACCC CTGGGACACT GTTCGAAGTC 1081  CGCGAACGAC CAACTACCCC GATCATCAGT TATCCTTAAG GTCTCTTTTG TGTGGTGCGT
      GCGCTTGCTG GTTGATGGGG CTAGTAGTCA ATAGGAATTC CAGAGAAAAC ACACCACGCA ^Start gD
      M*  G*  G*  T*  A*  A*  R*  L*   G*  A*  V*  I*  L*  F*  V*  V*  I*  V*
   1  TCCGGTATGG GGGGGACTGC CGCCAGGTTG GGGGCCGTGA TTTTGTTTGT CGTCATAGTG
      AGGCCATACC CCCCCTGACG GCGGTCCAAC CCCCGGCACT AAAACAAACA GCAGTATCAC G*  L*  H*  G*  V*  R*  G*   K*  Y*  A*   L*  A  D  A  S  L  K  M  A  D
  19  GGCCTCCATG GGGTCCGCGG GGGTCCGCGG CAAATATGCC TTGGCGGATG CCTCTCTCAA GATGGCCGAC
      CCGGAGGTAC CCCAGGCGCC CCCAGGCGCC GTTTATACGG AACCGCCTAC GGAGAGAGTT CTACCGGCTG
```

FIG._13A

```
                              xho and GTA mutated in^
                                           start mature trkB^
    39  P  N  R  F  R  G  K  D  L  P  V  L  D  Q  L  L  E  V  C  P
  1261  CCCAATCGAT TTCGCGGCAA AGACCTTCCG GTCCTGGACC AGCTGCTCGA GGTATGTCCC
        GGGTTAGCTA AAGCGCCGTT TCTGGAAGGC CAGGACCTGG TCGACGAGCT CCATACAGGG 59  T  S  C  K  C  S  A  S  R  I  W  C  S  D  P  S  P  G  I  V
  1321  ACGTCCTGCA AATGCAGTGC CTCTCGGATC TGGTGCAGCG ACCCTTCTCC TGGCATCGTG
        TGCAGGACGT TTACGTCACG GAGAGCCTAG ACCACGTCGC TGGGAAGAGG ACCGTAGCAC 79  A  F  P  R  L  E  P  N  S  V  D  P  E  N  I  T  E  I  F  I
  1381  GCATTTCCGA GATTGGAGCC TAACAGTGTA GATCCTGAGA ACATCACCGA AATTTTCATC
        CGTAAAGGCT CTAACCTCGG ATTGTCACAT CTAGGACTCT TGTAGTGGCT TTAAAAGTAG 99  A  N  Q  K  R  L  E  I  I  N  E  D  D  V  E  A  Y  V  G  L
  1441  GCAAACCAGA AAAGGTTAGA AATCATCAAC GAAGATGATG TTGAAGCTTA TGTGGGACTG
        CGTTTGGTCT TTTCCAATCT TTAGTAGTTG CTTCTACTAC AACTTCGAAT ACACCCTGAC 119  R  N  L  T  I  V  D  S  G  L  K  F  V  A  H  K  A  F  L  K
  1501  AGAAATCTGA CAATTGTGGA TTCTGGATTA AAATTTGTGG CTCATAAAGC ATTTCTGAAA
        TCTTTAGACT GTTAACACCT AAGACCTAAT TTTAAACACC GAGTATTTCG TAAAGACTTT 139  N  S  N  L  Q  H  I  N  F  T  R  N  K  L  T  S  L  S  R  K
  1561  AACAGCAACC TGCAGCACAT CAATTTTACC CGAAACAAAC TGACGAGTTT GTCTAGGAAA
        TTGTCGTTGG ACGTCGTGTA GTTAAAATGG GCTTTGTTTG ACTGCTCAAA CAGATCCTTT 159  H  F  R  H  L  D  L  S  E  L  I  L  V  G  N  P  F  T  C  S
  1621  CATTTCCGTC ACCTTGACTT GTCTGAACTG ATCCTGGTGG GCAATCCATT TACATGCTCC
        GTAAAGGCAG TGGAACTGAA CAGACTTGAC CAGGACCACC CGTTAGGTAA ATGTACGAGG
```

FIG.-13B

```
179   C   D   I   M   W   I   K   T   L   Q   E   A   K   S   S   P   D   T   Q   D
1681  TGTGACATTA TGTGGATCAA ACACCTAGTT GACTCTCCAA GAGGCTAAAT CCAGTCCAGA CACTCAGGAT
      ACACTGTAAT ACACCTAGTT  (complement) CTGAGAGGTT CTCCGATTTA GGTCAGGTCT GTGAGTCCTA 199   L   Y   C   L   N   E   S   S   K   N   I   P   L   A   N   L   Q   I   P   N
1741  TTGTACTGCC TGAATGAAAG CAGCAAGAAT ATTCCCCTGG CAAACCTGCA GATACCCAAT
      AACATGACGG ACTTACTTTC GTCGTTCTTA TAAGGGGACC GTTTGGACGT CTATGGGTTA 219   C   G   L   P   S   A   N   L   A   A   P   N   L   T   V   E   E   G   K   S
1801  TGTGGTTTGC CATCTGCAAA TCTGGCCGCA CCTAACCTCA CTGTGGAGGA AGGAAAGTCT
      ACACCAAACG GTAGACGTTT AGACCGGCGT GGATTGGAGT GACACCTCCT TCCTTTCAGA 239   I   T   L   S   C   S   V   A   G   D   P   V   P   N   M   Y   W   D   V   G
1861  ATCACATTAT CCTGTAGTGT GGCAGGTGAT CCGGTTCCTA ATATGTATTG GGATGTTGGT
      TAGTGTAATA GGACATCACA CCGTCCACTA GGCCAAGGAT TATACATAAC CCTACAACCA 259   N   L   V   S   K   H   M   N   E   T   S   H   T   Q   G   S   L   R   I   T
1921  AACCTGGTTT CCAAACATAT GAATGAAACA AGCCACACAC AGGGCTCCTT AAGGATAACT
      TTGGACCAAA GGTTTGTATA CTTACTTTGT TCGGTGTGTG TCCCGAGGAA TTCCTATTGA 279   N   I   S   S   D   D   S   G   K   Q   A   E   N   L   V   G
1981  AACATTTCAT CCGATGACAG TGGGAAGCAG ATCTCTTGTG TGGCGGAAAA TCTTGTAGGA
      TTGTAAAGTA GGCTACTGTC ACCCTTCGTC TAGAGAACAC ACCGCCTTTT AGAACATCCT 299   E   D   Q   D   S   V   N   L   T   V   H   F   A   P   T   I   T   F   L   E
2041  GAAGATCAAG ATTCTGTCAA CCTCACTGTG CATTTTGCAC CAACTATCAC ATTTCTCGAA
      CTTCTAGTTC TAAGACAGTT GGAGTGACAC GTAAAACGTG GTTGATAGTG TAAAGAGCTT
```

FIG.—13C

```
319  S P T S  D H H  W C I  P F T V  K G N  P K P
2101 TCTCCAACCT CAGACCACCA CTGGTGCATT CCATTCACTG TGAAAGGCAA CCCAAAACCA
     AGAGGTTGGA GTCTGGTGGT GACCACGTAA GGTAAGTGAC ACTTTCCGTT GGGTTTTGGT

339  A L Q W  F Y N  G A I  L N E S  K Y I  C T K
2161 GCGCTTCAGT GGTTCTATAA CGGGGCAATA TTGAATGAGT CCAAATACAT CTGTACTAAA
     CGCGAAGTCA CCAAGATATT GCCCCGTTAT AACTTACTCA GGTTTATGTA GACATGATTT

359  I H V T  N H T  E Y H  G C L Q  L D N  P T H
2221 ATACATGTTA CCAATCACAC GGAGTACCAC GGCTGCCTCC AGCTGGATAA TCCCACTCAC
     TATGTACAAT GGTTAGTGTG CCTCATGGTG CCGACGGAGG TCGACCTATT AGGGTGAGTG

379  M N N G  D Y T  L I A  K N E Y  G K D  E K Q
2281 ATGAACAATG GGGACTACAC TCTAATAGCC AAGAATGAGT ATGGGAAGGA TGAGAAACAG
     TACTTGTTAC CCCTGATGTG AGATTATCGG TTCTTACTCA TACCCTTCCT ACTCTTTGTC

399  I S A H  F M G  W P G  I D D G  A N P  N Y P
2341 ATTTCTGCTC ACTTCATGGG CTGGCCTGGA ATTGACGATG GTGCAAACCC AAATTATCCT
     TAAAGACGAG TGAAGTACCC GACCGGACCT TAACTGCTAC CACGTTTGGG TTTAATAGGA

419  D V I Y  E D Y  G T A  A N D I  G D T  T N R
2401 GATGTAATTT ATGAAGATTA TGGAACTGCA GCGAATGACA TCGGGGACAC CACGAACAGA
     CTACATTAAA TACTTCTAAT ACCTTGACGT CGCTTACTGT AGCCCCTGTG GTGCTTGTCT

439  S N E I  P S T  D V T  D K T G  R E H  L S V
2461 AGTAATGAAA TCCCCTTCCA CAGACGTCAC TGATAAAACC GGTCGGGAAC ATCTCTCGGTC
     TCATTACTTT AGGGGAAGGT GTCTGCAGTG ACTATTTTGG CCAGCCCTTG TGAGAGCCAG

459  Y A V V  V I A  S V V  G F C L  L V M  L F L
2521 TATGCTGTGG TGGTGATTGC GTCTGTGGTG GGATTTTGCC TTTTGGTAAT GCTGTTTCTG
     ATACGACACC ACCACTAACG CAGACACCAC CCTAAAACGG AAAACCATTA CGACAAAGAC
```

FIG._13D

```
479  L   K   L   A   R   H   S   K   F   G   M   K   G   P   A   S   V   I   S   N
2581 CTTAAGTTGG CAAGACACTC AGCCTTCAAC CAAGTTTGGC ATGAAAGGCC CAGCCTTCCGT TATCAGCAAT
     GAATTCAACC GTTCTGTGAG GTTCAAACCG TACTTTCCGG GTCGGAGGCA ATAGTCGTTA

499  D   D   D   S   A   S   P   L   H   H   I   S   N   G   S   N   T   P   S   S
2641 GATGATGACT CTGCCAGCCC ACTCCATCAC ATCTCCAATG GGAGTAACAC CCTCATTGTG TCCATCTCT
     CTACTACTGA GACGGTCGGG TGAGGTAGTG TAGAGGTTAC CCTCATTGTG AGGTAGAAGA

519  S   E   G   G   P   D   A   V   I   I   G   M   T   K   I   P   V   I   E   N
2701 TCGGAAGGTG GCCCAGATGC TGTCATTATT GGAATGACCA AGATCCCTGT CATTGAAAAT
     AGCCTTCCAC CGGGTCTACG ACAGTAATAA CCTTACTGGT TCTAGGGACA GTAACTTTTA

539  P   Q   Y   F   G   I   T   N   S   Q   L   K   P   D   T   F   V   Q   H   I
2761 CCCCAGTACT TTGGCATCAC CAACAGTCAG CTCAAGCCAG ACACATTTGT TCAGCACATC
     GGGGTCATGA AACCGTAGTG GTTGTCAGTC GAGTTCGGTC TGTGTAAACA AGTCGTGTAG

559  K   R   H   N   I   V   L   K   R   E   L   G   E   G   A   F   G   K   V   F
2821 AAGCGACATA ACATTGTTCT GAAAAGGGAG CTAGGCGAAG GAGCCTTTGG AAAAGTGTTC
     TTCGCTGTAT TGTAACAAGA CTTTTCCCTC GATCCGCTTC CTCGGAAACC TTTTCACAAG

579  L   A   E   C   Y   N   L   C   P   E   Q   D   K   I   L   V   A   V   K   T
2881 CTAGCTGAAT GCTATAACCT CTGTCCTGAG CAGGACAAGA TCCTTGTGGC AGTGAAGACC
     GATCGACTTA CGATATTGGA GACAGGACTC GTCCTGTTCT AGAACCACCG TCACTTCTGG

599  L   K   D   A   S   D   N   A   R   K   D   F   H   R   E   A   E   L   L   T
2941 CTGAAGGATG CCAGTGACAA TGCACGCAAG GACTTCCACC GTGAGGCCGA GCTCCTGACC
     GACTTCCTAC GGTCACTGTT ACGTGCGTTC CTGAAGGTGG CACTCCGGCT CGAGGACTGG
```

*FIG._13E*

```
619  N   L   Q   H   E   H   I   V   K   F   Y   G   V   C   V   E   G   D   P   L
3001 AACCTCCAGC ATGAGCACAT CGTCAAGTTC TATGGCGTCT GCGTGGAGGG CGACCCCCTC
     TTGGAGGTCG TACTCGTGTA GCAGTTCAAG ATACCGCAGA CGCACCTCCC GCTGGGGGAG

639  I   M   V   F   E   Y   M   K   H   G   D   L   N   K   F   L   R   A   H   G
3061 ATCATGGTCT TTGAGTACAT GAAGCATGGG GACCTCAACA AGTTCCTCAG GGCACACGGC
     TAGTACCAGA AACTCATGTA CTTCGTACCC CTGGAGTTGT TCAAGGAGTC CCGTGTGCCG

659  P   D   A   V   L   M   A   E   G   N   P   P   T   E   L   T   Q   S   Q   M
3121 CCTGATGCCG TGCTGATGGC TGAGGGCAAC CCGCCCACGG AACTGACGCA GTCGCAGATG
     GGACTACGGC ACGACTACCG ACTCCCGTTG GGCGGGTGCC TTGACTGCGT CAGCGTCTAC

679  L   H   I   A   Q   Q   I   A   A   G   M   V   Y   L   A   S   Q   H   F   V
3181 CTGCATATAG CCCAGCAGAT CGCCGCGGGC ATGGTCTACC TGGCCGTCCA GCACTTCGTG
     GACGTATATC GGGTCGTCTA GCGGCGCCCG TACCAGATGG ACCGGCAGGT CGTGAAGCAC

699  H   R   D   L   A   T   R   N   C   L   V   G   E   N   L   L   V   K   I   G
3241 CACCGCGATT TGGCCACCAG GAACTGCCTG GTCGGGGAGA ACTTGCTGGT GAAAATCGGG
     GTGGCGCTAA ACCGGTGGTC CTTGACGGAC CAGCCCCTCT TGAACGACCA CTTTTAGCCC

719  D   F   G   M   S   R   D   V   Y   S   T   D   Y   Y   R   V   G   H   T
3301 GACTTTGGGA TGTCCCGGGA CGTGTACAGC ACTGACTACT ACAGGGTCGG TGGCCACACA
     CTGAAACCCT ACAGGGCCCT GCACATGTCG TGACTGATGA TGTCCCAGCC ACCGGTGTGT

739  M   L   P   I   R   W   M   P   P   E   S   I   M   Y   R   K   F   T   T   E
3361 ATGCTGCCCA TTCGCTGGAT GCCTCCAGAG AGCATCATGT ACAGGAAATT CACGACGGAA
     TACGACGGGT AAGCGACCTA CGGAGGTCTC TCGTAGTACA TGTCCTTTAA GTGCTGCCTT

759  S   D   V   W   S   L   G   V   V   L   W   E   I   F   T   Y   G   K   Q   P
3421 AGCGACGTCT GGAGCCTGGG GGTCGTGTTG TGGGAGATTT TCACCTATGG CAAACAGCCC
```

FIG._13F

```
        TCGCTGCAGA CCTCGGACCC CCAGCACAAC ACCCTCTAAA AGTGGATACC GTTTGTCGGG
779     W  Y  Q  L     S  N  N     E  V  I     E  C  I  T     Q  G  R     V  L  Q
3481    TGGTACCAGC TGTCAAACAA TGAGGTGATA GAGTGTATCA CTCAGGGCCG AGTCCTGCAG
        ACCATGGTCG ACAGTTTGTT ACTCCACTAT CTCACATAGT GAGTCCCGGC TCAGGACGTC

799     R  P  R  T     C  P  Q     E  V  Y     E  L  M  L     G  C  W     Q  R  E
3541    CGACCCCGCA CGTGCCCCCA GGAGGTGTAT GAGCTGATGC TGGGGTGCTG GCAGCGAGAG
        GCTGGGGCGT GCACGGGGGT CCTCCACATA CTCGACTACG ACCCCACGAC CGTCGCTCTC

819     P  H  M  R     K  N  I     K  G  I     H  T  L  L     Q  N  L     A  K  A
3601    CCCCACATGA GGAAGAACAT CAAGGGCATC CATACCCTCC TTCAGAACTT GGCCAAGGCA
        GGGGTGTACT CCTTCTTGTA GTTCCCGTAG GTATGGGAGG AAGTCTTGAA CCGGTTCCGT

839     S  P  V  Y     L  D  I     L  G  Q
3661    TCTCCGGTCT ACCTGGACAT TCTAGGCTAG GGCCCTTTTC CCCAGACCGA TCCTTCCCAA
        AGAGGCCAGA TGGACCTGTA AGATCCGATC CCGGGAAAAG GGGTCTGGCT AGGAAGGGTT

3721    CGTACTCCTC AGACGGGGCTG AGAGGATGAA CATCTTTTAA CCGAGAAGACT CTCGACCTGC
        GCATGAGGAG TCTGCCCCGAC TCTCCTACTT GTAGAAAATT GGCTCTTCTGA GAGCTGGACG half Xho half Sal site from subcloning^
3781    GCTGCTCTCC TTCACTCTGA CAGTATTAAC ATCAAAGACT CCGAGAAGCT CTCGACCTGC
        CGACGAGAGG AAGTGAGACT GTCATAATTG TAGTTTCTGA GGCTCTTCGA GAGCTGGACG ^sv40 early poly A
3841    AGAAGCTTGG CCGCCATGGC CCAACTTGTT TATTGCAGCT TATAATGGTT ACAAATAAAG
        TCTTCGAACC GGCGGTACCG GGTTGAACAA ATAACGTCGA ATATTACCAA TGTTTATTTC
```

FIG._13G

```
          ^sp6 RNA start
 841  TATAGAATAA CATCCACTTT GCCTTTCTCT CCACAGGTGT CCACTCCCAG GTCCAACTGC
      ATATCTTATT GTAGGTGAAA CGGAAAGAGA GGTGTCCACA GGTGAGGGTC CAGGTTGACG ^cloning linker
              ^RI site mutated in
                ^gD from pchadII
 901  ACCTGAATTC CACTGCCTTC CACCAAGCTC TGCAGGATCC CAGAGTCAGG GGTCTGTATC
      TGGACTTAAG GTGACGGAAG GTGGTTCGAG ACGTCCTAGG GTCTCAGTCC CCAGACATAG 961  TTCCTGCTGG TGGCTCCAGT TCAGGAACAG TAAACCCTGC TCCGAATATT GCCTCTCACA
      AAGGACGACC ACCGAGGTCA AGTCCTTGTC ATTTGGGACG AGGCTTATAA CGGAGAGTGT 1021  TCTCGTCAAT CTCCGCGAGG ACTGGGGACC CTGTGACAAG CTTCAGGCGC AACGACCAAC
      AGAGCAGTTA GAGGCGCTCC TGACCCCTGG GACACTGTTC GAAGTCCGCG TTGCTGGTTG ^Start
 gD                                           M* G*  G*
  1   TACCCCGATC ATCAGTTATC CTTAAGGTCT CTTTTGTGTG GTGCCGTTCCG GTATGGGGGG
      ATGGGGCTAG TAGTCAATAG GAATTCCAGA GAAAACACAC CACGCAAGGC CATACCCCCC T*  A*  A*   R*  L*  G*  A*    V*  I*  L*    F*  V*  V*    I*  V*  G*  L*    H*  G*  V*
  4   GACTGCCGCC AGGTTGGGGG CCGTGATTTT GTTTGTCGTC ATAGTGGGCC TCCATGGGGT
      CTGACGGCGG TCCAACCCCC GGCACTAAAA CAAACAGCAG TATCACCCGG AGGTACCCCA R*  G*  K*   Y*  A*  L*  A     D   A   S    L   K   M    A   D   P   N    R   F   R
 24   CCGGGGCAAA TATGCCTTGG CGGATGCCCTC TCTCAAGATG GCCGACCCCA ATCGATTTCG
      GGCGCCCGTT ATACGGAACC GCCTACGGAG AGAGTTCTAC CGGCTGGGGT TAGCTAAAGC
```

FIG._14A

```
                                              ^Xho site and GTA mutated in
                                              ^begin mature trkC
          G   K   D   L   P   V   L   D   Q   L   E   V   C   P   A   N   C   V   C
  44
1261    CGGCAAAGAC CTTCCGGTCC TGGACCAGCT GCTCGAGGTA TGCCCTGCAA ATTGTGTCTG
        GCCGTTTCTG GAAGGCCAGG ACCTGGTCGA CGAGCTCCAT ACGGGACGTT TAACACAGAC S   K   T       E   I   N   C       R   R   P       D   D   G       N   L   F   P       L   L   E
  64
1321    CAGCAAGACT GAGATCAATT GCCGGCGGCC GGACGATGGG AACCTCTTCC CCCTCCTGGA
        GTCGTTCTGA CTCTAGTTAA CGGCCGCCGG CCTGCTACCC TTGGAGAAGG GGGAGGACCT G   Q   D       S   G   N   S       N   G   N       A   N   I       N   I   T   D       I   S   R
  84
1381    AGGGCAGGAT TCAGGGAACA GCAATGGGAA CGCCAATATC AACATCACGG ACATCTCAAG
        TCCCGTCCTA AGTCCCTTGT CGTTACCCTT GCGGTTATAG TTGTAGTGCC TGTAGAGTTC N   I   T       S   I   H   I       E   N   W       R   S   L       H   T   L   N       A   V   D
 104
1441    GAATATCACT TCCATACACA TAGAGAACTG GCGCAGTCTT CACACGCTCA ACGCCGTGGA
        CTTATAGTGA AGGTATGTGT ATCTCTTGAC CGCGTCAGAA GTGTGCGAGT TGCGGCACCT M   E   L       Y   T   G   L       Q   K   L       T   I   K       N   S   G   L       R   S   I
 124
1501    CATGGAGCTC TACACCGGAC TTCAAAAGCT GACCATCAAG AACTCAGGAC TTCGGAGCAT
        GTACCTCGAG ATGTGGCCTG AAGTTTTCGA CTGGTAGTTC TTGAGTCCTG AAGCCTCGTA Q   P   R       A   F   A   K       N   P   H       L   R   Y       I   N   L   S       N   R
 144
1561    TCAGCCCAGA GCCTTTGCCA AGAACCCCCA TTTGCGTTAT ATAAACCTGT CAAGTAACCG
        AGTCGGGTCT CGGAAACGGT TCTTGGGGGT AAACGCAATA TATTTGGACA GTTCATTGGC L   T   T       L   S   W   Q       L   F   Q       T   L   S       L   R   E   L       Q   L   E
 164
1621    GCTCACCACA CTCTCGTGGC AGCTCTTCCA GACGCTGAGT CTTCGGGAAT TGCAGTTGGA
```

FIG._14B

```
                CGAGTGGTGT GAGAGCACCG TCGAGAAGGT CTGCGACTCA GAAGCCCTTA ACGTCAACCT
       Q  N  F   F  N  C  S   C  D  I   R  W  M   Q  L  W  Q   E  Q  G
184    GCAGAACTTT TTCAACTGCA GCTGTGACAT CCGCTGGATG CAGCTCTGGC AGGAGCAGGG
1681   CGTCTTGAAA AAGTTGACGT CGACACTGTA GGCGACCTAC GTCGAGACCG TCCTCGTCCC

E  A  K   L  N  S  Q   N  L  Y   C  I  N   A  D  G  S   Q  L  P
204    GGAGGCCAAG CTCAACAGCC AGAACCTCTA CTGCATCAAT GCTGATGGCT CCCAGCTTCC
1741   CCTCCGGTTC GAGTTGTCGG TCTTGGAGAT GACGTAGTTA CGACTACCGA GGGTCGAAGG

L  F  R   M  N  I  S   Q  C  D   L  P  E   I  S  V  S   H  V  N
224    TCTCTTCCGC ATGAACATCA GTCAGTGTGA CCTTCCTGAG ATCAGCGTGA GCCACGTCAA
1801   AGAGAAGGCG TACTTGTAGT CAGTCACACT GGAAGGACTC TAGTCGCACT CGGTGCAGTT

L  T  V   R  E  G  D   N  A  V   I  T  C   N  G  S  G   S  P  L
244    CCTGACCGTA CGAGAGGGTG ACAATGCTGT TATCACTTGC AATGGCTCTG GATCACCCCT
1861   GGACTGGCAT GCTCTCCCAC TGTTACGACA ATAGTGAACG TTACCGAGAC CTAGTGGGGA

P  D  V   D  W  I  V   T  G  L   Q  S  I   N  T  H  Q   T  N  L
264    CCCTGATGTG GACTGGATAG TCACTGGGCT GCAGTCCATC AACACTCACC AGACCAATCT
1921   GGGACTACAC CTGACCTATC AGTGACCCGA CGTCAGGTAG TTGTGAGTGG TCTGGTTAGA

N  W  T   N  V  H  A   I  N  L   T  L  V   N  V  T  S   E  D  N
284    GAACTGGACC AATGTTCATG CCATCAACTT GACGCTGGTG AATGTGACGA GTGAGGACAA
1981   CTTGACCTGG TTACAAGTAC GGTAGTTGAA CTGCGACCAC TTACACTGCT CACTCCTGTT

G  F  T   L  T  C  I   A  E  N   V  V  G   M  S  N  A   S  V  A
304    TGGCTTCACC CTGACGTGCA TTGCAGAGAA CGTGGTGGGC ATGAGCAATG CCAGTGTTGC
2041   ACCGAAGTGG GACTGCACGT AACGTCTCTT GCACCACCCG TACTCGTTAC GGTCACAACG
```

*FIG._14C*

```
324   L   T   V   Y   Y   P   P   R   V   V   S   L   E   E   P   E   L   R   L   E
2101  CCTCACTGTC TACTATCCCC CACGTGTGGT GAGCCTGGAG CTCGGACCTC ACGCGGACCT
      GGAGTGACAG ATGATAGGGG GTGCACACCA CTCGGACCTC GAGCCTGGAG TGCGCCTGGA

344   H   C   I   E   F   V   V   R   G   N   P   P   P   T   L   H   W   L   H   N
2161  GCACTGCATC GAGTTTGTGG TGCGTGGCAA CCCCCCACCA ACGCTGCACT GGCTGCACAA
      CGTGACGTAG CTCAAACACC ACGCACCGTT GGGGGGTGGT TGCGACGTGA CCGACGTGTT

364   G   Q   P   L   R   E   S   K   I   I   H   V   E   Y   Y   Q   E   G   E   I
2221  TGGGCAGCCT CTGCGGGAGT CCAAGATCAT CCATGTGGAA TACTACCAAG AGGGAGAGAT
      ACCCGTCGGA GACGCCCTCA GGTTCTAGTA GGTACACCTT ATGATGGTTC TCCCTCTCTA

384   S   E   G   C   L   L   F   N   K   P   T   H   Y   N   N   G   N   Y   T   L
2281  TTCCGAGGGC TGCCTGCTCT TCAACAAGCC CACCCACTAC AACAATGGCA ACTATACCCT
      AAGGCTCCCG ACGGACGAGA AGTTGTTCGG GTGGGTGATG TTGTTACCGT TGATATGGGA

404   I   A   K   N   P   L   G   T   A   N   Q   T   I   N   G   H   F   L   K   E
2341  CATTGCCAAA AACCCACTGG GCACAGCCAA CCAGACCATC AATGGCCACT TCCTCAAGGA
      GTAACGGTTT TTGGGTGACC CGTGTCGGTT GGTCTGGTAG TTACCGGTGA AGGAGTTCCT
                 ^begin ecd insert                      ^end ecd insert 424   P   F   P   E   S   T   D   N   F   I   L   F   D   E   V   S   P   T   P   P
2401  GCCCTTTCCA GAGAGCACGG ATAACTTTAT CTTGTTTGAC GAAGTGAGTC CCACACCTCC
      CGGGAAAGGT CTCTCGTGCC TATTGAAATA GAACAAACTG CTTCACTCAG GGTGTGGAGG
                                                          ^begin TM 444   I   T   V   T   H   K   P   E   E   D   T   F   G   V   S   I   A   V   G   L
2461  TATCACTGTG ACCCACAAAC CAGAAGAAGA CACTTTTGGG GTATCCATAG CAGTTGGACT
```

FIG._14D

```
                 ATAGTGACAC TGGGTGTTTG GTCTTCTTCT GTGAAACCC  CATAGGTATC GTCAACCTGA
                                                                       ^end TM
          A    A    F    A    C    V    L    L    V    V    L    F    V    M    I    N    K    Y    G    R
464  
2521      TGCTGCTTTT GCCTGTGTCC TGTTGGTGGT TCTCTTCGTC ATGATCAACA AATATGGTCG
          ACGACGAAAA CGGACACAGG ACAACCACCA AGAGAAGCAG TACTAGTTGT TTATACCAGC R    S    K    F    G    M    K    G    P    V    A    V    I    S    G    E    E    D    S    A
484  
2581      ACGGTCCAAA TTTGGAATGA AGGGTCCCGT GGCTGTCATC AGTGGTGAGG AGGACTCAGC
          TGCCAGGTTT AAACCTTACT TCCCAGGGCA CCGACAGTAG TCACCACTCC TCCTGAGTCG S    P    L    H    H    I    N    H    G    I    T    T    P    S    S    L    D    A    G    P
504  
2641      CAGCCCACTG CACCACATCA ACCACGGCAT CACCACGCCC TCGTCACTGG ATGCCGGGCC
          GTCGGGTGAC GTGGTGTAGT TGGTGCCGTA GTGGTGCGGG AGCAGTGACC TACGGCCCGG D    T    V    V    I    G    M    T    R    I    P    V    I    E    N    P    Q    Y    F    R
524  
2701      CGACACTGTG GTCATTGGCA TGACTCGCAT CCCTGTCATT GAGAACCCCC AGTACTTCCG
          GCTGTGACAC CAGTAACCGT ACTGAGCGTA GGGACAGTAA CTCTTGGGGG TCATGAAGGC Q    G    H    N    C    H    K    P    D    T    Y    V    Q    H    I    K    R    D    I
544  
2761      TCAGGGACAC AACTGCCACA AGCCCGACAC GTATGTGCAG CACATTAAGA GGAGAGACAT
          AGTCCCTGTG TTGACGGTGT TCGGGCTGTG CATACACGTC GTGTAATTCT CCTCTCTGTA
                     ^begin TK V    L    K    R    E    L    G    E    G    A    F    G    K    V    F    L    A    E    C    Y
564  
2821      CGTGCTGAAG CGAGAACTGG GTGAGGGAGC CTTTGGAAAG GTCTTCCTGG CCGAGTGCTA
          GCACGACTTC GCTCTTGACC CACTCCCTCG GAAACCTTTC CAGAAGGACC GGCTCACGAT
```

*FIG._14E*

```
584   N  L  S     P  T  K  D     K  M  L     V  A  V     K  A  L  K     D  P  T
2881  CAACCTCAGC  CCGACCAAGG  ACAAGATGCT  TGTGGCTGTG  AAGGCCCTGA  AGGATCCCAC
      GTTGGAGTCG  GGCTGGTTCC  TGTTCTACGA  ACACCGACAC  TTCCGGGACT  TCCTAGGGTG

604   L  A  A     R  K  D  F     Q  R  E     A  E  L     L  T  N  L     Q  H  E
2941  CCTGGCTGCC  CGGAAGGATT  TCCAGAGGGA  GGCCGAGCTG  CTCACCAACC  TGCAGCATGA
      GGACCGACGG  GCCTTCCTAA  AGGTCTCCCT  CCGGCTCGAC  GAGTGGTTGG  ACGTCGTACT

624   H  I  V     K  F  Y  G     V  C  G     D  G  D     P  L  I  M     V  F  E
3001  GCACATTGTC  AAGTTCTATG  GAGTGTGCGG  CGATGGGGAC  CCCCTCATCA  TGGTCTTTGA
      CGTGTAACAG  TTCAAGATAC  CTCACACGCC  GCTACCCCTG  GGGGAGTAGT  ACCAGAAACT

644   Y  M  K     H  G  D  L     N  K  F     L  R  A     H  G  P  D     A  M  I
3061  ATACATGAAG  CATGGAGACC  TGAATAAGTT  CCTCAGGGCC  CATGGGCCAG  ATGCAATGAT
      TATGTACTTC  GTACCTCTGG  ACTTATTCAA  GGAGTCCCGG  GTACCCGGTC  TACGTTACTA

664   L  V  D     G  Q  P  R     Q  A  K     G  E  L     G  L  S  Q     M  L  H
3121  CCTTGTGGAT  GGACAGCCAC  GCCAGGCCAA  GGGTGAGCTG  GGGCTCTCCC  AAATGCTCCA
      GGAACACCTA  CCTGTCGGTG  CGGTCCGGTT  CCCACTCGAC  CCCGAGAGGG  TTTACGAGGT

684   I  A  S     Q  H  F  R     Q  A  K     G  M  V     Y  L  A     V  H  R
3181  CATTGCCAGT  CAGATGCCT  CGGGTATGGT  GTACCTGGCC  GTACCTGGCC  TTGTGCACCG
      GTAACGGTCA  GTCTAGCGGA  GCCCATACCA  CATGGACCGG  CATGGACCGG  AACACGTGGC

704   D  L  A     T  R  N  C     L  V  G     A  N  L     L  V  K  I     G  D  F
3241  AGACCTGGCC  ACCAGGAACT  GCCTGGTTGG  AGCGAATCTG  CTAGTGAAGA  TTGGGGACTT
      TCTGGACCGG  TGGTCCTTGA  CGGACCAACC  TCGCTTAGAC  GATCACTTCT  AACCCCTGAA
                                                     ^TK insert site 724   G  M  S     R  D  V  Y     S  T  D     Y  Y  R     V  G  G  H     T  M  L
```

FIG._14F

```
3301 CGGCATGTCC AGAGATGTCT ACAGCACGGA TTATTACAGG GTGGGAGGAC ACACCATGCT
     GCCGTACAGG TCTCTACAGA TGTCGTGCCT AATAATGTCC CACCCTCCTG TGTGGTACGA

744    P    I    R       W    M    P    P       E    S    I       M    Y    R       K    F    T       E    S    D
3361 CCCCATTCGC TGGATGCCTC CTGAAAGCAT CATGTACCGG AAGTTCACTA CAGAGAGTGA
     GGGGTAAGCG ACCTACGGAG GACTTTCGTA GTACATGGCC TTCAAGTGAT GTCTCTCACT

764    V    W    S       F    G    V    I       L    W    E       I    F    T       Y    G    K    Q       P    W    F
3421 TGTATGGAGC TTCGGGGTGA TCCTCTGGGA GATCTTCACC TATGGAAAGC AGCCATGGTT
     ACATACCTCG AAGCCCCACT AGGAGACCCT CTAGAAGTGG ATACCTTTCG TCGGTACCAA

784    Q    L    S       N    T    E    V       I    E    C       I    T    Q       G    R    V    L       E    R    P
3481 CCAACTCTCA AACACGGAGG TCATTGAGTG CATTACCCAA GGTCGTGTTT TGGAGCGGCC
     GGTTGAGAGT TTGTGCCTCC AGTAACTCAC GTAATGGGTT CCAGCACAAA ACCTCGCCGG

804    R    V    C       P    K    E    V       Y    D    V       M    L    G       C    W    Q    R       E    P    Q
3541 CCGAGTCTGC CCCAAAGAGG TGTACGATGT CATGCTGGGG TGCTGGCAGA GGGAACCACA
     GGCTCAGACG GGGTTTCTCC ACATGCTACA GTACGACCCC ACGACCGTCT CCCTTGGTGT

824    Q    R    L       N    I    K    E       I    Y    K       I    L    H       A    L    G    K       A    T    P
3601 GCAGCGGTTG AACATCAAGG AGATCTACAA AATCCTCCAT GCTTTGGGGA AGGCCACCCC
     CGTCGCCAAC TTGTAGTTCC TCTAGATGTT TTAGGAGGTA CGAAACCCCT· TCCGGTGGGG
                                      ^stop
                                      R1 site removed with cut and fill^

844    I    Y    L       D    I    L    G       O
3661 AATCTACCTG GACATTCTTG GCTAGTGGTG GCTGGTGGTC ATGAATTAAT TCAATCGATG
     TTAGATGGAC CTGTAAGAAC CGATCACCAC CGACCACCAG TACTTAATTA AGTTAGCTAC
                                                 ^sv40 early poly A 3721 GCCGCCATGG CCCAACTTGT TTATTGCAGC TTATAATGGT TACAAATAAA GCAATAGCAT
     CGGCGGTACC GGGTTGAACA AATAACGTCG AATATTACCA ATGTTTATTT CGTTATCGTA
```

FIG._14G

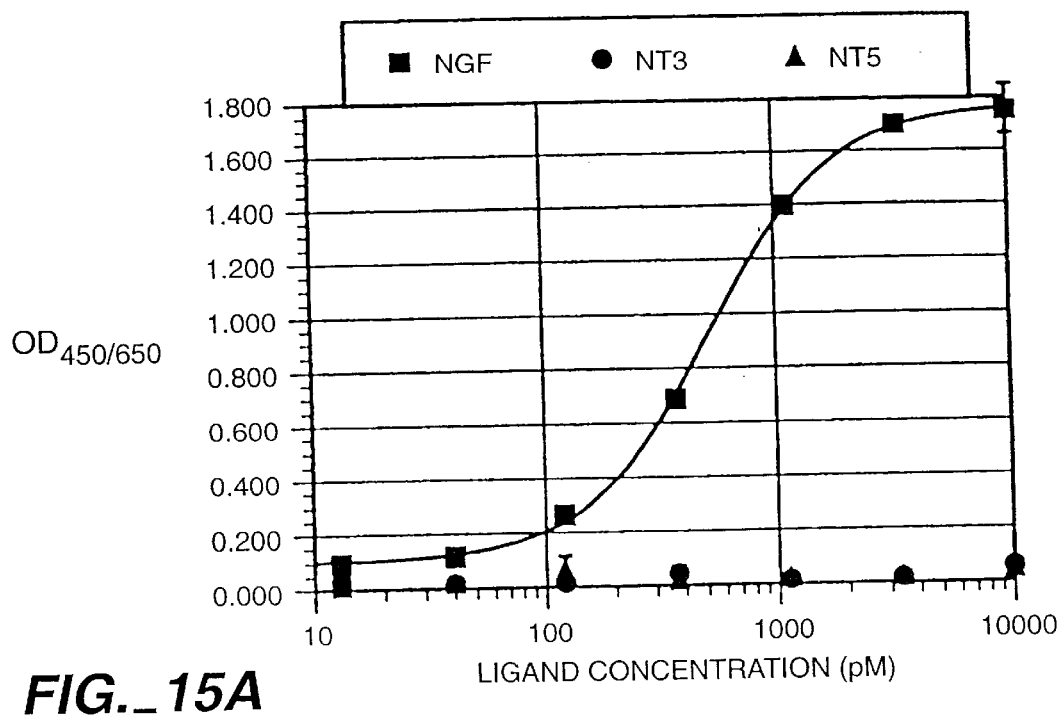
FIG._15A

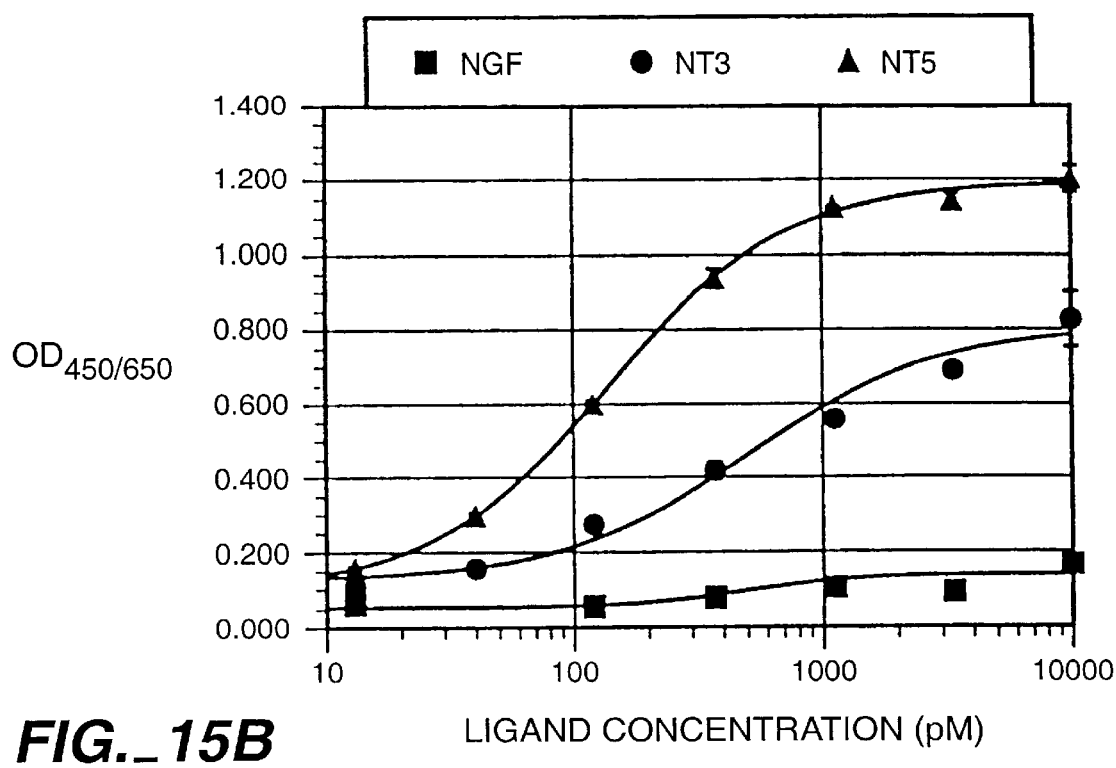
FIG._15B
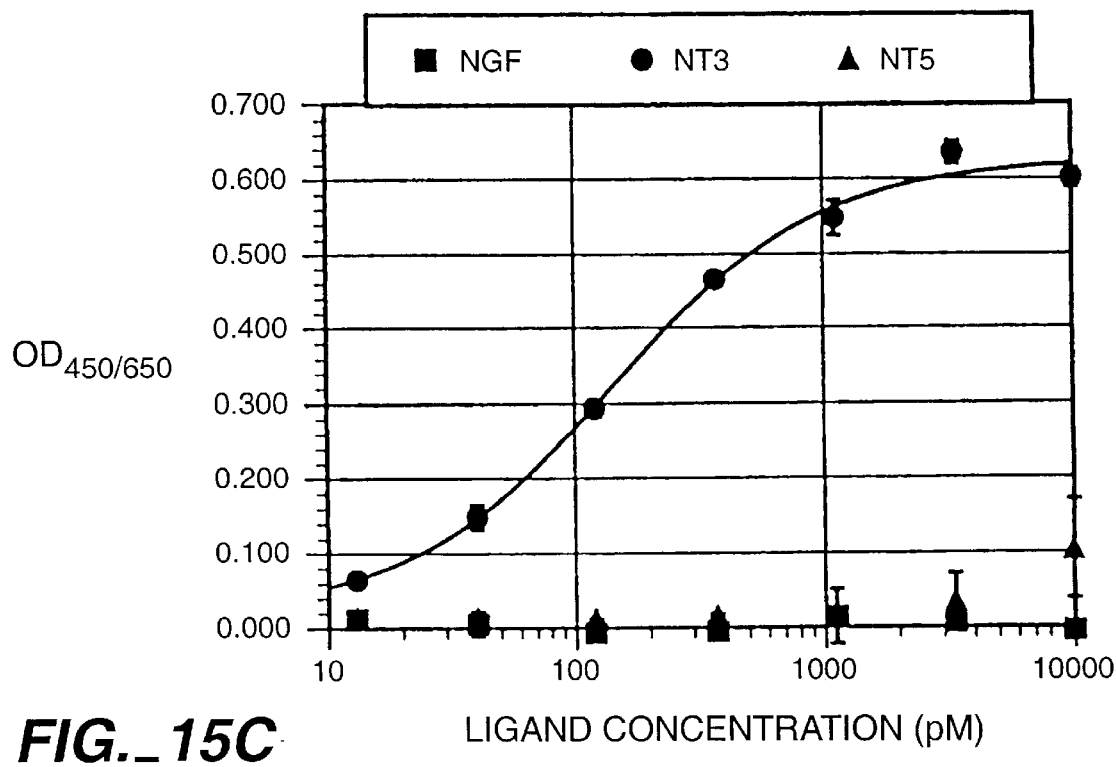
FIG._15C

FIG._16A

```
    aluI
    sstI
    sacI
    hgiJII
    hgiAI/asphI                                           aluI
    ecl136II                                     sau3AI pvuII
    bsp1286                                    mboI/ndeII[dam-]
    bsiHKAI                                       dpnI[dam+]
    bmyI                                           pvuI/bspCI
    banII                                      pleI dpnII[dam-]
                                                 hinfI  taqI[dam-]
    taqI                                rmaI   mcrI      nspBII
                                         maeI  taqI[dam-]
  1 TTCGAGCTCG CCCGACATTG ATTATTGACT AGAGTCGATC GACAGCTGTG GAATGTGTGT CAGTTAGGGT
    AAGCTCGAGC GGGCTGTAAC TAATAACTGA TCTCAGCTAG CTGTCGACAC CTTACACACA GTCAATCCCA nlaIV
                  scrFI                                           sfaNI        scrFI
                  mvaI                                           ppu10I        mvaI
                  ecoRII                                        nsiI/avaIII    ecoRII
                  dsaV                                            nlaIII       dsaV
                  bstNI                                            sphI        bstNI
                  apyI[dcm+]                                       nspI        apyI
                  bsaJI                                           nspHI        sexAI
 71 GTGGAAAGTC CCCAGGCTCC CCAGCAGGCA GAAGTATGCA AAGCATGCAT CTCAATTAGT CAGCAACCAG
    CACCTTTCAG GGGTCCGAGG GGTCGTCCGT CTTCATACGT TTCGTACGTA GAGTTAATCA GTCGTTGGTC
```

FIG._16B

```
                                                                    nlaIV
              scrFI
                mvaI                        sfaNI
              ecoRII                       nsiI/avaIII  ppuloI
              dsaV                         nlaIII
                 bstNI                              sphI
       [dcm+]   apyI[dcm+]                          nspI
                bsaJI                               nspHI
                                                                          nlaIII
                                                                          styI
                                                                          ncoI
                                                                    bslI dsaI
                                                                    aciI bsaJI
141 GTGTGGAAAG TCCCCAGGCT CCCCAGCAGG CAGAAGTATG CAAAGCATGC ATCTCAATTA GTCAGCAACC
    CACACCTTTC AGGGGTCCGA GGGGTCGTCC GTCTTCATAC GTTTCGTACG TAGAGTTAAT CAGTCGTTGG fnu4HI
                                                   bglI
                                                   sfiI
                                                   haeIII/palI
                                              mnlI  mnlI   ddeI
       aciI           aciI  fokI   aciI bsrI aciI  haeIII/palI bsaJI mnlI  aluI
       aciI  CCCTAACTC GCCCATCCCG CGCCAGTTC CGCCCATTCT CGCCCCCATG
211 ATAGTCCCGC CCCTAACTC GCCCATCCCG CGCCAGTTC CGCCCATTCT CGCCCCCATG
    TATCAGGGCG GGGATTGAGG CGGGTAGGGC GCGGTCAAG GCGGGTAAGA GCGGGGGTAC mnlI bsaJI aciI    haeIII/palI
                                                                        mnlI
281 GCTGACTAAT TTTTTTTATT TATGCAGAGG CCGAGGCCGC CTCGGCCCTC GAGCTATTCC AGAAGTAGTG
    CGACTGATTA AAAAAAATAA ATACGTCTCC GGCTCCGGCG GAGCCGGGAGA CTCGATAAGG TCTTCATCAC
```

```
                                                                    haeIII/palI
                                                                    mcrI
                                                                    eagI/xmaIII/eclXI
                                                         aluI       eaeI
                                                         rmaI       cfrI
                                                         maeI       mspI
                                                         nheI       hpaII
              rmaI                                       aluI
              styI
              bsaJI
              blnI
              avrII
              haeIII/palI
              stuI
              haeI
              mnlI maeI
       mnlI
  351 AGGAGGCTTT TTTGGAGGCC TAGGCTTTTG CAAAAAGCTA GCTTATCCGG
      TCCTCCGAAA AAACCTCCGG ATCCGAAAAC GTTTTTCGAT CGAATAGGCC tfiI
                       hinFI
       scrFI           aciI
       nciI            thaI                                    aciI
       mspI            fnuDII/mvnI
       hpaII           bstUI                           maeII   rsaI
       dsaV            bsh1236I                        maeIII  csp6I  scfI
       cauII
  401 CCGGGAACGG TGCATTGGAA CGGGGATTCC CCGTGCCAAG AGTGACGTAA GTACCGCCTA TAGAGGCATA
      GGCCCTTGCC ACGTAACCTT GCCCCTAAGG GGCACGGTTC TCACTGCATT CATGGCGGAT ATCTCGCTAT
                                                              ^splice donor fnu4HI
              bbvI
              nspBII                                                   pflMI
              aciI       nlaIII taqI                       sfaNI       bslI
       mnlI
  471 AGAGGATTTT ATCCCCGCTG CCATCATGGT TCGACCATTG AACTGCATCG TCGCCGTGTC CCAAAATATG
      TCTCCTAAAA TAGGGGCGAC GGTAGTACCA AGCTGGTAAC TTGACGTAGC AGCGGCACAG GGTTTATAC
                       DHFR ATG^
```

```
                                                          haeIII/palI
                                                          haeI
                                                  scrFI
                                                  mvaI          bsrBI
                                                  ecoRII
                                                  dsaV
                                                  bstNI   aciI
                                                  apyI[dcm+]          xmnI              rsaI
                                 bsmAI                               asp700             csp6I
                                 bsaI    bsaJI  mnlI  ddeI                               scaI
541 GGGATTGGCA AGAACGGAGA CCTACCCTGG CCTCCGCTCA GGAACGAGTT CAAGTACTTC CAAAGAATGA
    CCCTAACCGT TCTTGCCTCT GGATGGGACC GGAGGCGAGT CCTTGCTCAA GTTCATGAAG GTTTCTTACT eco57I                                                          scrFI
              mboII                                                           mvaI
              earI/ksp632I                              tfiI                  ecoRII
              mnlI                              alwNI   hinfI  hphI           dsaV
                                                                              bstNI
                                                                              apyI[dcm+]                ddeI
                                                                                      sexAI
611 CCACAACCTC TTCAGTGGAA GGTAAACAGA ATCTGGTGAT TATGGGTAGG AAAACCTGGT TCTCCATTCC
    GGTGTTGGAG AAGTCACCTT CCATTTGTCT TAGACCACTA ATACCCATCC TTTTGGACCA AGAGGTAAGG tfiI    tru9I       tru9I
       hinfI   mseI        mseI     ddeI
           mboII taqI    ahaIII/draI asel/asnI/vspI                           bslI    mnlI
681 TGAGAAGAAT CGACCTTTAA AGGACAGAAT TAATATAGTT CTCAGTAGAG AACTCAAAGA ACCACCACGA
    ACTCTTCTTA GCTGGAAATT TCCTGTCTTA ATTATATCAA GAGTCATCTC TTGAGTTTCT TGGTGGTGCT
```

FIG._16E

```
     sstI
     sacI
     hgiJII
     hgiAI/aspHI
     ecl136II
     bsp1286
     bsiHKAI
     bmyI                                    tru9I              mspI
     banII                                   aflII/bfrI         hpaII
     aluI          bstXI    fokI sfaNI mseI                     bsaWI                    haeIII/palI
                                                                                         haeI
751  GGAGCTCATT TTCTTGCCAA AAGTTTGGAT GATGCCTTAA GACTTATTGA ACAACCGGAA TTGGCAAGTA
     CCTCGAGTAA AAGAACGGTT TTCAAACCTA CTACGGAATT CTGAATAACT TGTTGGCCTT AACCGTTCAT scrFI              scrFI
                                            mvaI                    mvaI
                                            ecoRII             ecoRII
                                            dsaV          tfiI dsaV
                                            bstNI         nlaIII            bstNI   ddeI
                  mnlI                      apyI[dcm+]    hinfI apyI[dcm+]
     accI nlaIII
821  AAGTAGACAT GGTTTGGATA GTCGGAGGCA GTTCTGTTTA CCAGGAAGCC ATGAATCAAC CAGGCCACCT
     TTCATCTGTA CCAAACCTAT CAGCCTCCGT CAAGACAAAT GGTCCTTCGG TACTTAGTTG GTCCGGTGGA
```

FIG._16F

```
                                                            nlaIII
                                                            sau3AI
                                                            mboI/ndeII[dam-]
                                                            dpnI[dam+]                                                    maeII
                                                            dpnII[dam-]                                                   aflIII
        pleI                                                                apoI              maeIII
        hinfI           maeIII  alwI[dam-]
891 TAGACTCTTT GTGACAAGGA TCATGCAAGGA ATTTGAAAGT GACACGTTTT TCCCAGAAAT TGATTTGGGG
    ATCTGAGAAA CACTGTTCCT AGTACGTTCCT TAAACTTTCA CTGTGCAAAA AGGGTCTTTA ACTAAACCCC hgaI
                                         hinlI/acyI
                                         ahaII/bsaHI
                                   scrFI
                                   mvaI        mnlI
                                   ecoRII
                                   dsaV
                                   bstNI          ecoNI
                                   apyI[dcm+]          mnlI
                                   bsaJI       bslI ddeI
961 AAATATAAAC CTCTCCCAGA ATACCCAGGC GTCCTCTCTG
    TTTATATTTG GAGAGGGTCT TATGGGTCCG CAGGAGAGAC
         mnlI
```

FIG._16G

```
     scrFI
     mvaI
     ecoRII
     dsaV
     bstNI
     apyI[dcm+]
    sau96I
    avaII                                                                               sfaNI
    asuI   mnlI      sfaNI              accI    mboII                                   mboII
1001 AGGTCCAGGA GGAAAAAGGC ATCAAGTATA AGTTTGAAGT CTACGAGAAG AAAGACTAAC AGGAAGATGC
     TCCAGGTCCT CCTTTTTCCG TAGTTCATAT TCAAACTTCA GATGCTCTTC TTTCTGATTG TCCTTCTACG
                                                                   ^END DHFR nlaIII
                                                      styI
                                                      ncoI
                                                      dsaI
                              ppuI0I                  bsaJI
                   mnlI  aluI nsiI/avaIII ATGCATTTTT ATAAGACCAT GGGACTTTTG
1071 TTTCAAGTTC TCTGCTCCCC TCCTAAAGCT ATGCATTTTT ATAAGACCAT GGGACTTTTG
     AAAGTTCAAG AGACGAGGGG AGGATTTCGA TACGTAAAAA TATTCTGGTA CCCTGAAAAC
```

FIG._16H

```
                styI                                                                        sau96I
                bsaJI                                                                       avaII
      sau3AI           fnu4HI                                                               asuI
      mboII/ndeII[dam-]  aciI                                                               scrFI
      dpnI[dam+]        thaI                                                                mvaI
      dpnII[dam-]       fnuDII/mvnI  tru9I                                                  ecoRII
      alwI[dam-]        bstUI        mseI                                                   dsaV
      bstYI/xhoII       bsh1236I     aseI/asnI/vspI                                         bstNI
                                                                                            apyI[dcm+]
                                                                                     bslI  bsaJI
1131 CTGGCTTTAG ATCCCCCTTGG CTTCGTTAGA ACGCGGCTAC AATTAATACA TAACCTTATG TATCATACAC
     GACCGAAATC TAGGGGAACC GAAGCAATCT TGCGCCGATG TTAATTATGT ATTGGAATAC ATAGTATGTG maeIII
              hphI   scfI      fokI
1201 ATACGATTTA GGTGACACTA TAGATAACAT CCACTTTGCC TTTCTCTCCA CAGGTGTCCA CTCCCAGGTC
     TATGCTAAAT CCACTGTGAT ATCTATTGTA GGTGAAACGG AAAGAGAGGT GTCCACAGGT GAGGGTCCAG
```

FIG._16I

```
                                                             scrFI
                                                             nciI
                                                             mspI
                                                             hpaII
                                                             dsaV
                                                             xmaI/pspAI
                                                             smaI
                                                             scrFI
                                                             nciI
                                                             dsaV
                                                             cauII
                                                             bsaJI
                                                             avaI
                                                       sau3AI
                                                       mboI/ndeII[dam-]
                                                       dpnI[dam+]
                                                       dpnII[dam-]
                                                  nlaIV cauII
                                                  bstYI/xhoII
                                                  bamHI bsaJI
                                       taqI rmaI  maeI alwI[dam-]
                                  pleI sall       alwI[dam-]
                                  hinfI hincII/hindII alwI[dam-]
                scfI              accI xbaI mnlI bsaJI
         aluI   pstI
         hindIII bspMI
   mnlI  ddeI  bsgI
   bsaJI
1271 CAACTGCACC TCGGTTCTAA GCTTCTGCAG GTCGACTCTA GAGGATCCCC
     GTTGACGTGG AGCCAAGATT CGAAGACGTC CAGCTGAGAT CTCCTAGGGG
```

FIG._16J

```
                                                    sau96I
                                 aciI               haeIII/palI
                                 fnu4HI             asuI
                                 bglI     nlaIII
                                 sfiI     styI
                                 eaeI     ncoI                                                        aluI
                                 cfrI     dsaI                                                        fnu4HI
          ecoRI   taqI haeIII/palI                                                              bbvI         maeIII
          apoI   claI/bspI06 bsaJI                                                                                                     rmaI
1321 GGGGAATTCA ATCGATGGCC GCCATGGCCC AACTTGTTTA TTGCAGCTTA TAATGGTTAC AAATAAAGCA
     CCCCTTAAGT TAGCTACCGG CGGTACCGGG TTGAACAAAT AACGTCGAAT ATTACCAATG TTTATTTCGT
                                                 ^sv40 sfaNI                                                                                  bsmI maeI
          apoI
1391 ATAGCATCAC AAATTTCACA AATAAAGCAT TTTTTTCACT GCATTCTAGT TGTGGTTTGT CCAAACTCAT
     TATCGTAGTG TTTAAAGTGT TTATTTCGTA AAAAAAGTGA CGTAAGATCA ACACCAAACA GGTTTGAGTA
```

FIG._16K

```
                                              sau3AI
                                              mboI/ndeII[dam-]
                                              dpnI[dam+]
                                              dpnII[dam-]
                                              pvuI/bspCI
                                              mcrI
                                              taqI[dam-]    tru9I
                                              claI/bsp106[dam-]
                                              sau3AI         mseI
                                              mboI/ndeII[dam-]
                                              dpnI[dam+] xmnI
                             nlaIII   alwI[dam-]  dpnII[dam-]    aseI/asnI/vspI
                                                               asp700
1461 CAATGTATCT TATCATGTCT GGATCGATCG GGAATTAATT
     GTTACATAGA ATAGTACAGA CCTAGCTAGC CCTTAATTAA
                                                 sv40 origin^ rsaI
                                                                      csp6I
                                                                      nlaIV
                                                                      kpnI
                                                                      hgiCI
                                                                      banI
                                                        asp718        mnlI
                                                        acc65I   ddeI aciI
1501 CGGCGCAGCA CCATGGCCTG AAATAACCTC TGAAAGAGGA ACTTGGTTAG GTACCTTCTG AGGCGGAAAG
     GCCGCGTCGT GGTACCGGAC TTTATTGGAG ACTTTCTCCT TGAACCAATC CATGGAAGAC TCCGCCTTTC
              haeIII/palI               mnlI     mnlI
             haeI
           styI
          ncoI
      fnu4HI dsaI
      bbvI  bsaJI
     hinPI   nlaIII
     hhaI/cfoI
```

FIG._16L

```
                aluI
                pvuII
                nspBII
1571 AACCAGCTGT GGAATGTGTG TCAGTTAGGG TGTGGAAAGT CCCCAGGCTC CCCAGCAGGC AGAAGTATGC
     TTGGTCGACA CCTTACACAC AGTCAATCCC ACACCTTTCA GGGGTCCGAG GGGTCGTCCG TCTTCATACG
                                                     scrFI               nlaIV
                                                     mvaI
                                                     ecoRII
                                                     dsaV
                                                     bstNI
                                                     apyI[dcm+]
                                                     bsaJI sfaNI                      scrFI     scrFI
        ppu10I                     mvaI
     nsiI/avaIII              ecoRII  ecoRII
     nlaIII                   dsaV    dsaV
        sphI                          bstNI                                          nlaIV
        nspI                          apyI[dcm+]                            bstNI
        nspHI                         sexAI                                 apyI[dcm+]
                                                                            bsaJI
1641 AAAGCATGCA TCTCAATTAG TCAGCAACCA GGTGTGGAAA GTCCCCAGGC TCCCCAGCAG GCAGAAGTAT
     TTTCGTACGT AGAGTTAATC AGTCGTTGGT CCACACCTTT CAGGGGTCCG AGGGGTCGTC CGTCTTCATA
                                                                                mvaI sfaNI
        ppu10I
     nsiI/avaIII
     nlaIII
        sphI
        nspI
        nspHI                             aciI                    aciI       aciI      aciI
                                                                             fokI
1711 GCAAAGCATG CATCTCAATT AGTCAGCAAC CATAGTCCCG CCCCTAACTC CGCCATCCC GCCCCTAACT
     CGTTTCGTAC GTAGAGTTAA TCAGTCGTTG GTATCAGGGC GGGGATTGAG GCGGTAGGG CGGGGATTGA
```

FIG._16M

```
                                         nlaIII
                                         styI
                                         ncoI
                              bslI dsaI                                mnlI
       bsrI                   acil bsaJI GGCTGACTAA TTTTTTTTAT TTATGCAGAG
     asiI      aciI
1781 CCGCCCAGTT CCGCCCATTC TCCGCCCCAT GGCTGACTAA TTTTTTTTAT TTATGCAGAG
     GGCGGGTCAA GGCGGGTAAG AGGCGGGGTA CCGACTGATT AAAAAAAATA AATACGTCTC styI
                                                                    bsaJI
             fnu4HI                                                 blnI
             bglI                                                   avrII
             sfiI                                             haeIII/palI
             haeIII/palI                                      stuI
           mnlI mnlI      ddeI                       mnlI     haeI
     haeIII/palI bsaJI mnlI    aluI             mnlI          mnlI
     bsaJI aciI      haeIII/palI
1841 GCCGAGGCCG CCTCGGCCG CCTCGGCCTC TGAGCTATTC CAGAAGTAGT GAGGAGGCTT TTTTGGAGGC
     CGGCTCCGGC GGAGCCGGAG ACTCGATAAG GTCTTCATCA CTCCTCCGAA AAAACCTCCG
```

FIG. 16N

```
                                                     hinPI
                                    aciI              hhaI/cfoI
                                    haeIII/palI      thaI
                              mcrI                                       bspMI
                              eagI/xmaIII/eclXI  fnuDII/mvnI
                                                 bstUI                   scfI
                        taqI  eaeI               hinPI                   pstI
                        xhoI  notI               hhaI/cfoI  tru9I        ahaIII/draI
                        paeR7I cfrI  tru9I       ascI                    bsgI
                        avaI  fnu4HI pacI        msel trug1 bsh1236I msel sse8387I
                  mnlI  aciI  msel tru9I bsh1236I msel bssHII swaI
            aluI maeIII bsrBI fnu4HI     msel bssHII  CGCCATTTAA ATCCTGCAGG
     rmaI                                                                        scrFI
     maeI                                                                        mvaI
                                                                                 ecoRII
                                                                                 dsaV
                                                                                 bstNI
                       haeIII/palI                                               apyI[dcm+]           tru9I
                       eaeI                                                      bsaJI  maeIII        msel
            maeIII     cfrI              maeIII      bsrI
            aluI       bsrI              maeII       bsrI
```

1901 CTAGGCTTTT GCAAAAAGCT GTTACCTCGA GCGGCCGCTT AATTAAGGCG CGCCATTTAA ATCCTGCAGG
     GATCCGAAAA CGTTTTTCGA CAATGGAGCT CGCCGGCGAA TTAATTCCGC GCGGTAAATT TAGGACGTCC
     ^start pUC118
                ^linearization linker inserted into HpaI site 1971 TAACAGCTTG GCACTGGCCG TCGTTTTACA ACGTCGTGAC TGGGAAAACC CTGGCGTTAC CCAACTTAAT GGTTGAATTA
     ATTGTCGAAC CGTGACCGGC AGCAAAATGT TGCAGCACTG ACCCTTTTGG GACCGCAATG GGTTGAATTA

FIG._160

```
                                                               sau3AI
                                                          sau96I   mboI/ndeII[dam-]
                                                     haeIII/palI
                                                     asuI   dpnI[dam+]
                                        aluI          mnlI      dpnII[dam-]
                                        pvuII         mboII  aciI  pvuI/bspCI
              fnu4HI                    nspBII        earI/ksp632I     mcrI
              bbvI    fokI
2041 CGCCTTGCAG CACATCCCCC CTTCGCCAGC TGGCGTAATA GCGAAGAGGC CCGCACCGAT
     GCGGAACGTC GTGTAGGGGG GAAGCGGTCG ACCGCATTAT CGCTTCTCCG GGCGTGGCTA
                                hinPI
                                hhaI/cfoI
                                nlaIV
                                narI
                                kasI
                                hinlI/acyI
                                hgiCI
                                haeII    aciI
                                banI     sfaNI
                                ahaII/bsaHI                         sfaNI
                       bglI                       GCCTGATGCG GTATTTCTC CTTACGCATC
2101 CGCCCTTCCC AACAGTTGCG TAGCCTGAAT GGGCGAATGGC GCCTGATGCG GTATTTCTC CTTACGCATC
     GCGGGAAGGG TTGTCAACGC ATCGGACTTA CCGCTTACCG CGGACTACGC CATAAAAGAG GAATGCGTAG
```

FIG._16P

```
                                                                     hinPI
                                                                     thaI
                                                                     fnuDII/mvnI
                                                                     bstUI scfI          hinPI
                                                                     bsh1236I            hhaI/cfoI
                                                     rsaI hhaI/cfoI                      fnu4HI
          aciI                                       csp6I      bslI        aciI
     aciI       fnu4HI       maeII
2171 TGTGCGGGTAT TTCACACCGC ATACGTCAAA GCAACCATAG TACGCGCCCT GTAGCGGCGC
     ACACGCCCATA AAGTGTGGCG TATGCAGTTT CGTTGGTATC ATGCGCGGGA CATCGCCGCG fnu4HI
          thaI                                                                   hinPI
          fnuDII/mvnI                                                            hhaI/cfoI
          bstUI           thaI                                        rmaI
     hinPI aciI          fnuDII/mvnI                                  hinPI          haeII
     hhaI/cfoI           bstUI                                        hhaI/cfoI      bsrBI
     tru9I aciI          bsh1236I      aciI                           haeII maeI     aciI
     mseI bsh1236I       maeIII bbvI   maeIII
2231 ATTAAGCGCG GCGGGTGTGG TGGTTACGCG CAGCGTGACC GCTACACTTG CCAGCGCCCT AGCGCCCGCT
     TAATTCGCGC CGCCCACACC ACCAATGCGC GTCGCACTGG CGATGTGAAC GGTCGCGGGA TCGCGGGCGA nlaIV
                                                                          hgiJII
                                                                          bsp1286
                                         mspI                             bmyI
                                         hpaII                            banII
                          mboII          naeI
                                                         maeII cfr10I     aluI
2301 CCTTTCGCTT TCTTCCCTTC CTTTCTCGCC ACGTTCGCCG GCTTTCCCCG TCAAGCTCTA AATCGGGGGC
     GGAAAGCGAA AGAAGGGAAG GAAAGAGCGG TGCAAGCGGC CGAAAGGGGC AGTTCGAGAT TTAGCCCCCG
```

FIG._16Q

```
                                                       mnlI
                                                       nlaIV
                                                       hgiCI
                                                       banI taqI                            hphI
              nlaIV
2371 TCCCTTTAGG GTTCCGATTT AGTGCTTTAC GGCACCTCGA CCCCAAAAAA CTTGATTTGG
     AGGGAAATCC CAAGGCTAAA TCACGAAATG CCGTGGAGCT GGGGTTTTTT GAACTAAACC maeII pleI
              maeII  haeIII/paII                              drdI hinfI maeII
           draIII  sau96I                                bsII
           bsaAI   asuI                                  bsII aval
2401 GTGATGGTTC ACGTAGTGGG CCATCGCCCT GATAGACGGT TTTTCGCCCT TTGACGTTGG AGTCCACGTT
     CACTACCAAG TGCATCACCC GGTAGCGGGA CTATCTGCCA AAAAGCGGGA AACTGCAACC TCAGGTGCAA tru9I
        mseI  pleI                       bsrI
2501 CTTTAATAGT GGACTCTTGT TCCAAACTGG AACCCTATCT CGGGCTATTC TTTTGATTTA
     GAAATTATCA CCTGAGAACA AGGTTTGACC TTGGGATAGA GCCCGATAAG AAAACTAAAT tru9I
                         tru9I                                       mseI
                haeIII/paII mseI              alul  mseI    apoI
2571 TAAGGGATTT TGCCGATTTC GGCCTATTGG TTAAAAAATG AGCTGATTTA ACAAAAATTT
     ATTCCCTAAA ACGGCTAAAG CCGGATAACC AATTTTTTAC TCGACTAAAT TGTTTTTAAA
```

FIG. 16R

```
                                              hgiAI/aspHI
                                              bsp1286
                                              bsiHKAI
      thaI                        maeII        bmyI   ddeI
      fnuDII/mvnI                 psp1406I     apaLI/snoI  rsaI
      apoI       tru9I            tru9I        alw44I/snoI csp6I
      bstUI      tru9I            tru9I        alw44I/snoI csp6I
      bsh1236I msel     sspI msel
2631 AACGCGAATT TAACAAAAT ATTAACGTTT ACAATTTTAT GGTGCACTCT CAGTACAATC
     TTGCGCTTAA AATTGTTTTA TAATTGCAAA TGTTAAAATA CCACGTGAGA GTCATGTTAG bsrI         hinPI
                                                        maeIII       fnu4HI
                 fnu4HI    tru9I            maeII       nlaIII hhaI/cfoI
              sfaNI aciI   msel        aciI   bsaAI tth111I/aspI bbvI
2691 TGCTCTGATG CCGCATAGTT AAGCCAACTC CGCTATCGCT ACGTGACTGG GTCATGGCTG CGCCCCGACA
     ACGAGACTAC GGCGTATCAA TTCGGTTGAG GCGATAGCGA TGCACTGACC CAGTACCGAC GCGGGGCTGT sfaNI
                  hinPI                                     mspI
                  hhaI/cfoI                                 hpaII
                  thaI                                      scrFI
                  fnuDII/mvnI                               nciI
                  bstUI                                     dsaV fokI
              nspBII bsh1236I        drdI        cauII   aciI
     aciI     aciI hgaI                                                    aluI
2761 CCCGCCAACA CCCGCTGACG CGCCCTGACG GGCTTGTCTG CTCCCGGCAT CCGCTTACAG ACAAGCTGTG
     GGGCGGTTGT GGGCGACTGC GCGGGACTGC CCGAACAGAC GAGGGCCGTA GGCGAATGTC TGTTCGACAC
```

FIG._16S

```
           scrFI
           nciI
           mspI
           hpaII     nspI
           dsaV      nspHI
     esp3I      fnu4HI
     bsmAI      bbvI                                                                         thaI
     bslI  cauII aluI nlaIII  mnlI      hphI                                                 fnuDII/mvnI
                                                                                             bstUI
                                                                                             bsh1236I
2831 ACCGTCTCCG GGAGCTGCAT GTGTCAGAGG TTTTCACCGT CATCACCGAA ACGGCGGAGG CAGTATTCTT             hinPI
     TGGCAGAGGC CCTCGACGTA CACAGTCTCC AAAAGTGGCA GTAGTGGCTT TGCGCGCTCC GTCATAAGAA             hhaI/cfoI
                                                                                             thaI mnlI
                                                                                             fnuDII/mvnI
                                                                                             bstUI
                                                                                             bsh1236I
                        mnlI                                           nlaIII
                 haeIII/palI                                  tru9I rcaI
     mboII   sau96I                                           mseI bspHI
     bpuAI   asuI                                     hphI
     bbsI  eco0109I/draII
2901 GAAGACGAAA GGGCCTCGTG ATACGCCTAT TTTTATAGGT TAATGTCATG
     CTTCTGCTTT CCCGGAGCAC TATGCGGATA AAAATATCCA ATTACAGTAC
                                                                                    aciI
                                                                                    thaI
                                                                                    fnuDII/mvnI
                                                                                    bstUI
                      hinII/acyI                                                    bsh1236I
                      ahaII/bsaHI                                                   hinPI
                      aatII                                                         hhaI/cfoI
                ddeI maeII
2951 ATAATAAATGG TTTCTTAGAC GTCAGGTGGC ACTTTTCGGG GAAATGTGCG
     TATTATTACC AAAGAATCTG CAGTCCACCG TGAAAAGCCC CTTTACACGC
```

FIG._16T

```
                                                                               bsmAI
                                                                               rcaI
                                                                 bsrBI nlaIII
                                                                 aciI bspHI
3001 CGGAACCCCT ATTTGTTTAT TTTTCTAAAT ACATTCAAAT ATGTATCCGC TCATGAGACA ATAACCCTGA
     GCCTTGGGGA TAAACAAATA AAAAGATTTA TGTAAGTTTA TACATAGGCG AGTACTCTGT TATTGGGACT
                         sspI              mboII
                                           earI/ksp632I
3071 TAAATGCTTC AATAATATTG AAAAAGGAAG AGTATGAGTA TTCAACATTT CCGTGTCGCC CTTATTCCCT
     ATTTACGAAG TTATTATAAC TTTTTCCTTC TCATACTCAT AAGTTGTAAA GGCACAGCGG GAATAAGGGA
     fnu4HI                                       hphI              hphI         sfaNI
     aciI
3141 TTTTTGCGGC ATTTTGCCTT CCTGTTTTTG CTCACCCAGA AACGCTGGTG AAAGTAAAAG
     AAAAACGCCG TAAAACGGAA GGACAAAAAC GAGTGGGTCT TTGCGACCAC TTTCATTTTC
                     hgiAI/aspHI                                     sau3AI
                     bsp1286                                         mboI/ndeII[dam-]
                     bsiHKAI                                         dpnI[dam+]
           sau3AI                                                    dpnII[dam-]
           mboI/ndeII[dam-]                                          bstYI/xhoII
           dpnI[dam+] bmyI                                           alwI[dam-]   aciI
           dpnII[dam-]
           mboII[dam-]  apaLI/snoI        taqI              bsrI            nspBII
           eco57I       alw44I/snoI       maeIII
3201 ATGCTGAAGA TCAGTTGGGT GCACGAGTGG GTTACATCGA ACTGGATCTC AACAGCGGTA
     TACGACTTCT AGTCAACCCA CGTGCTCACC CAATGTAGCT TGACCTAGAG TTGTCGCCAT
```

FIG._16U

```
          sau3AI
          mboI/ndeII[dam-]                       maeII
          dpnI[dam+]                             psp1406I              hgiAI/aspHI
          dpnII[dam-]                            xmnI                  bsp1286  tru9I
          alwI[dam-]                             asp700                bsiHKAI  mseI
          bstYI/xhoII        mboII                                     bmyI     ahaIII/draI
3261 AGATCCTTGA GAGTTTTCGC CCCGAAGAAC GTTTTCCAAT GATGAGCACT TTTAAAGTTC
     TCTAGGAACT CTCAAAAGCG GGGCTTCTTG CAAAAGGTTA CTACTCGTGA AAATTTCAAG scrFI
                       aciI                      nciI
                       thaI                      mspI
                       fnuDII/mvnI               hpaII
                       bstUI                     dsaV
                       bsh1236I       hinlI/acyI                                    aciI
                       hinPI          hgaI cauII                bcgI  mcrI       fnu4HI
                       hhaI/cfoI      ahaII/bsaHI          AGAGCAACTC GGTCGCCGCA
3321 TGCTATGTGG CGCGGTATTA TCCCGTGATG ACGCCGGGCA AGAGCAACTC GGTCGCCGCA
     ACGATACACC GCGCCATAAT AGGGCACTAC TGCGGCCCGT TCTCGTTGAG CCAGCGGCGT rsaI
                                       csp6I   bsrI
                               ddeI    scaI hphI maeIII       sfaNI    fokI
3381 TACACTATTC TCAGAATGAC TTGGTTGAGT ACTCACCAGT CACAGAAAAG CATCTTACGG
     ATGTGATAAG AGTCTTACTG AACCAACTCA TGAGTGGTCA GTGTCTTTTC GTAGAATGCC
```

FIG._16V

```
                                                                              haeIII/palI
                                                                              eaeI
                                                                              cfrI
                                                                              fnu4HI
                                     fnu4HI                                   aciI
                                     bbvI          nlaIII
        nlaIII                                     CATGAGTGAT AACACTGCGG CCAACTTACT
3441 ATGGCATGAC AGTAAGAGAA TTATGCAGTG CTGCCATAAC CATGAGTGAT AACACTGCGG CCAACTTACT
     TACCGTACTG TCATTCTCTT AATACGTCAC GACGGTATTG GTACTCACTA TTGTGACGCC GGTTGAATGA sau96I
                              avaII                                           nlaIII
                              asuI                                            sau3AI maeIII
                    sau3AI                                                    mboI/ndeII[dam-]
                    mboI/ndeII[dam-]                                          dpnI[dam+]
                    dpnI[dam+]                                                dpnII[dam-]
                    dpnII[dam-]
                    pvuI/bspCI
             mcrI   mnlI         aluI    aciI              nlaIII  alwI[dam-]
3511 TCTGACAACG ATCGGAGGAC CGAAGGAGCT AACCGCTTTT TTGCACAACA TGGGGGATCA TGTAACTCGC
     AGACTGTTGC TAGCCTCCTG GCTTCCTCGA TTGGCGAAAA AACGTGTTGT ACCCCCTAGT ACATTGAGCG mspI
        sau3AI  nlaIV                                                         fnu4HI
        mboI/ndeII[dam-] aluI                                   maeIII  sfaNI bbvI
        dpnI[dam+]       hpaII
        dpnII[dam-]      bsaWI
3581 CTTGATCGTT GGGAACCGGA GCTGAATGAA GCCATACCAA ACGACGAGCG TGACACCACG ATGCCAGCAG
     GAACTAGCAA CCCTTGGCCT CGACTTACTT CGGTATGGTT TGCTGCTCGC ACTGTGGTGC TACGGTCGTC
```

```
                                                              mspI
                                                              hpaII
                       hinPI                                  scrFI
                       hhaI/cfoI                              nciI
                       mstI                            aluI   dsaV
                       aviII/fspI      bsrI            rmaI   cauII
              maeII              tru9I                 maeI
              psp1406I           mseI
3651 CAATGGCAAC AACGTTGCGC AAACTATTAA CTGGCGAACT ACTTACTCTA GCTTCCCGGC
     GTTACCGTTG TTGCAACGCG TTTGATAATT GACCGCTTGA TGAATGAGAT CGAAGGGCCG bglI
                                                            sau96I
                                  sau96I                    haeIII/palI
     tru9I      fokI              avaII           hinPI     asuI     mspI
     mseI    bsrI    aciI         asuI            hhaI/cfoI          hpaII
     aseI/asnI/vspI mnlI
3711 AACAATTAAT AGACTGGATG GAGGCGGATA AAGTTGCAGG ACCACTTCTG CGCTCGGCCC TTCCGGCTGG
     TTGTTAATTA TCTGACCTAC CTCCGCCTAT TTCAACGTCC TGGTGAAGAC GCGAGCCGGG AAGGCCGACC mspI                  thaI
                           hpaII                 fnuDII/mvnI
                           cfr10I                bstUI
                      nlaIV hphI          bsmAI aciI              fnu4HI
                    gsuI/bpmI             bsaI bsh1236I           bbvI
3781 CTGGTTTATT GCTGATAAAT CTGGAGCCGG TGAGCGTGGG TCTCGCGGTA TCATTGCAGC
     GACCAAATAA CGACTATTTA GACCTCGGCC ACTCGCACCC AGAGCGCCAT AGTAACGTCG
```

```
           sau96I
           asuI
           nlaIV                                                                          pleI
     bsrI haeIII/palI  mnlI                                            eam1105I           hinfI
3841 ACTGGGGCCA GATGGTAAGC CCTCCCGTAT CGTAGTTATC TACACGACGG GGAGTCAGGC
     TGACCCCGGT CTACCATTCG GGAGGGCATA GCATCAATAG ATGTGCTGCC CCTCAGTCCG ddeI
                              sau3AI           nlaIV
                              mboI/ndeII[dam-]
                              dpnI[dam+]       hgiCI        tru9I
                         foKI dpnII[dam-]      banI mnlI    mseI
3901 AACTATGGAT GAACGAAATA GACAGATCGC TGAGATAGGT GCCTCACTGA TTAAGCATTG
     TTGATACCTA CTTGCTTTAT CTGTCTAGCG ACTCTATCCA CGGAGTGACT AATTCGTAAC tru9I
                                                            mseI           tru9I
     maeIII                                                 ahaIII/draI    mseI
3961 GTAACTGTCA GACCAAGTTT ACTCATATAT ACTTTAGATT GATTAAAAC TTCATTTTTA
     CATTGACAGT CTGGTTCAAA TGAGTATATA TGAAATCTAA CTAAATTTG AAGTAAAAAT
     rmaI       sau3AI
     sau3AI hphI  mboI/ndeII[dam-]
     mboI/ndeII[dam-]
     dpnI[dam+]   dpnI[dam+]
     dpnII[dam-]  dpnII[dam-]
     tru9I bstYI/xhoII alwI[dam-]                           nlaIII            maeII
     mseI  alwI[dam-] bstYI/xhoII                           rcaI              tru9I
     ahaIII/draI maeI  mboII[dam-]                          bspHI             mseI
4021 ATTTAAAAGG ATCTAGGTGA AGATCCTTTT TGATAATCTC ATGACCAAAA TCCCTTAACG TGAGTTTTCG
     TAAATTTTCC TAGATCCACT TCTAGGAAAA ACTATTAGAG TACTGGTTTT AGGGAATTGC ACTCAAAAGC
```

FIG._16Y

```
                                                      sau3AI
                                                      mboI/ndeII[dam-]
                                                      dpnI[dam+]      sau3AI
                                                      dpnII[dam-]  mboI/ndeII[dam-]
                                                      bstYI/xhoII     dpnI[dam+]
                                                                      dpnII[dam-]
                                      sau3AI    alwI[dam-]       alwI[dam-]
                                      mboI/ndeII[dam-]
                                      dpnI[dam+] mboI[dam-]
                                      dpnII[dam-]                        bstYI/xhoII
                hgaI
                ddeI
4091    TTCCACTGAG CGTCAGACCC CGTAGAAAAG ATCAAAGGAT CTTCTTGAGA TCCTTTTTTT
        AAGGTGACTC GCAGTCTGGG GCATCTTTTC TAGTTTCCTA GAAGAACTCT AGGAAAAAAA thaI
        fnuDII/mvnI
        bstUI
        bsh1236I
        hinPI       fnu4HI                          aciI
        hhaI/cfoI   bbvI              aciI         nspBII
4151    CTGCGGCGTAA TCTGCTGCTT GCAAACAAAA AAACCACCGC TACCAGCGGT GGTTTGTTTG
        GACGCCGCATT AGACGACGAA CGTTTGTTTT TTTGGTGGCG ATGGTCGCCA CCAAACAAAC sau3AI
        mboI/ndeII[dam-]
        dpnI[dam+]
        dpnII[dam-]
        alwI[dam-]
        mspI                                                            hinPI
        hpaII    aluI              bsrI                                 hhaI/cfoI
                             maeIII    eco57I
4211    CCGGATCAAG AGCTACCAAC TCTTTTTCCG AAGGTAACTG GCTTCAGCAG AGGCAGATA CCAAATACTG
        GGCCTAGTTC TCGATGGTTG AGAAAAAGGC TTCCATTGAC CGAAGTCGTC TCCGTCTAT GGTTTATGAC
```

FIG. 16Z-1

```
             rmaI              haeIII/palI
                mael        bsll     haeI              scfI      aciI           mnlI
      4281 TCCTTCTAGT GTAGCCGTAG TTAGGCCACC ACTTCAAGAA CTCTGTAGCA CCGCCTACAT ACCTCGCTCT
           AGGAAGATCA CATCGGCATC AATCCGGTGG TGAAGTTCTT GAGACATCGT GGCGGATGTA TGGAGCGAGA scrFI
                                                                           nciI
                                          fnu4HI                           mspI
                                  alwNI   bbvI                             hpaII
                             bsrI fnu4HI bbvI    bsrI                      dsaV    pleI
                              maeIII bbvI bsrI                             cauII   hinfI
      4351 GCTAATCCTG TTACCAGTGG CTGCTGCCAG TGGCCGATAAG TCGTGTCTTA CCGGGTTGGA CTCAAGACGA
           CGATTAGGAC AATGGTCACC GACGACGGTC ACCGCTATTC AGCACAGAAT GGCCCAACCT GAGTTCTGCT hgiAI/aspHI
                             nspBII                                 bsp1286
                       mspI  fnu4HI                                 bsiHKAI
                       hpaII bbvI mcrI                              bmyI
                       bsaWI hinPI aciI                             apaLI/snoI
                       maeIII hhaI/cfoI                             alw44I/snoI   aluI
      4421 TAGTTACCGG ATAAGGCGCA GCGGTCGGGC CGCCAGCCCG ACTTGCCCCC GTTCGTGCAC ACAGCCCAGC TTGGAGCGAA
           ATCAATGGCC TATTCCGCGT CGCCAGCCCG CGGTCGGGC TGAACGGGGG CAAGCACGTG TGTCGGGTCG AACCTCGCTT hinPI
                              ddeI      scfI                               hhaI/cfoI
                                                                           haeII
      4491 CGACCTACAC CGAACTGAGA TACCTACAGC GTGAGCATTG AGAAAGCGCC ACGCTTCCCG AAGGGAGAAA
           GCTGGATGTG GCTTGACTCT ATGGATGTCG CACTCGTAAC TCTTTCGCGG TGCGAAGGGC TTCCCTCTTT
```

FIG._16Z-2

```
                                                                                           scrFI
                                                                                           mvaI
                                                                                           ecoRII    mvaI
                                                                                           dsaV      ecoRII
                                                                                           bstNI
                                                                   hinPI mnlI              bsaJI
             mspI                                                  hhaI/cfoI  aluI apyI[dcm+]
             hpaII                                                 
             bslI       fnu4HI
      aciI   bsaWI      aciI
4561  GGCGGACAGG TATCCGGTAA GCGGCAGGGT CGGAACAGGA GAGCGCACGA GGGAGCTTCC AGGGGAAAC
      CCGCCTGTCC ATAGGCCATT CGCCGTCCCA GCCTTGTCCT CTCGCGTGCT CCCTCGAAGG TCCCCCTTTG scrFI dsaV
      bstNI                                                                    taqI
      apyI[dcm+]                       mnlI  drdI  hgaI              sfaNI
4631  GCCTGGTATC TTTATAGTCC TGTCGGGTTT CGCCACCTCT GACTTGAGCG TCGATTTTTG TGATGCTCGT
      CGGACCATAG AAATATCAGG ACAGCCCAAA GCGGTGGAGA CTGAACTCGC AGCTAAAAAC ACTACGAGCA haeIII/palI
                                                              fnu4HI
                                                              aciI
                                                              thaI bslI
                                                              fnuDII/mvnI
                                                              bstUI
             nlaIV                                            bsh1236I
             aciI
4701  CAGGGGGGCG GAGCCTATGG AAAAACGCCA GCAACGCGGC
      GTCCCCCCGC CTCGGATACC TTTTTGCGGT CGTTGCGCCG
```

FIG. 16Z-3

```
                       haeIII/palI                                                                     tfiI
         scrFI                                                                                         hinfI
         mvaI bslI
         ecoRII
         dsaV                         nlaIII
         bstNI                              nspI
         apyI[dcm+]         haeIII/palI     nspHI
      nlaIV haeI           haeI             aflIII
4741 CTTTTTACGG TTCCTGGCCT TTTGCTGGCC TTTGCTCTCAC ATGTTCTTTC CTGCGTTATC CCCTGATTCT
     GAAAAATGCC AAGGACCGGA AAACGACCGG AAAACGAGTG TACAAGAAAG GACGCAATAG GGGACTAAGA fnu4HI
                                                                      bbvI
                                          bsrBI      aciI   fnu4HI        mcrI
                    aciI       alul    GCTGATACCG CTCGCCGCAG CCGAACGACC
4811 GTGGATAACC GTATTACCGC CTTTGAGTGA GCTGATACCG CTCGCCGCAG CCGAACGACC
     CACCTATTGG CATAATGGCG GAAACTCACT CGACTATGGC GAGCGGCGTC GGCTTGCTGG hinPI
                                           haeII
            fnu4HI                     sapI hhaI/cfoI
            bbvI pleI                  mboII                                   mnlI
         hinPI hinfI          mnlI aciI earI/ksp632I                        aciI
         hhaI/cfoI
4871 GAGGCAGCG AGTCAGTGAG CGAGGAAGCG GAAGAGCGCC CAATACGCAA ACCGCCTCTC
     CTCCGTCGC TCAGTCACTC GCTCCTTCGC CTTCTCGCGG GTTATGCGTT TGGCGGAGAG
```

FIG. 16Z-4

```
      thaI
      fnuDII/mvnI
      bstUI
      bsh1236I
      hinPI
      hhaI/cfoI
      thaI
      fnuDII/mvnI
      bstUI
      bsh1236I haeIII/palI          tru9I    aluI
      bslI    eaeI  tfiI  aseI/asnI/vspI   pvuII                          bsrI       aciI
      aciI    cfrI  hinfI msel  nspBII                                                                                                      
4931  CCCGCGCGTT GGCCGATTCA TTAATCCAGC TGGCACGACA GTTTCCCGA CTGGAAAGCG
      GGGCGCGCAA CCGGCTAAGT AATTAGGTCG ACCGTGCTGT CCAAAGGGCT GACCTTTCGC scrFI
                                                                              mvaI
                                                                              ecoRII
                                                                              dsaV
                                                                      nlaIV   bstNI
                          tru9I                                       hgiCI   apyI[dcm+]
              hinPI       mseI    maeIII                              banI    bsaJI
              hhaI/cfoI   aseI/asnI/vspI  mnlI
4991  GGCAGTGAGC GCAACGCAAT TAATGTGAGT TACCTCACTC ATTAGGCACC CCAGGCTTTA CACTTTATGC
      CCGTCACTCG CGTTGCGTTA ATTACACTCA ATGGAGTGAG TAATCCGTGG GGTCCGAAAT GTGAAATACG
```

FIG._16Z-5

```
       mspI                              aciI                      alul        nlaIII
        hpaII                     bsrBI
5061 TTCCGGCTCG TATGTTGTGT GGAATTGTGA GCGGATAACA ATTTCACACA GGAAACAGCT ATGACCATGA.
     AAGGCCGAGC ATACAACACA CCTTAACACT CGCCTATTGT TAAAGTGTGT CCTTTGTCGA TACTGGTACT tru9I
            mseI
            aseI/asnI/vspI
              xmnI
              asp700
5131 TTACGAATTA A
     AATGCTTAAT T >length: 5141
```

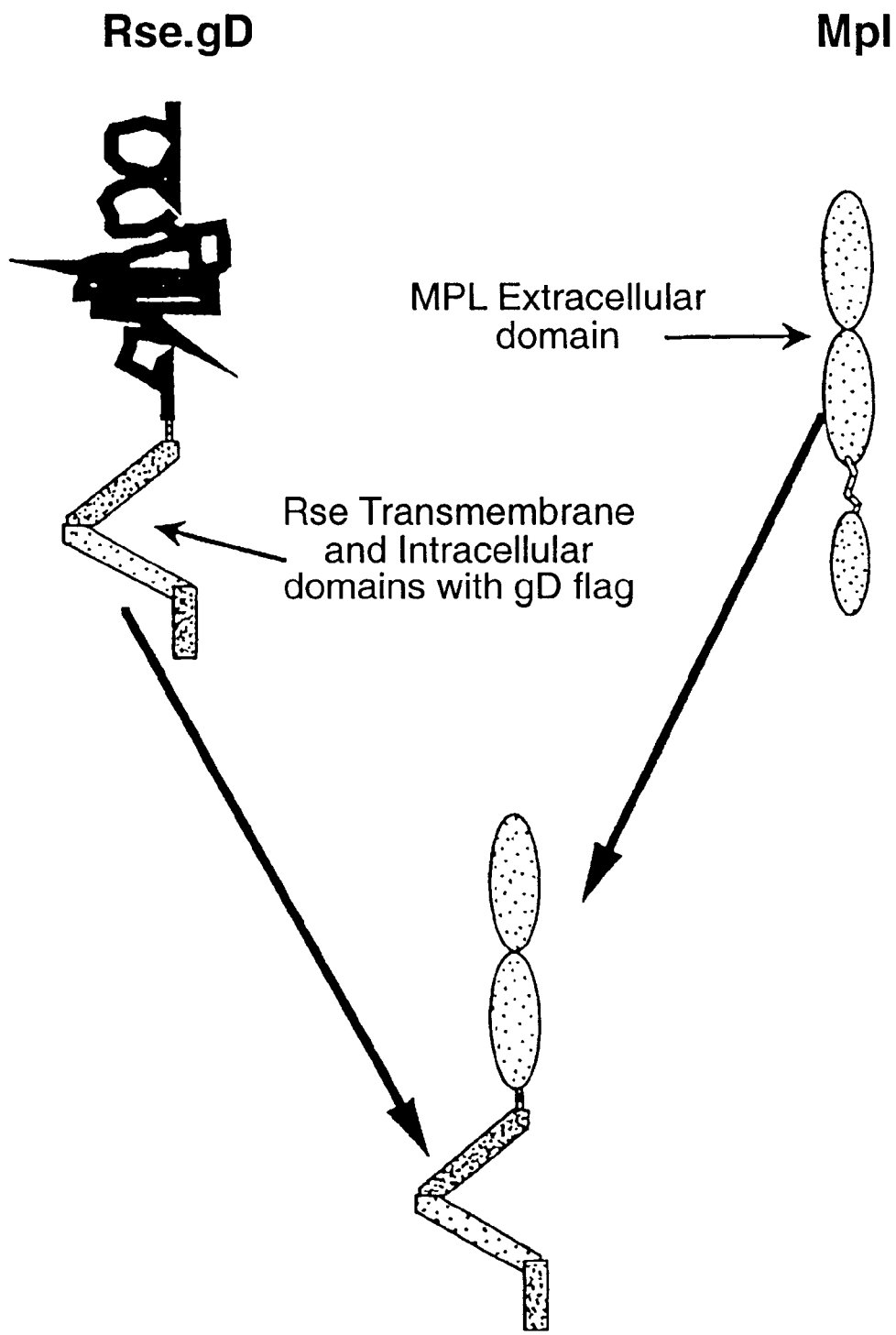
FIG._17

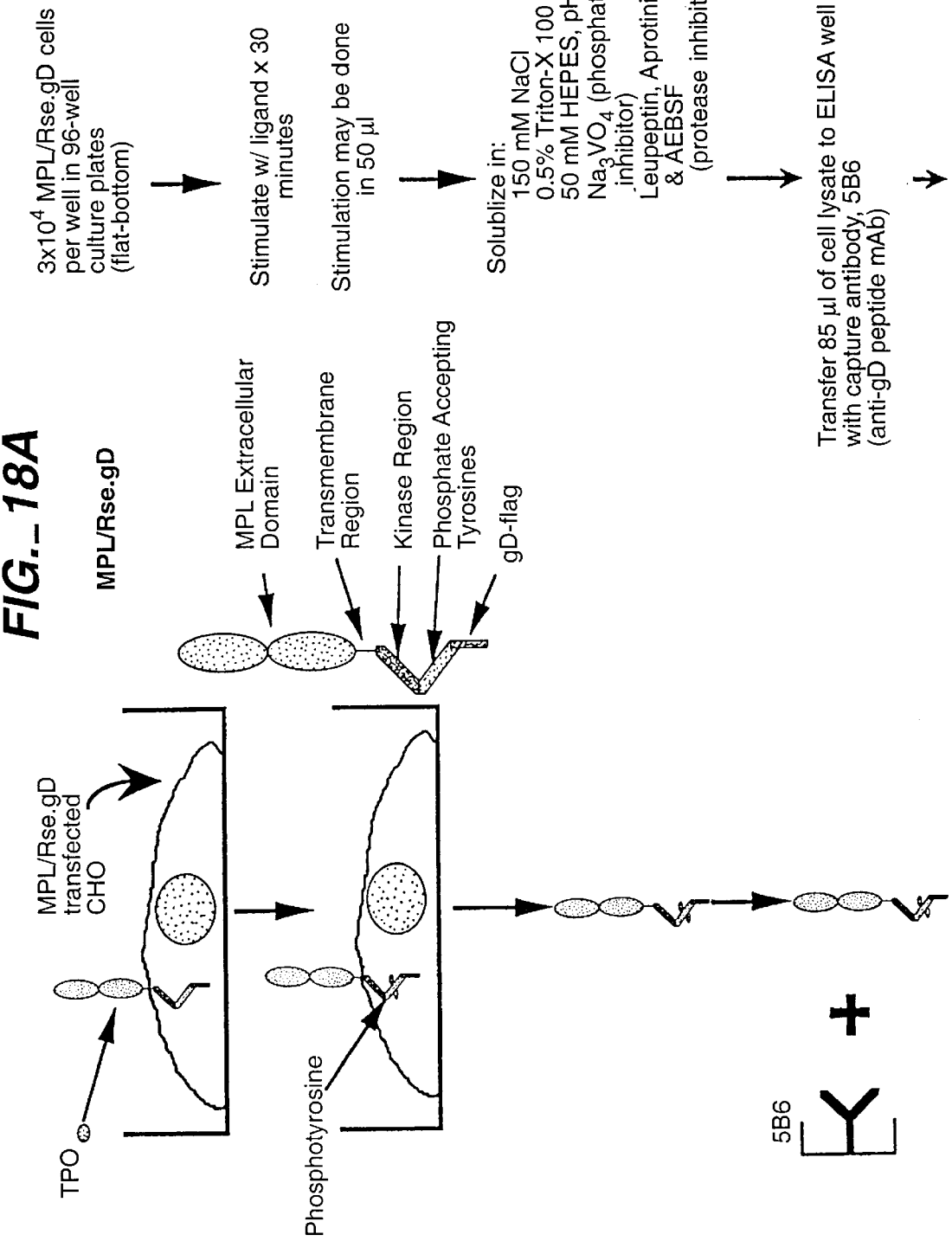
FIG._18A

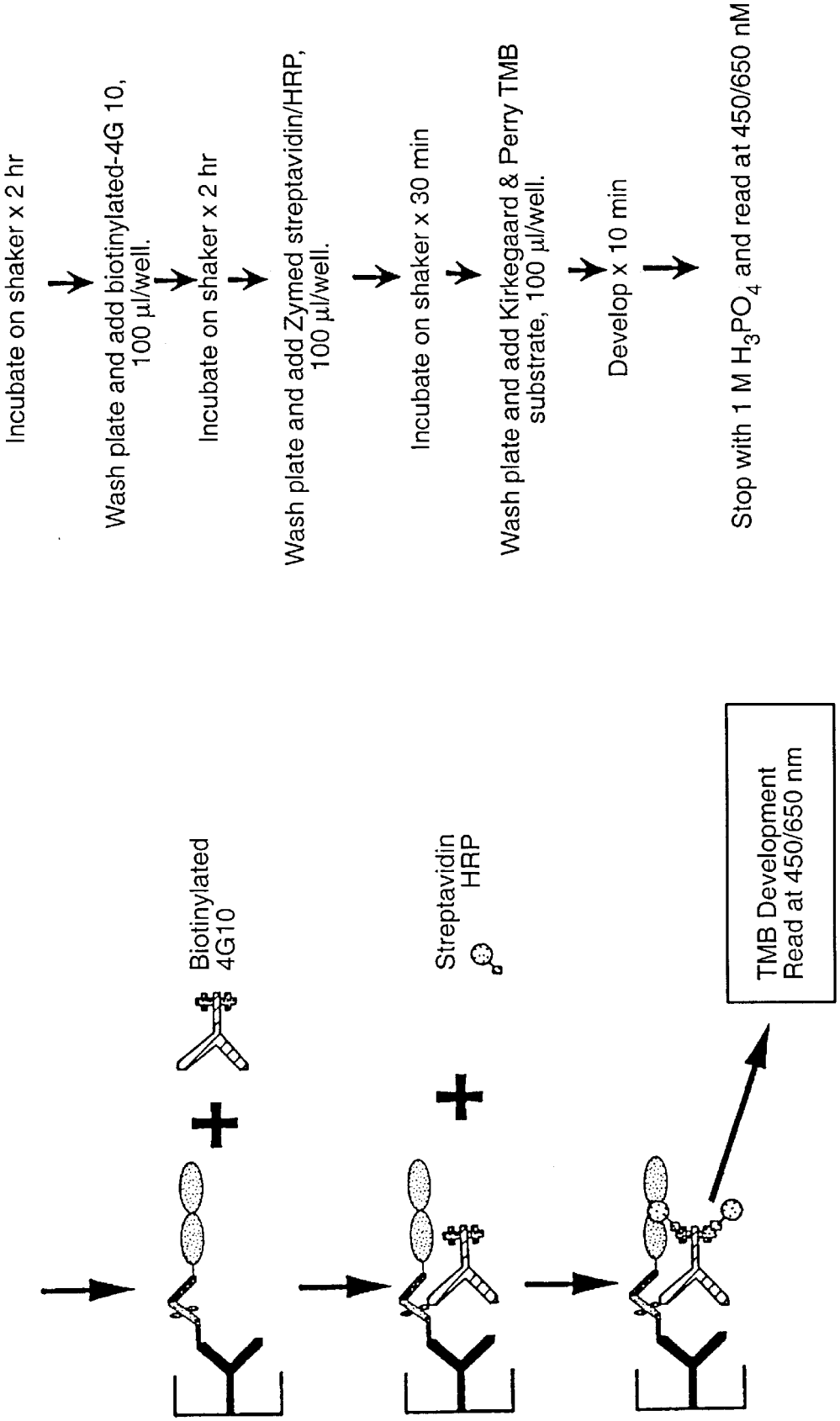
FIG._18B

SEQUENCE LISTING

```
<160> NUMBER OF SEQ ID NOS: 11

<210> SEQ ID NO 1
<211> LENGTH: 911
<212> TYPE: PRT
<213> ORGANISM: Homo Sapien

<400> SEQUENCE: 1

Met Ala Leu Arg Arg Ser Met Gly Arg Pro Gly Leu Pro Pro Leu
 1               5                  10                  15

Pro Leu Pro Pro Pro Arg Leu Gly Leu Leu Leu Ala Ala Leu
                20                  25                  30

Ala Ser Leu Leu Leu Pro Glu Ser Ala Ala Ala Gly Leu Lys Leu
                35                  40                  45

Met Gly Ala Pro Val Lys Leu Thr Val Ser Gln Gly Gln Pro Val
                50                  55                  60

Lys Leu Asn Cys Ser Val Glu Gly Met Glu Glu Pro Asp Ile Gln
                65                  70                  75

Trp Val Lys Asp Gly Ala Val Val Gln Asn Leu Asp Gln Leu Tyr
                80                  85                  90

Ile Pro Val Ser Glu Gln His Trp Ile Gly Phe Leu Ser Leu Lys
                95                 100                 105

Ser Val Glu Arg Ser Asp Ala Gly Arg Tyr Trp Cys Gln Val Glu
                110                115                 120

Asp Gly Gly Glu Thr Glu Ile Ser Gln Pro Val Trp Leu Thr Val
                125                130                 135

Glu Gly Val Pro Phe Phe Thr Val Glu Pro Lys Asp Leu Ala Val
                140                145                 150

Pro Pro Asn Ala Pro Phe Gln Leu Ser Cys Glu Ala Val Gly Pro
                155                160                 165

Pro Glu Pro Val Thr Ile Val Trp Trp Arg Gly Thr Thr Lys Ile
                170                175                 180
```

-continued

```
Gly Gly Pro Ala Pro Ser Pro Val Leu Asn Val Thr Gly Val
            185                 190                 195

Thr Gln Ser Thr Met Phe Ser Cys Glu Ala His Asn Leu Lys Gly
            200                 205                 210

Leu Ala Ser Ser Arg Thr Ala Thr Val His Leu Gln Ala Leu Pro
            215                 220                 225

Ala Ala Pro Phe Asn Ile Thr Val Thr Lys Leu Ser Ser Ser Asn
            230                 235                 240

Ala Ser Val Ala Trp Met Pro Gly Ala Asp Gly Arg Ala Leu Leu
            245                 250                 255

Gln Ser Cys Thr Val Gln Val Thr Gln Ala Pro Gly Gly Trp Glu
            260                 265                 270

Val Leu Ala Val Val Pro Val Pro Pro Phe Thr Cys Leu Leu
            275                 280                 285

Arg Asp Leu Val Pro Ala Thr Asn Tyr Ser Leu Arg Val Arg Cys
            290                 295                 300

Ala Asn Ala Leu Gly Pro Ser Pro Tyr Ala Asp Trp Val Pro Phe
            305                 310                 315

Gln Thr Lys Gly Leu Ala Pro Ala Ser Ala Pro Gln Asn Leu His
            320                 325                 330

Ala Ile Arg Thr Asp Ser Gly Leu Ile Leu Glu Trp Glu Glu Val
            335                 340                 345

Ile Pro Glu Ala Pro Leu Glu Gly Pro Leu Gly Pro Tyr Lys Leu
            350                 355                 360

Ser Trp Val Gln Asp Asn Gly Thr Gln Asp Glu Leu Thr Val Glu
            365                 370                 375

Gly Thr Arg Ala Asn Leu Thr Gly Trp Asp Pro Gln Lys Asp Leu
            380                 385                 390

Ile Val Arg Val Cys Val Ser Asn Ala Val Gly Cys Gly Pro Trp
            395                 400                 405

Ser Gln Pro Leu Val Val Ser Ser His Asp Arg Ala Gly Gln Gln
            410                 415                 420

Gly Pro Pro His Ser Arg Thr Ser Trp Val Pro Val Val Leu Gly
            425                 430                 435

Val Leu Thr Ala Leu Val Thr Ala Ala Ala Leu Ala Leu Ile Leu
            440                 445                 450

Leu Arg Lys Arg Arg Lys Glu Thr Arg Phe Gly Gln Ala Phe Asp
            455                 460                 465

Ser Val Met Ala Arg Gly Glu Pro Ala Val His Phe Arg Ala Ala
            470                 475                 480

Arg Ser Phe Asn Arg Glu Arg Pro Glu Arg Ile Glu Ala Thr Leu
            485                 490                 495

Asp Ser Leu Gly Ile Ser Asp Glu Leu Lys Glu Lys Leu Glu Asp
            500                 505                 510

Val Leu Ile Pro Glu Gln Gln Phe Thr Leu Gly Arg Met Leu Gly
            515                 520                 525

Lys Gly Glu Phe Gly Ser Val Arg Glu Ala Gln Leu Lys Gln Glu
            530                 535                 540

Asp Gly Ser Phe Val Lys Val Ala Val Lys Met Leu Lys Ala Asp
            545                 550                 555

Ile Ile Ala Ser Ser Asp Ile Glu Glu Phe Leu Arg Glu Ala Ala
            560                 565                 570

Cys Met Lys Glu Phe Asp His Pro His Val Ala Lys Leu Val Gly
```

```
                        575                 580                 585
Val Ser Leu Arg Ser Arg Ala Lys Gly Arg Leu Pro Ile Pro Met
                590                 595                 600
Val Ile Leu Pro Phe Met Lys His Gly Asp Leu His Ala Phe Leu
                605                 610                 615
Leu Ala Ser Arg Ile Gly Glu Asn Pro Phe Asn Leu Pro Leu Gln
                620                 625                 630
Thr Leu Ile Arg Phe Met Val Asp Ile Ala Cys Gly Met Glu Tyr
                635                 640                 645
Leu Ser Ser Arg Asn Phe Ile His Arg Asp Leu Ala Ala Arg Asn
                650                 655                 660
Cys Met Leu Ala Glu Asp Met Thr Val Cys Val Ala Asp Phe Gly
                665                 670                 675
Leu Ser Arg Lys Ile Tyr Ser Gly Asp Tyr Tyr Arg Gln Gly Cys
                680                 685                 690
Ala Ser Lys Leu Pro Val Lys Trp Leu Ala Leu Glu Ser Leu Ala
                695                 700                 705
Asp Asn Leu Tyr Thr Val Gln Ser Asp Val Trp Ala Phe Gly Val
                710                 715                 720
Thr Met Trp Glu Ile Met Thr Arg Gly Gln Thr Pro Tyr Ala Gly
                725                 730                 735
Ile Glu Asn Ala Glu Ile Tyr Asn Tyr Leu Ile Gly Gly Asn Arg
                740                 745                 750
Leu Lys Gln Pro Pro Glu Cys Met Glu Asp Val Tyr Asp Leu Met
                755                 760                 765
Tyr Gln Cys Trp Ser Ala Asp Pro Lys Gln Arg Pro Ser Phe Thr
                770                 775                 780
Cys Leu Arg Met Glu Leu Glu Asn Ile Leu Gly Gln Leu Ser Val
                785                 790                 795
Leu Ser Ala Ser Gln Asp Pro Leu Tyr Ile Asn Ile Glu Arg Ala
                800                 805                 810
Glu Glu Pro Thr Ala Gly Gly Ser Leu Glu Leu Pro Gly Arg Asp
                815                 820                 825
Gln Pro Tyr Ser Gly Ala Gly Asp Gly Ser Gly Met Gly Ala Val
                830                 835                 840
Gly Gly Thr Pro Ser Asp Cys Arg Tyr Ile Leu Thr Pro Gly Gly
                845                 850                 855
Leu Ala Glu Gln Pro Gly Gln Ala Glu His Gln Pro Glu Ser Pro
                860                 865                 870
Leu Asn Glu Thr Gln Arg Leu Leu Leu Leu Gln Gln Gly Leu Leu
                875                 880                 885
Pro His Ser Ser Cys Ala Asp Ala Ser Leu Lys Met Ala Asp Pro
                890                 895                 900
Asn Arg Phe Arg Gly Lys Asp Leu Pro Val Leu
                905                 910

<210> SEQ ID NO 2
<211> LENGTH: 2742
<212> TYPE: DNA
<213> ORGANISM: Homo Sapien

<400> SEQUENCE: 2
atggcgctga ggcggagcat ggggcggccg gggctcccgc cgctgccgct          50
gccgccgcca ccgcggctcg ggctgctgct ggcggctctg gcttctctgc         100
```

-continued

| | |
|---|---|
| tgctcccgga gtccgccgcc gcaggtctga agctcatggg agccccggtg | 150 |
| aagctgacag tgtctcaggg gcagccggtg aagctcaact gcagtgtgga | 200 |
| ggggatggag gagcctgaca tccagtgggt gaaggatggg gctgtggtcc | 250 |
| agaacttgga ccagttgtac atcccagtca gcgagcagca ctggatcggc | 300 |
| ttcctcagcc tgaagtcagt ggagcgctct gacgccggcc ggtactggtg | 350 |
| ccaggtggag gatggggggtg aaaccgagat ctcccagcca gtgtggctca | 400 |
| cggtagaagg tgtgccattt ttcacagtgg agccaaaaga tctggcagtg | 450 |
| ccacccaatg cccctttcca actgtcttgt gaggctgtgg gtcccctga | 500 |
| acctgttacc attgtctggt ggagaggaac tacgaagatc gggggacccg | 550 |
| ctccctctcc atctgtttta aatgtaacag gggtgaccca gagcaccatg | 600 |
| ttttcctgtg aagctcacaa cctaaaaggc ctggcctctt ctcgcacagc | 650 |
| cactgttcac cttcaagcac tgcctgcagc cccttcaac atcaccgtga | 700 |
| caaagctttc cagcagcaac gctagtgtgg cctggatgcc aggtgctgat | 750 |
| ggccgagctc tgctacagtc ctgtacagtt caggtgacac aggccccagg | 800 |
| aggctgggaa gtcctggctg ttgtggtccc tgtgcccccc tttacctgcc | 850 |
| tgctccggga cctggtgcct gccaccaact acagcctcag ggtgcgctgt | 900 |
| gccaatgcct tggggccctc tccctatgct gactgggtgc cctttcagac | 950 |
| caagggtcta gccccagcca gcgctcccca aaacctccat gccatccgca | 1000 |
| cagattcagg cctcatcttg gagtgggaag aagtgatccc cgaggcccct | 1050 |
| ttggaaggcc ccctgggacc ctacaaactg tcctgggttc aagacaatgg | 1100 |
| aacccaggat gagctgacag tggagggac cagggccaat ttgacaggct | 1150 |
| gggatcccca aaaggacctg atcgtacgtg tgtgcgtctc caatgcagtt | 1200 |
| ggctgtggac cctggagtca gccactggtg gtctcttctc atgaccgtgc | 1250 |
| aggccagcag ggccctcctc acagccgcac atcctgggta cctgtggtcc | 1300 |
| ttggtgtgct aacggccctg gtgacggctg ctgccctggc cctcatcctg | 1350 |
| cttcgaaaga gacggaaaga gacgcggttt gggcaagcct ttgacagtgt | 1400 |
| catggcccgg ggagagccag ccgttcactt ccgggcagcc cggtccttca | 1450 |
| atcgagaaag gcccgagcgc atcgaggcca cattggacag cttgggcatc | 1500 |
| agcgatgaac taaaggaaaa actggaggat gtgctcatcc cagagcagca | 1550 |
| gttcaccctg ggccggatgt tgggcaaagg agagtttggt tcagtgcggg | 1600 |
| aggcccagct gaagcaagag gatggctcct tgtgaaagt ggctgtgaag | 1650 |
| atgctgaaag ctgacatcat tgcctcaagc gacattgaag agttcctcag | 1700 |
| ggaagcagct tgcatgaagg agtttgacca tccacacgtg gccaaacttg | 1750 |
| ttggggtaag cctccggagc agggctaaag gccgtctccc catccccatg | 1800 |
| gtcatcttgc ccttcatgaa gcatggggac ctgcatgcct tcctgctcgc | 1850 |
| ctcccggatt ggggagaacc cctttaacct accctccag accctgatcc | 1900 |
| ggttcatggt ggacattgcc tgcggcatgg agtacctgag ctctcggaac | 1950 |
| ttcatccacc gagacctggc tgctcggaat tgcatgctgg cagaggacat | 2000 |
| gacagtgtgt gtggctgact cggactctc ccggaagatc tacagtgggg | 2050 |

-continued

```
actactatcg tcaaggctgt gcctccaaac tgcctgtcaa gtggctggcc        2100
ctggagagcc tggccgacaa cctgtatact gtgcagagtg acgtgtgggc        2150
gttcggggtg accatgtggg agatcatgac acgtgggcag acgccatatg        2200
ctggcatcga aaacgctgag atttacaact acctcattgg cgggaaccgc        2250
ctgaaacagc tccggagtg tatggaggac gtgtatgatc tcatgtacca         2300
gtgctggagt gctgacccca agcagcgccc gagctttact tgtctgcgaa        2350
tggaactgga gaacatcttg ggccagctgt ctgtgctatc tgccagccag        2400 gacccttat acatcaacat cgagagagct gaggagccca ctgcgggagg         2450
cagcctggag ctacctggca gggatcagcc tacagtgggg ctggggatg         2500 gcagtggcat gggggcagtg ggtggcactc ccagtgactg tcggtacata        2550
ctcacccccg gagggctggc tgagcagcca gggcaggcag agcaccagcc        2600
agagagtccc ctcaatgaga cacagaggct tttgctgctg cagcaagggc        2650
tactgccaca ctcgagctgc gcagatgcta gcctcaagat ggctgatcca        2700
aatcgattcc gcggcaaaga tcttccggtc ctgtagaagc tt               2742
```

<210> SEQ ID NO 3
<211> LENGTH: 814
<212> TYPE: PRT
<213> ORGANISM: Homo Sapien

<400> SEQUENCE: 3

```
Met Gly Gly Thr Ala Ala Arg Leu Gly Ala Val Ile Leu Phe Val
  1               5                  10                  15

Val Ile Val Gly Leu His Gly Val Arg Gly Lys Tyr Ala Leu Ala
                 20                  25                  30

Asp Ala Ser Leu Lys Met Ala Asp Pro Asn Arg Phe Arg Gly Lys
                 35                  40                  45

Asp Leu Pro Val Leu Asp Gln Leu Leu Glu Val Ala Ala Pro Cys
                 50                  55                  60

Pro Asp Ala Cys Cys Pro His Gly Ser Ser Gly Leu Arg Cys Thr
                 65                  70                  75

Arg Asp Gly Ala Leu Asp Ser Leu His His Leu Pro Gly Ala Glu
                 80                  85                  90

Asn Leu Thr Glu Leu Tyr Ile Glu Asn Gln Gln His Leu Gln His
                 95                 100                 105

Leu Glu Leu Arg Asp Leu Arg Gly Leu Gly Glu Leu Arg Asn Leu
                110                 115                 120

Thr Ile Val Lys Ser Gly Leu Arg Phe Val Ala Pro Asp Ala Phe
                125                 130                 135

His Phe Thr Pro Arg Leu Ser Arg Leu Asn Leu Ser Phe Asn Ala
                140                 145                 150

Leu Glu Ser Leu Ser Trp Lys Thr Val Gln Gly Leu Ser Leu Gln
                155                 160                 165

Glu Leu Val Leu Ser Gly Asn Pro Leu His Cys Ser Cys Ala Leu
                170                 175                 180

Arg Trp Leu Gln Arg Trp Glu Glu Glu Gly Leu Gly Gly Val Pro
                185                 190                 195

Glu Gln Lys Leu Gln Cys His Gly Gln Gly Pro Leu Ala His Met
                200                 205                 210

Pro Asn Ala Ser Cys Gly Val Pro Thr Leu Lys Val Gln Val Pro
```

-continued

```
                215                 220                 225
Asn Ala Ser Val Asp Val Gly Asp Asp Val Leu Leu Arg Cys Gln
                230                 235                 240
Val Glu Gly Arg Gly Leu Glu Gln Ala Gly Trp Ile Leu Thr Glu
                245                 250                 255
Leu Glu Gln Ser Ala Thr Val Met Lys Ser Gly Gly Leu Pro Ser
                260                 265                 270
Leu Gly Leu Thr Leu Ala Asn Val Thr Ser Asp Leu Asn Arg Lys
                275                 280                 285
Asn Leu Thr Cys Trp Ala Glu Asn Asp Val Gly Arg Ala Glu Val
                290                 295                 300
Ser Val Gln Val Asn Val Ser Phe Pro Ala Ser Val Gln Leu His
                305                 310                 315
Thr Ala Val Glu Met His His Trp Cys Ile Pro Phe Ser Val Asp
                320                 325                 330
Gly Gln Pro Ala Pro Ser Leu Arg Trp Leu Phe Asn Gly Ser Val
                335                 340                 345
Leu Asn Glu Thr Ser Phe Ile Phe Thr Glu Phe Leu Glu Pro Ala
                350                 355                 360
Ala Asn Glu Thr Val Arg His Gly Cys Leu Arg Leu Asn Gln Pro
                365                 370                 375
Thr His Val Asn Asn Gly Asn Tyr Thr Leu Leu Ala Ala Asn Pro
                380                 385                 390
Phe Gly Gln Ala Ser Ala Ser Ile Met Ala Ala Phe Met Asp Asn
                395                 400                 405
Pro Phe Glu Phe Asn Pro Glu Asp Pro Ile Pro Asp Thr Asn Ser
                410                 415                 420
Thr Ser Gly Asp Pro Val Glu Lys Lys Asp Glu Thr Pro Phe Gly
                425                 430                 435
Val Ser Val Ala Val Gly Leu Ala Val Phe Ala Cys Leu Phe Leu
                440                 445                 450
Ser Thr Leu Leu Leu Val Leu Asn Lys Cys Gly Arg Arg Asn Lys
                455                 460                 465
Phe Gly Ile Asn Arg Pro Ala Val Leu Ala Pro Glu Asp Gly Leu
                470                 475                 480
Ala Met Ser Leu His Phe Met Thr Leu Gly Gly Ser Ser Leu Ser
                485                 490                 495
Pro Thr Glu Gly Lys Gly Ser Gly Leu Gln Gly His Ile Ile Glu
                500                 505                 510
Asn Pro Gln Tyr Phe Ser Asp Ala Cys Val His His Ile Lys Arg
                515                 520                 525
Arg Asp Ile Val Leu Lys Trp Glu Leu Gly Glu Gly Ala Phe Gly
                530                 535                 540
Lys Val Phe Leu Ala Glu Cys His Asn Leu Leu Pro Glu Gln Asp
                545                 550                 555
Lys Met Leu Val Ala Val Lys Ala Leu Lys Glu Ala Ser Glu Ser
                560                 565                 570
Ala Arg Gln Asp Phe Gln Arg Glu Ala Glu Leu Leu Thr Met Leu
                575                 580                 585
Gln His Gln His Ile Val Arg Phe Phe Gly Val Cys Thr Glu Gly
                590                 595                 600
Arg Pro Leu Leu Met Val Phe Glu Tyr Met Arg His Gly Asp Leu
                605                 610                 615
```

```
Asn Arg Phe Leu Arg Ser His Gly Pro Asp Ala Lys Leu Leu Ala
                620                 625                 630

Gly Gly Glu Asp Val Ala Pro Gly Pro Leu Gly Leu Gly Gln Leu
            635                 640                 645

Leu Ala Val Ala Ser Gln Val Ala Ala Gly Met Val Tyr Leu Ala
            650                 655                 660

Gly Leu His Phe Val His Arg Asp Leu Ala Thr Arg Asn Cys Leu
            665                 670                 675

Val Gly Gln Gly Leu Val Val Lys Ile Gly Asp Phe Gly Met Ser
            680                 685                 690

Arg Asp Ile Tyr Ser Thr Asp Tyr Tyr Arg Val Gly Gly Arg Thr
            695                 700                 705

Met Leu Pro Ile Arg Trp Met Pro Pro Glu Ser Ile Leu Tyr Arg
            710                 715                 720

Lys Phe Thr Thr Glu Ser Asp Val Trp Ser Phe Gly Val Val Leu
            725                 730                 735

Trp Glu Ile Phe Thr Tyr Gly Lys Gln Pro Trp Tyr Gln Leu Ser
            740                 745                 750

Asn Thr Glu Ala Ile Asp Cys Ile Thr Gln Gly Arg Glu Leu Glu
            755                 760                 765

Arg Pro Arg Ala Cys Pro Pro Glu Val Tyr Ala Ile Met Arg Gly
            770                 775                 780

Cys Trp Gln Arg Glu Pro Gln Gln Arg His Ser Ile Lys Asp Val
            785                 790                 795

His Ala Arg Leu Gln Ala Leu Ala Gln Ala Pro Pro Val Tyr Leu
            800                 805                 810

Asp Val Leu Gly

<210> SEQ ID NO 4
<211> LENGTH: 2820
<212> TYPE: DNA
<213> ORGANISM: Homo Sapien

<400> SEQUENCE: 4
tatagaataa catccacttt gcctttctct ccacaggtgt ccactcccag              50
gtccaactgc acctgaattc cactgccttc caccaagctc tgcaggatcc             100
cagagtcagg ggtctgtatc ttcctgctgg tggctccagt tcaggaacag             150
taaaccctgc tccgaatatt gcctctcaca tctcgtcaat ctccgcgagg             200
actggggacc ctgtgacaag cttcagcgcg aacgaccaac taccccgatc             250
atcagttatc cttaaggtct cttttgtgtg gtgcgttccg gtatgggggg             300
gactgccgcc aggttggggg ccgtgatttt gtttgtcgtc atagtgggcc             350
tccatggggt ccgcggcaaa tatgccttgg cggatgcctc tctcaagatg             400
gccgacccca tcgatttcg cggcaaagac cttccggtcc tggaccagct              450
gctcgaggta gccgcaccct gccccgatgc ctgctgcccc acggctcct              500 cgggactgcg atgcacccgg gatggggccc tggatagcct ccaccacctg             550
cccggcgcag agaacctgac tgagctctac atcgagaacc agcagcatct             600
gcagcatctg gagctccgtg atctgagggg cctgggggag ctgagaaacc             650
tcaccatcgt gaagagtggt ctccgtttcg tggcgccaga tgccttccat             700
ttcactcctc ggctcagtcg cctgaatctc tccttcaacg ctctggagtc             750
```

-continued

| | |
|---|---|
| tctctcctgg aaaactgtgc agggcctctc cttacaggaa ctggtcctgt | 800 |
| cggggaaccc tctgcactgt tcttgtgccc tgcgctggct acagcgctgg | 850 |
| gaggaggagg gactgggcgg agtgcctgaa cagaagctgc agtgtcatgg | 900 |
| gcaagggccc ctggcccaca tgcccaatgc cagctgtggt gtgcccacgc | 950 |
| tgaaggtcca ggtgcccaat gcctcggtgg atgtggggga cgacgtgctg | 1000 |
| ctgcggtgcc aggtggaggg gcggggcctg gagcaggccg gctggatcct | 1050 |
| cacagagctg gagcagtcag ccacggtgat gaaatctggg ggtctgccat | 1100 |
| ccctggggct gaccctggcc aatgtcacca gtgacctcaa caggaagaac | 1150 |
| ttgacgtgct gggcagagaa cgatgtgggc cgggcagagg tctctgttca | 1200 |
| ggtcaacgtc tccttcccgg ccagtgtgca gctgcacacg gcggtggaga | 1250 |
| tgcaccactg gtgcatcccc ttctctgtgg atgggcagcc ggcaccgtct | 1300 |
| ctgcgctggc tcttcaatgg ctccgtgctc aatgagacca gcttcatctt | 1350 |
| cactgagttc ctggagccgg cagccaatga gaccgtgcgg cacgggtgtc | 1400 |
| tgcgcctcaa ccagcccacc cacgtcaaca acggcaacta cacgctgctg | 1450 |
| gctgccaacc ccttcggcca ggcctccgcc tccatcatgg ctgccttcat | 1500 |
| ggacaaccct ttcgagttca accccgagga ccccatccct gacactaaca | 1550 |
| gcacatctgg agaccggtg gagaagaagg acgaaacacc ttttgggggtc | 1600 |
| tcggtggctg tgggcctggc cgtctttgcc tgcctcttcc tttctacgct | 1650 |
| gctccttgtg ctcaacaaat gtggacgag aaacaagttt gggatcaacc | 1700 |
| gcccggctgt gctggctcca gaggatgggc tggccatgtc cctgcatttc | 1750 |
| atgacattgg gtggcagctc cctgtccccc accgagggca aaggctctgg | 1800 |
| gctccaaggc cacatcatcg agaacccaca atacttcagt gatgcctgtg | 1850 |
| ttcaccacat caagcgccgg gacatcgtgc tcaagtggga gctggggggag | 1900 |
| ggcgcctttg ggaaggtctt ccttgctgag tgccacaacc tcctgcctga | 1950 |
| gcaggacaag atgctggtgg ctgtcaaggc actgaaggag cgtcccgaga | 2000 |
| gtgctcggca ggacttccaa cgtgaggctg agctgctcac catgctgcag | 2050 |
| caccagcaca tcgtgcgctt cttcggcgtc tgcaccgagg ccgccccct | 2100 |
| gctcatggtc tttgagtata tgcggcacgg ggacctcaac cgcttcctcc | 2150 |
| gatcccatgg acctgatgcc aagctgctgg ctggtgggga ggatgtggct | 2200 |
| ccaggccccc tgggtctggg gcagctgctg gccgtggcta gccaggtcgc | 2250 |
| tgcggggatg gtgtacctgg cgggtctgca ttttgtgcac cgggacctgg | 2300 |
| ccacacgcaa ctgtctagtg ggccagggac tggtggtcaa gattggtgat | 2350 |
| tttggcatga gcagggatat ctacagcacc gactattacc gtgtgggagg | 2400 |
| ccgcaccatg ctgcccattc gctggatgcc gcccgagagc atcctgtacc | 2450 |
| gtaagttcac caccgagagc gacgtgtgga gcttcggcgt ggtgctctgg | 2500 |
| gagatcttca cctacggcaa gcagccctgg taccagctct ccaacacgga | 2550 |
| ggcaatcgac tgcatcacgc agggacgtga gttggagcgg ccacgtgcct | 2600 |
| gcccaccaga ggtctacgcc atcatgcggg gctgctggca gcgggagccc | 2650 |
| cagcaacgcc acagcatcaa ggatgtgcac gcccggctgc aagccctggc | 2700 |

```
ccaggcacct cctgtctacc tggatgtcct gggctagaat taattcaatc            2750
gatggccgcc atggcccaac ttgtttattg cagcttataa tggttacaaa            2800
taaagcaata gcatcacaaa                                             2820
```

<210> SEQ ID NO 5
<211> LENGTH: 847
<212> TYPE: PRT
<213> ORGANISM: Homo Sapien

<400> SEQUENCE: 5

```
Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Val Cys Pro Thr Ser
                50                  55                  60

Cys Lys Cys Ser Ala Ser Arg Ile Trp Cys Ser Asp Pro Ser Pro
                65                  70                  75

Gly Ile Val Ala Phe Pro Arg Leu Glu Pro Asn Ser Val Asp Pro
                80                  85                  90

Glu Asn Ile Thr Glu Ile Phe Ile Ala Asn Gln Lys Arg Leu Glu
                95                 100                 105

Ile Ile Asn Glu Asp Asp Val Glu Ala Tyr Val Gly Leu Arg Asn
               110                 115                 120

Leu Thr Ile Val Asp Ser Gly Leu Lys Phe Val Ala His Lys Ala
               125                 130                 135

Phe Leu Lys Asn Ser Asn Leu Gln His Ile Asn Phe Thr Arg Asn
               140                 145                 150

Lys Leu Thr Ser Leu Ser Arg Lys His Phe Arg His Leu Asp Leu
               155                 160                 165

Ser Glu Leu Ile Leu Val Gly Asn Pro Phe Thr Cys Ser Cys Asp
               170                 175                 180

Ile Met Trp Ile Lys Thr Leu Gln Glu Ala Lys Ser Ser Pro Asp
               185                 190                 195

Thr Gln Asp Leu Tyr Cys Leu Asn Glu Ser Ser Lys Asn Ile Pro
               200                 205                 210

Leu Ala Asn Leu Gln Ile Pro Asn Cys Gly Leu Pro Ser Ala Asn
               215                 220                 225

Leu Ala Ala Pro Asn Leu Thr Val Glu Glu Gly Lys Ser Ile Thr
               230                 235                 240

Leu Ser Cys Ser Val Ala Gly Asp Pro Val Pro Asn Met Tyr Trp
               245                 250                 255

Asp Val Gly Asn Leu Val Ser Lys His Met Asn Glu Thr Ser His
               260                 265                 270

Thr Gln Gly Ser Leu Arg Ile Thr Asn Ile Ser Ser Asp Asp Ser
               275                 280                 285

Gly Lys Gln Ile Ser Cys Val Ala Glu Asn Leu Val Gly Glu Asp
               290                 295                 300

Gln Asp Ser Val Asn Leu Thr Val His Phe Ala Pro Thr Ile Thr
               305                 310                 315

Phe Leu Glu Ser Pro Thr Ser Asp His His Trp Cys Ile Pro Phe
               320                 325                 330
```

-continued

```
Thr Val Lys Gly Asn Pro Lys Pro Ala Leu Gln Trp Phe Tyr Asn
            335                 340                 345
Gly Ala Ile Leu Asn Glu Ser Lys Tyr Ile Cys Thr Lys Ile His
            350                 355                 360
Val Thr Asn His Thr Glu Tyr His Gly Cys Leu Gln Leu Asp Asn
            365                 370                 375
Pro Thr His Met Asn Asn Gly Asp Tyr Thr Leu Ile Ala Lys Asn
            380                 385                 390
Glu Tyr Gly Lys Asp Glu Lys Gln Ile Ser Ala His Phe Met Gly
            395                 400                 405
Trp Pro Gly Ile Asp Asp Gly Ala Asn Pro Asn Tyr Pro Asp Val
            410                 415                 420
Ile Tyr Glu Asp Tyr Gly Thr Ala Ala Asn Asp Ile Gly Asp Thr
            425                 430                 435
Thr Asn Arg Ser Asn Glu Ile Pro Ser Thr Asp Val Thr Asp Lys
            440                 445                 450
Thr Gly Arg Glu His Leu Ser Val Tyr Ala Val Val Ile Ala
            455                 460                 465
Ser Val Val Gly Phe Cys Leu Leu Val Met Leu Phe Leu Leu Lys
            470                 475                 480
Leu Ala Arg His Ser Lys Phe Gly Met Lys Gly Pro Ala Ser Val
            485                 490                 495
Ile Ser Asn Asp Asp Asp Ser Ala Ser Pro Leu His His Ile Ser
            500                 505                 510
Asn Gly Ser Asn Thr Pro Ser Ser Ser Glu Gly Gly Pro Asp Ala
            515                 520                 525
Val Ile Ile Gly Met Thr Lys Ile Pro Val Ile Glu Asn Pro Gln
            530                 535                 540
Tyr Phe Gly Ile Thr Asn Ser Gln Leu Lys Pro Asp Thr Phe Val
            545                 550                 555
Gln His Ile Lys Arg His Asn Ile Val Leu Lys Arg Glu Leu Gly
            560                 565                 570
Glu Gly Ala Phe Gly Lys Val Phe Leu Ala Glu Cys Tyr Asn Leu
            575                 580                 585
Cys Pro Glu Gln Asp Lys Ile Leu Val Ala Val Lys Thr Leu Lys
            590                 595                 600
Asp Ala Ser Asp Asn Ala Arg Lys Asp Phe His Arg Glu Ala Glu
            605                 610                 615
Leu Leu Thr Asn Leu Gln His Glu His Ile Val Lys Phe Tyr Gly
            620                 625                 630
Val Cys Val Glu Gly Asp Pro Leu Ile Met Val Phe Glu Tyr Met
            635                 640                 645
Lys His Gly Asp Leu Asn Lys Phe Leu Arg Ala His Gly Pro Asp
            650                 655                 660
Ala Val Leu Met Ala Glu Gly Asn Pro Pro Thr Glu Leu Thr Gln
            665                 670                 675
Ser Gln Met Leu His Ile Ala Gln Gln Ile Ala Ala Gly Met Val
            680                 685                 690
Tyr Leu Ala Ser Gln His Phe Val His Arg Asp Leu Ala Thr Arg
            695                 700                 705
Asn Cys Leu Val Gly Glu Asn Leu Leu Val Lys Ile Gly Asp Phe
            710                 715                 720
```

```
Gly Met Ser Arg Asp Val Tyr Ser Thr Asp Tyr Tyr Arg Val Gly
            725                 730                 735

Gly His Thr Met Leu Pro Ile Arg Trp Met Pro Pro Glu Ser Ile
            740                 745                 750

Met Tyr Arg Lys Phe Thr Thr Glu Ser Asp Val Trp Ser Leu Gly
            755                 760                 765

Val Val Leu Trp Glu Ile Phe Tyr Gly Lys Gln Pro Trp Tyr
            770                 775                 780

Gln Leu Ser Asn Asn Glu Val Ile Glu Cys Ile Thr Gln Gly Arg
            785                 790                 795

Val Leu Gln Arg Pro Arg Thr Cys Pro Gln Glu Val Tyr Glu Leu
            800                 805                 810

Met Leu Gly Cys Trp Gln Arg Glu Pro His Met Arg Lys Asn Ile
            815                 820                 825

Lys Gly Ile His Thr Leu Leu Gln Asn Leu Ala Lys Ala Ser Pro
            830                 835                 840

Val Tyr Leu Asp Ile Leu Gly
            845

<210> SEQ ID NO 6
<211> LENGTH: 3060
<212> TYPE: DNA
<213> ORGANISM: Homo Sapien

<400> SEQUENCE: 6
```

| | | | | | |
|---|---|---|---|---|---|
| tatagaataa | catccacttt | gcctttctct | ccacaggtgt | ccactcccag | 50 |
| gtccaactgc | acctcggttc | tatcgattga | attccactgc | cttccaccaa | 100 |
| gctctgcagg | atcccagagt | cagggtctg | tatcttcctg | ctggtggctc | 150 |
| cagttcagga | acagtaaacc | ctgctccgaa | tattgcctct | cacatctcgt | 200 |
| caatctccgc | gaggactggg | gaccctgtga | caagcttcag | cgcgaacgac | 250 |
| caactacccc | gatcatcagt | tatccttaag | gtctcttttg | tgtggtgcgt | 300 |
| tccggtatgg | ggggactgc | cgccaggttg | ggggccgtga | ttttgtttgt | 350 |
| cgtcatagtg | ggcctccatg | gggtccgcgg | caaatatgcc | ttggcggatg | 400 |
| cctctctcaa | gatggccgac | cccaatcgat | ttcgcggcaa | agaccttccg | 450 |
| gtcctggacc | agctgctcga | ggtatgtccc | acgtcctgca | aatgcagtgc | 500 |
| ctctcggatc | tggtgcagcg | acccttctcc | tggcatcgtg | gcatttccga | 550 |
| gattggagcc | taacagtgta | gatcctgaga | acatcaccga | aattttcatc | 600 |
| gcaaaccaga | aaggttaga | aatcatcaac | gaagatgatg | ttgaagctta | 650 |
| tgtgggactg | agaaatctga | caattgtgga | ttctggatta | aaatttgtgg | 700 |
| ctcataaagc | atttctgaaa | aacagcaacc | tgcagcacat | caattttacc | 750 |
| cgaaacaaac | tgacgagttt | gtctaggaaa | catttccgtc | accttgactt | 800 |
| gtctgaactg | atcctggtgg | gcaatccatt | tacatgctcc | tgtgacatta | 850 |
| tgtggatcaa | gactctccaa | gaggctaaat | ccagtccaga | cactcaggat | 900 |
| ttgtactgcc | tgaatgaaag | cagcaagaat | attcccctgg | caaacctgca | 950 |
| gataccaat | tgtggtttgc | catctgcaaa | tctggccgca | cctaacctca | 1000 |
| ctgtggagga | aggaaagtct | atcacattat | cctgtagtgt | ggcaggtgat | 1050 |
| ccggttccta | atatgtattg | ggatgttggt | aacctggttt | ccaaacatat | 1100 |

-continued

| | |
|---|---|
| gaatgaaaca agccacacac agggctcctt aaggataact aacatttcat | 1150 |
| ccgatgacag tgggaagcag atctcttgtg tggcggaaaa tcttgtagga | 1200 |
| gaagatcaag attctgtcaa cctcactgtg cattttgcac caactatcac | 1250 |
| atttctcgaa tctccaacct cagaccacca ctggtgcatt ccattcactg | 1300 |
| tgaaaggcaa cccaaaacca gcgcttcagt ggttctataa cggggcaata | 1350 |
| ttgaatgagt ccaaatacat ctgtactaaa atacatgtta ccaatcacac | 1400 |
| ggagtaccac ggctgcctcc agctggataa tcccactcac atgaacaatg | 1450 |
| gggactacac tctaatagcc aagaatgagt atgggaagga tgagaaacag | 1500 |
| atttctgctc acttcatggg ctggcctgga attgacgatg gtgcaaaccc | 1550 |
| aaattatcct gatgtaattt atgaagatta tggaactgca gcgaatgaca | 1600 |
| tcggggacac cacgaacaga agtaatgaaa tcccttccac agacgtcact | 1650 |
| gataaaaccg gtcgggaaca tctctcggtc tatgctgtgg tggtgattgc | 1700 |
| gtctgtggtg ggattttgcc ttttggtaat gctgtttctg cttaagttgg | 1750 |
| caagacactc caagtttggc atgaaaggcc cagcctccgt tatcagcaat | 1800 |
| gatgatgact ctgccagccc actccatcac atctccaatg ggagtaacac | 1850 |
| tccatcttct tcggaaggtg gcccagatgc tgtcattatt ggaatgacca | 1900 |
| agatccctgt cattgaaaat ccccagtact ttggcatcac caacagtcag | 1950 |
| ctcaagccag acacatttgt tcagcacatc aagcgacata acattgttct | 2000 |
| gaaaagggag ctaggcgaag gagcctttgg aaaagtgttc ctagctgaat | 2050 |
| gctataacct ctgtcctgag caggacaaga tcttggtggc agtgaagacc | 2100 |
| ctgaaggatg ccagtgacaa tgcacgcaag gacttccacc gtgaggccga | 2150 |
| gctcctgacc aacctccagc atgagcacat cgtcaagttc tatggcgtct | 2200 |
| gcgtggaggg cgaccccctc atcatggtct ttgagtacat gaagcatggg | 2250 |
| gacctcaaca agttcctcag ggcacacggc cctgatgccg tgctgatggc | 2300 |
| tgagggcaac ccgcccacgg aactgacgca gtcgcagatg ctgcatatag | 2350 |
| cccagcagat cgccgcgggc atggtctacc tggcgtccca gcacttcgtg | 2400 |
| caccgcgatt tggccaccag gaactgcctg gtcgggagaa acttgctggt | 2450 |
| gaaaatcggg gactttggga tgtcccggga cgtgtacagc actgactact | 2500 |
| acagggtcgg tggccacaca atgctgccca ttcgctggat gcctccagag | 2550 |
| agcatcatgt acaggaaatt cacgacggaa agcgacgtct ggagcctggg | 2600 |
| ggtcgtgttg tgggagattt tcacctatgg caaacagccc tggtaccagc | 2650 |
| tgtcaaacaa tgaggtgata gagtgtatca ctcaggccg agtcctgcag | 2700 |
| cgaccccgca cgtgccccca ggaggtgtat gagctgatgc tggggtgctg | 2750 |
| gcagcgagag cccacatga ggaagaacat caagggcatc catacccctcc | 2800 |
| ttcagaactt ggccaaggca tctccggtct acctggacat tctaggctag | 2850 |
| ggccctttc cccagaccga tccttcccaa cgtactcctc agacgggctg | 2900 |
| agaggatgaa catcttttaa ctgccgctgg aggccaccaa gctgctctcc | 2950 |
| ttcactctga cagtattaac atcaaagact ccgagaagct ctcgacctgc | 3000 |
| agaagcttgg ccgccatggc ccaacttgtt tattgcagct tataatggtt | 3050 |
| acaaataaag | 3060 |

<210> SEQ ID NO 7
<211> LENGTH: 850
<212> TYPE: PRT
<213> ORGANISM: Homo Sapien

<400> SEQUENCE: 7

```
Met Gly Gly Thr Ala Ala Arg Leu Gly Ala Val Ile Leu Phe Val
 1               5                  10                  15

Val Ile Val Gly Leu His Gly Val Arg Gly Lys Tyr Ala Leu Ala
                20                  25                  30

Asp Ala Ser Leu Lys Met Ala Asp Pro Asn Arg Phe Arg Gly Lys
                35                  40                  45

Asp Leu Pro Val Leu Asp Gln Leu Leu Glu Val Cys Pro Ala Asn
                50                  55                  60

Cys Val Cys Ser Lys Thr Glu Ile Asn Cys Arg Arg Pro Asp Asp
                65                  70                  75

Gly Asn Leu Phe Pro Leu Leu Glu Gly Gln Asp Ser Gly Asn Ser
                80                  85                  90

Asn Gly Asn Ala Asn Ile Asn Ile Thr Asp Ile Ser Arg Asn Ile
                95                 100                 105

Thr Ser Ile His Ile Glu Asn Trp Arg Ser Leu His Thr Leu Asn
               110                 115                 120

Ala Val Asp Met Glu Leu Tyr Thr Gly Leu Gln Lys Leu Thr Ile
               125                 130                 135

Lys Asn Ser Gly Leu Arg Ser Ile Gln Pro Arg Ala Phe Ala Lys
               140                 145                 150

Asn Pro His Leu Arg Tyr Ile Asn Leu Ser Ser Asn Arg Leu Thr
               155                 160                 165

Thr Leu Ser Trp Gln Leu Phe Gln Thr Leu Ser Leu Arg Glu Leu
               170                 175                 180

Gln Leu Glu Gln Asn Phe Phe Asn Cys Ser Cys Asp Ile Arg Trp
               185                 190                 195

Met Gln Leu Trp Gln Glu Gln Gly Glu Ala Lys Leu Asn Ser Gln
               200                 205                 210

Asn Leu Tyr Cys Ile Asn Ala Asp Gly Ser Gln Leu Pro Leu Phe
               215                 220                 225

Arg Met Asn Ile Ser Gln Cys Asp Leu Pro Glu Ile Ser Val Ser
               230                 235                 240

His Val Asn Leu Thr Val Arg Glu Gly Asp Asn Ala Val Ile Thr
               245                 250                 255

Cys Asn Gly Ser Gly Ser Pro Leu Pro Asp Val Asp Trp Ile Val
               260                 265                 270

Thr Gly Leu Gln Ser Ile Asn Thr His Gln Thr Asn Leu Asn Trp
               275                 280                 285

Thr Asn Val His Ala Ile Asn Leu Thr Leu Val Asn Val Thr Ser
               290                 295                 300

Glu Asp Asn Gly Phe Thr Leu Thr Cys Ile Ala Glu Asn Val Val
               305                 310                 315

Gly Met Ser Asn Ala Ser Val Ala Leu Thr Val Tyr Tyr Pro Pro
               320                 325                 330

Arg Val Val Ser Leu Glu Glu Pro Glu Leu Arg Leu Glu His Cys
               335                 340                 345

Ile Glu Phe Val Val Arg Gly Asn Pro Pro Pro Thr Leu His Trp
```

-continued

```
                        350                 355                 360
Leu His Asn Gly Gln Pro Leu Arg Glu Ser Lys Ile Ile His Val
                365                 370                 375
Glu Tyr Tyr Gln Glu Gly Glu Ile Ser Glu Gly Cys Leu Leu Phe
                380                 385                 390
Asn Lys Pro Thr His Tyr Asn Gly Asn Tyr Thr Leu Ile Ala
                395                 400                 405
Lys Asn Pro Leu Gly Thr Ala Asn Gln Thr Ile Asn Gly His Phe
                410                 415                 420
Leu Lys Glu Pro Phe Pro Glu Ser Thr Asp Asn Phe Ile Leu Phe
                425                 430                 435
Asp Glu Val Ser Pro Thr Pro Pro Ile Thr Val Thr His Lys Pro
                440                 445                 450
Glu Glu Asp Thr Phe Gly Val Ser Ile Ala Val Gly Leu Ala Ala
                455                 460                 465
Phe Ala Cys Val Leu Leu Val Val Leu Phe Val Met Ile Asn Lys
                470                 475                 480
Tyr Gly Arg Arg Ser Lys Phe Gly Met Lys Gly Pro Val Ala Val
                485                 490                 495
Ile Ser Gly Glu Glu Asp Ser Ala Ser Pro Leu His His Ile Asn
                500                 505                 510
His Gly Ile Thr Thr Pro Ser Ser Leu Asp Ala Gly Pro Asp Thr
                515                 520                 525
Val Val Ile Gly Met Thr Arg Ile Pro Val Ile Glu Asn Pro Gln
                530                 535                 540
Tyr Phe Arg Gln Gly His Asn Cys His Lys Pro Asp Thr Tyr Val
                545                 550                 555
Gln His Ile Lys Arg Arg Asp Ile Val Leu Lys Arg Glu Leu Gly
                560                 565                 570
Glu Gly Ala Phe Gly Lys Val Phe Leu Ala Glu Cys Tyr Asn Leu
                575                 580                 585
Ser Pro Thr Lys Asp Lys Met Leu Val Ala Val Lys Ala Leu Lys
                590                 595                 600
Asp Pro Thr Leu Ala Ala Arg Lys Asp Phe Gln Arg Glu Ala Glu
                605                 610                 615
Leu Leu Thr Asn Leu Gln His Glu His Ile Val Lys Phe Tyr Gly
                620                 625                 630
Val Cys Gly Asp Gly Asp Pro Leu Ile Met Val Phe Glu Tyr Met
                635                 640                 645
Lys His Gly Asp Leu Asn Lys Phe Leu Arg Ala His Gly Pro Asp
                650                 655                 660
Ala Met Ile Leu Val Asp Gly Gln Pro Arg Gln Ala Lys Gly Glu
                665                 670                 675
Leu Gly Leu Ser Gln Met Leu His Ile Ala Ser Gln Ile Ala Ser
                680                 685                 690
Gly Met Val Tyr Leu Ala Ser Gln His Phe Val His Arg Asp Leu
                695                 700                 705
Ala Thr Arg Asn Cys Leu Val Gly Ala Asn Leu Leu Val Lys Ile
                710                 715                 720
Gly Asp Phe Gly Met Ser Arg Asp Val Tyr Ser Thr Asp Tyr Tyr
                725                 730                 735
Arg Val Gly Gly His Thr Met Leu Pro Ile Arg Trp Met Pro Pro
                740                 745                 750
```

```
Glu Ser Ile Met Tyr Arg Lys Phe Thr Thr Glu Ser Asp Val Trp
            755                 760                 765

Ser Phe Gly Val Ile Leu Trp Glu Ile Phe Thr Tyr Gly Lys Gln
            770                 775                 780

Pro Trp Phe Gln Leu Ser Asn Thr Glu Val Ile Glu Cys Ile Thr
            785                 790                 795

Gln Gly Arg Val Leu Glu Arg Pro Arg Val Cys Pro Lys Glu Val
            800                 805                 810

Tyr Asp Val Met Leu Gly Cys Trp Gln Arg Glu Pro Gln Gln Arg
            815                 820                 825

Leu Asn Ile Lys Glu Ile Tyr Lys Ile Leu His Ala Leu Gly Lys
            830                 835                 840

Ala Thr Pro Ile Tyr Leu Asp Ile Leu Gly
            845                 850

<210> SEQ ID NO 8
<211> LENGTH: 2940
<212> TYPE: DNA
<213> ORGANISM: Homo Sapien

<400> SEQUENCE: 8
tatagaataa catccacttt gcctttctct ccacaggtgt ccactcccag              50
gtccaactgc acctgaattc cactgccttc caccaagctc tgcaggatcc             100
cagagtcagg ggtctgtatc ttcctgctgg tggctccagt tcaggaacag             150
taaaccctgc tccgaatatt gcctctcaca tctcgtcaat ctccgcgagg             200
actggggacc ctgtgacaag cttcagcgcg aacgaccaac taccccgatc             250
atcagttatc cttaaggtct cttttgtgtg gtgcgttccg gtatgggggg             300
gactgccgcc aggttggggg ccgtgatttt gtttgtcgtc atagtgggcc             350
tccatggggt ccgcggcaaa tatgccttgg cggatgcctc tctcaagatg             400 gccgaccccca atcgatttcg cggcaaagac cttccggtcc tggaccagct            450
gctcgaggta tgccctgcaa attgtgtctg cagcaagact gagatcaatt             500
gccggcggcc ggacgatggg aacctcttcc ccctcctgga agggcaggat             550
tcagggaaca gcaatgggaa cgccaatatc aacatcacgg acatctcaag             600
gaatatcact tccatacaca tagagaactg gcgcagtctt cacacgctca             650
acgccgtgga catggagctc tacaccggac ttcaaaagct gaccatcaag             700
aactcaggac ttcggagcat tcagcccaga gcctttgcca agaaccccca             750
tttgcgttat ataaacctgt caagtaaccg gctcaccaca ctctcgtggc             800
agctcttcca gacgctgagt cttcgggaat gcagttgga gcagaacttt              850 ttcaactgca gctgtgacat ccgctggatg cagctctggc aggagcaggg             900
ggaggccaag ctcaacagcc agaacctcta ctgcatcaat gctgatggct             950
cccagcttcc tctcttccgc atgaacatca gtcagtgtga ccttcctgag            1000
atcagcgtga gccacgtcaa cctgaccgta cgagagggtg acaatgctgt            1050
tatcacttgc aatggctctg gatcacccct tcctgatgtg gactggatag            1100
tcactgggct gcagtccatc aacactcacc agaccaatct gaactggacc            1150
aatgttcatg ccatcaactt gacgctggtg aatgtgacga gtgaggacaa            1200
tggcttcacc ctgacgtgca ttgcagagaa cgtggtgggc atgagcaatg            1250
```

-continued

| | | |
|---|---|---|
| ccagtgttgc cctcactgtc tactatcccc cacgtgtggt gagcctggag | 1300 |
| gagcctgagc tgcgcctgga gcactgcatc gagtttgtgg tgcgtggcaa | 1350 |
| cccccccacca acgctgcact ggctgcacaa tgggcagcct ctgcgggagt | 1400 |
| ccaagatcat ccatgtggaa tactaccaag agggagagat ttccgagggc | 1450 |
| tgcctgctct tcaacaagcc cacccactac aacaatggca actataccct | 1500 |
| cattgccaaa aacccactgg gcacagccaa ccagaccatc aatggccact | 1550 |
| tcctcaagga gcccttccca gagagcacgg ataactttat cttgtttgac | 1600 |
| gaagtgagtc ccacacctcc tatcactgtg acccacaaac cagaagaaga | 1650 |
| cacttttggg gtatccatag cagttggact tgctgctttt gcctgtgtcc | 1700 |
| tgttggtggt tctcttcgtc atgatcaaca aatatggtcg acggtccaaa | 1750 |
| tttggaatga agggtcccgt ggctgtcatc agtggtgagg aggactcagc | 1800 |
| cagcccactg caccacatca accacggcat caccacgccc tcgtcactgg | 1850 |
| atgccgggcc cgacactgtg gtcattggca tgactcgcat ccctgtcatt | 1900 |
| gagaacccccc agtacttccg tcagggacac aactgccaca agccggacac | 1950 |
| gtatgtgcag cacattaaga ggagagacat cgtgctgaag cgagaactgg | 2000 |
| gtgagggagc ctttggaaag gtcttcctgg ccgagtgcta caacctcagc | 2050 |
| ccgaccaagg acaagatgct tgtggctgtg aaggccctga aggatcccac | 2100 |
| cctggctgcc cggaaggatt tccagaggga ggccgagctg ctcaccaacc | 2150 |
| tgcagcatga gcacattgtc aagttctatg gagtgtgcgg cgatgggac | 2200 |
| cccctcatca tggtctttga atacatgaag catggagacc tgaataagtt | 2250 |
| cctcagggcc catgggccag atgcaatgat ccttgtggat ggacagccac | 2300 |
| gccaggccaa gggtgagctg gggctctccc aaatgctcca cattgccagt | 2350 |
| cagatcgcct cgggtatggt gtacctggcc tcccagcact tgtgcaccg | 2400 |
| agacctggcc accaggaact gcctggttgg agcgaatctg ctagtgaaga | 2450 |
| ttggggactt cggcatgtcc agagatgtct acagcacgga ttattacagg | 2500 |
| gtgggaggac acaccatgct ccccattcgc tggatgcctc ctgaaagcat | 2550 |
| catgtaccgg aagttcacta cagagagtga tgtatggagc ttcggggtga | 2600 |
| tcctctggga gatcttcacc tatggaaagc agccatggtt ccaactctca | 2650 |
| aacacggagg tcattgagtg cattacccaa ggtcgtgttt tggagcggcc | 2700 |
| ccgagtctgc cccaaagagg tgtacgatgt catgctgggg tgctggcaga | 2750 |
| gggaaccaca gcagcggttg aacatcaagg agatctacaa aatcctccat | 2800 |
| gctttgggga aggccacccc aatctacctg gacattcttg gctagtggtg | 2850 |
| gctggtggtc atgaattaat tcaatcgatg gccgccatgg cccaacttgt | 2900 |
| ttattgcagc ttataatggt tacaaataaa gcaatagcat | 2940 |

<210> SEQ ID NO 9
<211> LENGTH: 5141
<212> TYPE: DNA
<213> ORGANISM: Artificial Sequence
<220> FEATURE:
<223> OTHER INFORMATION: Plasmid

<400> SEQUENCE: 9

-continued

| | |
|---|---|
| ttcgagctcg cccgacattg attattgact agagtcgatc gacagctgtg | 50 |
| gaatgtgtgt cagttagggt gtggaaagtc cccaggctcc ccagcaggca | 100 |
| gaagtatgca aagcatgcat ctcaattagt cagcaaccag gtgtggaaag | 150 |
| tccccaggct ccccagcagg cagaagtatg caaagcatgc atctcaatta | 200 |
| gtcagcaacc atagtcccgc ccctaactcc gcccatcccg ccctaactc | 250 |
| cgcccagttc cgcccattct ccgccccatg gctgactaat tttttttatt | 300 |
| tatgcagagg ccgaggccgc ctcggcctct gagctattcc agaagtagtg | 350 |
| aggaggcttt tttgaggcc taggcttttg caaaaagcta gcttatccgg | 400 |
| ccgggaacgg tgcattggaa cgcggattcc ccgtgccaag agtgacgtaa | 450 |
| gtaccgccta tagagcgata agaggatttt atccccgctg ccatcatggt | 500 |
| tcgaccattg aactgcatcg tcgccgtgtc ccaaaatatg gggattggca | 550 |
| agaacggaga cctaccctgg cctccgctca ggaacgagtt caagtacttc | 600 |
| caaagaatga ccacaacctc ttcagtggaa ggtaaacaga atctggtgat | 650 |
| tatgggtagg aaaacctggt tctccattcc tgagaagaat cgacctttaa | 700 |
| aggacagaat taatatagtt ctcagtagag aactcaaaga accaccacga | 750 |
| ggagctcatt ttcttgccaa agtttggat gatgccttaa gacttattga | 800 |
| acaaccggaa ttggcaagta agtagacat ggtttggata gtcggaggca | 850 |
| gttctgttta ccaggaagcc atgaatcaac caggccacct tagactcttt | 900 |
| gtgacaagga tcatgcagga atttgaaagt gacacgtttt tcccagaaat | 950 |
| tgatttgggg aaatataaac ctctcccaga atacccaggc gtcctctctg | 1000 |
| aggtccagga ggaaaaaggc atcaagtata agtttgaagt ctacgagaag | 1050 |
| aaagactaac aggaagatgc tttcaagttc tctgctcccc tcctaaagct | 1100 |
| atgcattttt ataagaccat gggacttttg ctggctttag atccccttgg | 1150 |
| cttcgttaga acgcggctac aattaataca taaccttatg tatcatacac | 1200 |
| atacgattta ggtgacacta tagataacat ccactttgcc tttctctcca | 1250 |
| caggtgtcca ctcccaggtc caactgcacc tcggttctaa gcttctgcag | 1300 |
| gtcgactcta gaggatcccc ggggaattca atcgatggcc gccatggccc | 1350 |
| aacttgttta ttgcagctta taatggttac aaataaagca atagcatcac | 1400 |
| aaatttcaca aataaagcat ttttttcact gcattctagt tgtggtttgt | 1450 |
| ccaaactcat caatgtatct tatcatgtct ggatcgatcg ggaattaatt | 1500 |
| cggcgcagca ccatggcctg aaataacctc tgaaagagga acttggttag | 1550 |
| gtaccttctg aggcggaaag aaccagctgt ggaatgtgtg tcagttaggg | 1600 |
| tgtggaaagt ccccaggctc cccagcaggc agaagtatgc aaagcatgca | 1650 |
| tctcaattag tcagcaacca ggtgtggaaa gtccccaggc tccccagcag | 1700 |
| gcagaagtat gcaaagcatg catctcaatt agtcagcaac catagtcccg | 1750 |
| cccctaactc cgcccatccc gcccctaact ccgcccagtt ccgcccattc | 1800 |
| tccgccccat ggctgactaa tttttttat ttatgcagag gccgaggccg | 1850 |
| cctcggcctc tgagctattc cagaagtagt gaggaggctt ttttggaggc | 1900 |
| ctaggctttt gcaaaaagct gttacctcga gcggccgctt aattaaggcg | 1950 |
| cgccatttaa atcctgcagg taacagcttg gcactggccg tcgttttaca | 2000 |

-continued

```
acgtcgtgac tgggaaaacc ctggcgttac ccaacttaat cgccttgcag      2050
cacatccccc cttcgccagc tggcgtaata gcgaagaggc ccgcaccgat      2100
cgcccttccc aacagttgcg tagcctgaat ggcgaatggc gcctgatgcg      2150
gtattttctc cttacgcatc tgtgcggtat ttcacaccgc atacgtcaaa      2200
gcaaccatag tacgcgccct gtagcggcgc attaagcgcg gcgggtgtgg      2250
tggttacgcg cagcgtgacc gctacacttg ccagcgccct agcgcccgct      2300
cctttcgctt tcttcccttc ctttctcgcc acgttcgccg gctttccccg      2350
tcaagctcta atcgggggc tccctttagg gttccgattt agtgctttac       2400
ggcacctcga ccccaaaaaa cttgatttgg gtgatggttc acgtagtggg      2450
ccatcgccct gatagacggt ttttcgccct ttgacgttgg agtccacgtt      2500
ctttaatagt ggactcttgt tccaaactgg aacaacactc aaccctatct      2550
cgggctattc ttttgattta taagggattt tgccgatttc ggcctattgg      2600
ttaaaaaatg agctgattta acaaaaattt aacgcgaatt ttaacaaaat      2650
attaacgttt acaattttat ggtgcactct cagtacaatc tgctctgatg      2700
ccgcatagtt aagccaactc cgctatcgct acgtgactgg gtcatggctg      2750
cgccccgaca cccgccaaca cccgctgacg cgccctgacg ggcttgtctg      2800
ctcccggcat ccgcttacag acaagctgtg accgtctccg ggagctgcat      2850
gtgtcagagg ttttcaccgt catcaccgaa acgcgcgagg cagtattctt      2900
gaagacgaaa gggcctcgtg atacgcctat ttttataggt taatgtcatg      2950
ataataatgg tttcttagac gtcaggtggc acttttcggg gaaatgtgcg      3000
cggaacccct atttgtttat ttttctaaat acattcaaat atgtatccgc      3050
tcatgagaca ataaccctga taaatgcttc aataatattg aaaaaggaag      3100
agtatgagta ttcaacattt ccgtgtcgcc cttattccct ttttttgcggc     3150 attttgcctt cctgtttttg ctcacccaga aacgctggtg aaagtaaaag      3200
atgctgaaga tcagttgggt gcacgagtgg gttacatcga actggatctc      3250
aacagcggta agatccttga gttttcgc cccgaagaac gttttccaat        3300
gatgagcact tttaaagttc tgctatgtgg cgcggtatta tcccgtgatg      3350
acgccgggca agagcaactc ggtcgccgca tacactattc tcagaatgac      3400
ttggttgagt actcaccagt cacagaaaag catcttacgg atggcatgac      3450
agtaagagaa ttatgcagtg ctgccataac catgagtgat aacactgcgg      3500
ccaacttact tctgacaacg atcggaggac cgaaggagct aaccgctttt      3550
ttgcacaaca tgggggatca tgtaactcgc cttgatcgtt gggaaccgga      3600
gctgaatgaa gccataccaa acgacgagcg tgacaccacg atgccagcag      3650
caatggcaac aacgttgcgc aaactattaa ctggcgaact acttactcta      3700
gcttcccggc aacaattaat agactggatg gaggcggata agttgcagg       3750 accacttctg cgctcggccc ttccggctgg ctggtttatt gctgataaat      3800
ctggagccgg tgagcgtggg tctcgcggta tcattgcagc actggggcca      3850
gatggtaagc cctcccgtat cgtagttatc tacacgacgg ggagtcaggc      3900
aactatggat gaacgaaata gacagatcgc tgagataggt gcctcactga      3950
```

| | |
|---|---|
| ttaagcattg gtaactgtca gaccaagttt actcatatat actttagatt | 4000 |
| gatttaaaac ttcattttta atttaaaagg atctaggtga agatcctttt | 4050 |
| tgataatctc atgaccaaaa tcccttaacg tgagttttcg ttccactgag | 4100 |
| cgtcagaccc cgtagaaaag atcaaaggat cttcttgaga tcctttttt | 4150 |
| ctgcgcgtaa tctgctgctt gcaaacaaaa aaaccaccgc taccagcggt | 4200 |
| ggtttgtttg ccggatcaag agctaccaac tcttttttccg aaggtaactg | 4250 |
| gcttcagcag agcgcagata ccaaatactg tccttctagt gtagccgtag | 4300 |
| ttaggccacc acttcaagaa ctctgtagca ccgcctacat acctcgctct | 4350 |
| gctaatcctg ttaccagtgg ctgctgccag tggcgataag tcgtgtctta | 4400 |
| ccgggttgga ctcaagacga tagttaccgg ataaggcgca gcggtcgggc | 4450 |
| tgaacggggg gttcgtgcac acagcccagc ttggagcgaa cgacctacac | 4500 |
| cgaactgaga tacctacagc gtgagcattg agaaagcgcc acgcttcccg | 4550 |
| aagggagaaa ggcggacagg tatccggtaa gcggcagggt cggaacagga | 4600 |
| gagcgcacga gggagcttcc agggggaaac gcctggtatc tttatagtcc | 4650 |
| tgtcgggttt cgccacctct gacttgagcg tcgatttttg tgatgctcgt | 4700 |
| caggggggcg gagcctatgg aaaaacgcca gcaacgcggc ctttttacgg | 4750 |
| ttcctggcct tttgctggcc ttttgctcac atgttctttc ctgcgttatc | 4800 |
| ccctgattct gtggataacc gtattaccgc ctttgagtga gctgataccg | 4850 |
| ctcgccgcag ccgaacgacc gagcgcagcg agtcagtgag cgaggaagcg | 4900 |
| gaagagcgcc caatacgcaa accgcctctc cccgcgcgtt ggccgattca | 4950 |
| ttaatccagc tggcacgaca ggtttcccga ctggaaagcg ggcagtgagc | 5000 |
| gcaacgcaat taatgtgagt tacctcactc attaggcacc ccaggcttta | 5050 |
| cactttatgc ttccggctcg tatgttgtgt ggaattgtga gcggataaca | 5100 |
| atttcacaca ggaaacagct atgaccatga ttacgaatta a | 5141 |

<210> SEQ ID NO 10
<211> LENGTH: 103
<212> TYPE: DNA
<213> ORGANISM: Artificial Sequence
<220> FEATURE:
<223> OTHER INFORMATION: Synthetic oligonucleotide

<400> SEQUENCE: 10

| | |
|---|---|
| tgcagcaagg gctactgcca cactcgagct gcgcagatgc tagcctcaag | 50 |
| atggctgatc caaatcgatt ccgcggcaaa gatcttccgg tcctgtagaa | 100 |
| gct | 103 |

<210> SEQ ID NO 11
<211> LENGTH: 103
<212> TYPE: DNA
<213> ORGANISM: Artificial Sequence
<220> FEATURE:
<223> OTHER INFORMATION: Synthetic Oligonucleotide

<400> SEQUENCE: 11

-continued

| | |
|---|---|
| agcttctaca ggaccggaag atctttgccg cggaatcgat ttggatcagc | 50 |
| catcttgagg ctagcatctg cgcagctcga gtgtggcagt agcccttgct | 100 |
| gca | 103 |

KINASE RECEPTOR ACTIVATION ASSAY

This is a continuation of application Ser. No. 08/374,565 filed Jan. 20, 1995, now U.S. Pat. No. 6,025,745, which is a 371 of PCT/US94/13329, filed Nov. 18, 1994, which is a CIP of 08/157,563 filed Nov. 23, 1993, now abandoned, which is a CIP of 08/170,558 filed Dec. 20, 1993, now U.S. Pat. No. 6,001,621, and is a CIP of 08/286,305 filed Aug. 5, 1995, now U.S. Pat. No. 5,766,863.

BACKGROUND OF THE INVENTION

1. Field of the Invention

This invention relates to a kinase receptor activation (KIRA) assay. In particular, the invention relates to an assay for measuring autophosphorylation of the kinase domain of a receptor protein tyrosine kinase (rPTK) using a kinase receptor activation, enzyme-linked immunosorbent assay (KIRA ELISA).

2. Description of Related Art

One mechanism for signal transduction in animals involves protein phosphorylation. Protein phosphorylation involves the action of protein kinase, an enzyme that transfers a phosphate group from a phosphate donor onto an acceptor amino acid in a substrate protein. Protein phosphatases provide a means for reversing the signal when the stimulus is removed.

Protein kinases have multiple substrates, and classification of the protein kinases is based on the acceptor amino acid specificity. The two most well characterized protein kinases are the protein kinases with a protein alcohol group as acceptor called protein serine/threonine kinases and the protein kinases with a protein phenolic group as acceptor called protein tyrosine kinases (Hunter, *Methods in Enzymology* 200:3–9[1991]).

The most well known type of signal-transducing protein kinases are growth factor receptor protein tyrosine kinases (rPTKs). rPTKs usually comprise a large, glycosylated, extracellular ligand binding domain (ECD) and an intracellular domain (ICD) which contains a tyrosine kinase catalytic domain. A single hydrophobic transmembrane (TM) domain connects the ECD and ICD. Examples of rPTKs include the insulin receptor, epidermal growth factor receptor (EGF-R), platelet-derived growth factor receptor (PDGF-R), insulin-like growth factor 1 receptor (IGF-1-R), and the HER2 receptor, to name a few. See, for example, Ullrich and Schlessinger *Cell* 61:203–212 (1990) and Fantl et al., *Annu. Rev. Biochem* 62:453–481 (1993). rPTKs can phosphorylate exogenous protein substrates and intrinsic tyrosine residues via their catalytic tyrosine kinase domain. The intrinsic tyrosine residues normally reside in the ICD of the rPTK (see FIG. 1 herein). Activation of the intracellular kinase domain of rPTKs appears to be mediated by receptor oligomerization which results from the conformational alteration of the ECD upon ligand binding thereto. See Ullrich and Schlessinger, supra.

Serine-threonine kinases have also been disclosed in the literature. While most of the known protein serine-threonine kinases are cytoplasmic proteins, a family of mammalian transmembrane receptors with serine-threonine kinase domains has recently been found. Members of this receptor family have been described as binding TGF-β's and activin. For reviews of serine-threonine kinases, see Sale, G., *Biochem, Soc, Transactions* 20: 664–670 (1992); ten Dijke et al., *Prog. in Growth Factor Res*, 5: 55–72 (1994); and Mathews, L., *Endoc. Rev.* 15(3): 310–325 (1994).

Various assays have been developed which measure tyrosine kinase activity. Some of these assays measure the ability of a tyrosine kinase enzyme to phosphorylate a synthetic substrate polypeptide. For example, an assay has been developed which measures growth factor-stimulated tyrosine kinase activity by measuring the ability of the kinase to catalyze the transfer of the γ-phosphate of ATP to a suitable acceptor substrate. See Pike, L., *Methods of Enzymology* 146:353–362 (1987) and Hunter, *Journal of Biological Chemistry* 257(9):4843–4848 (1982), for example. In this assay, the use of [γ-$^{32}$P]ATP permits the radioactive labeling of the phosphorylated substrate, which is a synthetic tyrosine-containing peptide. Others have described protein kinase assays wherein incorporation of $^{32}$P into a tyrosine kinase receptor, such as the EGF receptor (see Donato et al., *Cell Growth Differ.* 3:259–268 [1992]), insulin receptor (see Kasuga et al., *Journal of Biological Chemistry* 257(17):9891–9884 [1982] and Kasuga et al., *Methods in Enzymology* 109:609–621 [1985]), and liver growth hormone receptor (see Wang et al., *Journal of Biological Chemistry* 267(24):17390–17396 [1992]), is measured.

The discovery of anti-phosphotyrosine antibodies has provided a non-radioactive, alternative means for measuring phosphorylation of tyrosine residues. For example, White and Backer (*Methods in Enzymology* 201:65–67 [1991]) mention polyclonal antibodies which selectively bind to phosphotyrosine and are considered to be useful for studying rPTKs. An anti-phosphotyrosine monoclonal antibody was used in one of the assays referred to in Madden et al. (*Anal Biochem* 199:210–215 [1991]), which measured phosphatase activity toward the insulin receptor. Anti-phosphotyrosine antibodies were also used by Cleaveland et al., in their protein tyrosine kinase ELISA assay. See Cleaveland et al., *Analytical Biochemistry* 190:249–253 (1990). The method of Cleaveland et al. utilizes purified high-activity oncogene tyrosine kinases, v-src and v-fps, and measures the ability of these tyrosine kinases to phosphorylate synthetic polymeric substrates which are coated on an ELISA microtiter plate. The phosphotyrosine produced by src-induced phosphorylation of the polymeric substrate is then quantitated by addition of an anti-phosphotyrosine antibody, the presence of which is detected using a second rabbit anti-mouse antibody which is linked to a reporter enzyme, horseradish peroxidase (HRPO). A similar ELISA assay has been developed by Lazaro et al., which is used for detection of a protein tyrosine kinase. See Lazaro et al., *Analytical Biochemistry* 192:257–261 (1991). Like the assay of Cleaveland et al., this assay also measures the ability of a protein tyrosine kinase to phosphorylate a synthetic substrate which is bound to microELISA wells.

A direct way to assess specific activation of rPTKs is by analysis of receptor autophosphorylation. See, e.g., Hunter and Cooper *Ann Rev Biochem* 54:897–930 (1985) and Ullrich and Schlessinger, *Cell* 61:203–212 (1990). Using this direct approach, Knutson and Suck disclose assays for measuring autophosphorylation of the insulin receptor under in situ or in vitro conditions (*Archives of Biochemistry and Biophysics* 285(2):197–204 [1991]). In the in situ assay, monolayer cultures of embryonic mouse 3T3-C2 fibroblasts (having the endogenous insulin receptor) are incubated with insulin in large cell culture dishes. Following incubation, the insulin receptor is extracted from the membranes. To achieve extraction of the insulin receptor, the cell monolayers are scraped into a buffer containing protease inhibitors and the cells are then disrupted in a homogenizer. The cellular homogenate is subsequently subjected to centrifugation for 60 min., and the pellet which forms is extracted into buffer containing detergent. Following a further centrifugation step, the supernatant (containing the insulin receptor) is incubated with an anti-insulin receptor antibody. Then, the receptor-antibody complex is incubated with protein A-agarose and unoccupied protein A sites are blocked with normal rabbit IgG. The agarose beads are then centrifuged, the supernatants aspirated and the pellets are re-suspended in buffer containing the radiolabelled anti-phosphotyrosine antibody. The amount of bound iodinated anti-phosphotyrosine antibody is consequently measured.

Klein and his colleagues discuss an assay for measuring insulin activation of the insulin receptor (Klein et al., *Diabetes* 42:883–890 [1993]). In this assay, aliquots of a heterogeneous population of mononuclear blood cells (including T cells, B cells, macrophages etc) having the insulin receptor are exposed to insulin in centrifuge tubes. The cells are then lysed in detergent using a motordriven homogenizer and the lysates are concentrated two- to four-fold using vacuum centrifugation. Sometimes, the insulin receptor is also partially purified using wheat germ agglutin agarose. The supernatants which form following centrifugation, are then transferred to anti-insulin receptor-coated microtiter plates. Insulin (8.7 nM) as well as kinase and phosphatase inhibitors are present during receptor immobilization in order to optimize the percentage of receptors captured to the microtiter plates. Activation of the insulin receptor is then measured by transphosphorylation of the substrate Poly-Glu,Tyr with $^{32}$P labeled ATP. The supernatants are then spotted onto absorbent paper and the paper is washed with cold TCA to remove unbound $^{32}$P-ATP. Remaining $^{32}$P-labeled Poly-Glu,Tyr on the washed absorbent paper is subsequently counted by scintillation counting.

Hagino et al. were also interested in studying the insulin receptor in patients (Hagino et al., *Diabetes* 43:274–280 [1994]). As a first step in the assay, Hagino et al. stimulate a primary cell suspension, which is not particularly homogeneous with respect to cell type. In particular, heparinized blood (1 ml washed twice with medium and resuspended in 1 ml of medium containing bovine serum albumin, BSA) is exposed to varying concentrations of insulin. The autophosphorylation reaction is stopped, the cells centrifuged for 30 min, the supernatant is discarded and the erythrocyte ghosts thus obtained are resuspended in buffer and centrifuged again. The pellet thereby obtained is adjusted to 500 μl and solubilized in detergent. The solubilized materials are then centrifuged and the resulting supernatant is subjected to sandwich ELISA (using anti-insulin receptor antibodies to capture the insulin receptor) to determine the extent of insulin receptor autophosphorylation.

King et al. in Life Sciences 53: 1465–1472 (1993) describe a calorimetric assay for examining inhibitors of the epidermal growth factor (EGF) receptor-associated tyrosine kinase in human intact epidermal A431 cells.

Several others have used an enzyme-conjugated form of the anti-phosphotyrosine antibody in Western blot analyses which measure receptor autophosphorylation. Briefly, Western blotting generally involves electrophoresing activated rPTK on polyacrylamide gel. The rPTK is then transferred to nitrocellulose and immunoblotted with the anti-phosphotyrosine antibody which is labelled to enable detection. See, for example, Wang, *Molecular and Cellular Biology* 5(12):3640–3643 (1985); Glenney et al., *Journal of Immunological Methods* 109:277–285 (1988); Kamps, *Methods in Enzymology* 201:101–110 (1991); Kozma et al., *Methods in Enzymology* 201:28–43 (1991); Holmes et al., *Science* 256:1205–10 (1992); and Corfas et al., *PNAS, USA* 90:1624–1628 (1993). However, with Western blot analysis, accurate quantitation can be very tedious. Furthermore, this technique tends to be time- consuming and generally does not allow high sample throughput.

It is an object of the instant invention to provide a sensitive, reliable assay that measures receptor protein tyrosine kinase (rPTK) autophosphorylation. The assay is desirably useful for qualitatively and quantitatively measuring kinase activation as well as facilitating identification and characterization of potential agonists and antagonists for a selected rPTK. It is a further object of the invention to provide an assay which enables ligand-receptor interactions to be studied for any selected rPTK.

This assay must have a capacity for high throughput, that is, the ability to reliably evaluate large numbers of samples in a relatively short period of time (e.g., in one day). The assay ideally does not use radioactive materials and is also amenable to automation.

It is a further object, in at least one embodiment of the invention, to provide a generic assay which enables a rPTK of interest to be studied, regardless of whether or not a receptor-specific capture agent having the desired characteristics is available. Furthermore, it is an object of the invention to provide an assay which substantially represents the activity of the tyrosine kinase receptor in situ. This is desirable insofar as it reduces the possibility that altered interactions between the receptor and the ligand may occur as a consequence of the receptor not being membrane-bound. Furthermore, if the receptor is a multimeric complex, this assay enables the correctly assembled receptor to be studied. It is an additional object to provide a method for measuring serine-threonine kinase phosphorylation, phosphorylation of intracellular kinases and phosphatase activity.

These and other objects will be apparent to the ordinary artisan upon consideration of the specification as a whole.

SUMMARY OF THE INVENTION

Accordingly, the invention provides an assay for measuring activation (i.e., autophosphorylation) of a tyrosine kinase receptor of interest.

The assay can be divided into two major stages, each of which is generally performed in separate assay plates. The first stage of the assay involves activating the receptor and is termed the kinase receptor activation (KIRA) stage of the assay. The second stage of the assay involves measuring receptor activation. Conveniently, this is achieved using an enzyme-linked immunosorbent assay (ELISA) to measure receptor activation.

The KIRA stage of the assay involves activating a tyrosine kinase receptor which is located in the cell membrane of an eukaryotic cell such that the extracellular domain of the receptor faces the external milieu of the cell, the transmembrane domain is located in the cell membrane and the kinase domain is located intracellularly. This stage of the overall assay involves steps (a) to (c) below:

(a) The first solid phase (e.g., a well of a first assay plate) is coated with a substantially homogeneous population of cells (usually a mammalian cell line) so that the cells adhere to the solid phase. Often, the cells are adherent and thereby adhere naturally to the first solid phase. In one embodiment of the invention, the cells have an endogenous tyrosine kinase receptor presented in the cell membrane as discussed above. In an alternative embodiment, the cells have been transformed with DNA encoding a tyrosine kinase receptor or a "receptor construct" defined further below, which DNA is expressed by the cells such that the receptor or receptor construct is suitably positioned in the cell membranes thereof.

The receptor construct comprises a fusion of a kinase receptor and a flag polypeptide. The flag polypeptide is recognized by the capture agent, often a capture antibody, in the ELISA part of the assay. Use of a receptor construct as disclosed herein is particularly advantageous since it provides a "generic" assay wherein autophosphorylation of any tyrosine kinase receptor can be measured, regardless of whether or not a receptor-specific capture agent having the required characteristics is available. Often, the tyrosine kinase receptor is a fusion protein comprising the ECD of a selected tyrosine kinase and the catalytic ICD (and possibly the transmembrane domain) of another well characterized tyrosine kinase (e.g., the Rse receptor).

(b) An analyte is then added to the wells having the adhering cells, such that the tyrosine kinase receptor is exposed to (or contacted with) the analyte. This assay enables identification of agonist and antagonist ligands for the tyrosine kinase receptor of interest. In order to detect the presence of an antagonist ligand which blocks binding and/or activation of the receptor by an agonist ligand, the adhering cells are exposed to the suspected antagonist ligand first and then to the agonist ligand (or to a mixture of the agonist and antagonist) so that competitive inhibition of receptor binding and activation can be measured. Also, the assay can identify an antagonist which binds to the agonist ligand and thereby reduces or eliminates its ability to bind to, and activate, the rPTK. To detect such an antagonist, the suspected antagonist and the agonist for the rPTK are incubated together and the adhering cells are then exposed to this mixture of ligands.

(c) Following exposure to the analyte, the adhering cells are solubilized using a lysis buffer (which has a solubilizing detergent therein) and gentle agitation, thereby releasing cell lysate which can be subjected to the ELISA part of the assay directly, without the need for concentration or clarification of the cell lysate. Thus, this assay provides a significant improvement over assays described by Knutson and Buck, supra, Klein et al., supra, and Hagino et al., supra, insofar as it is surprisingly unnecessary to concentrate the cell lysate prior to the ELISA. Furthermore, unlike the other assays, in the instant assay the cells can be lysed in lysis buffer using gentle agitation without the need for homogenizing, centrifuging or clarifying the cells. The cell lysate thus prepared is then ready to be subjected to the ELISA stage of the assay. It has been discovered that, surprisingly, the first assay plate can be stored at freezing temperatures (i.e., at about −20° to −70° C.) for significant periods of time (at least 6 months) before the ELISA stage of the assay. This is a significant finding insofar as the KIRA and ELISA stages of the assay can be performed on separate days.

The ELISA component of the assay comprises steps (d) to (h), described below.

(d) As a first step, the second solid phase (usually a well of an ELISA microtiter plate) is coated with a capture agent (often a capture antibody) which binds specifically to the tyrosine kinase receptor, or, in the case of a receptor construct, to the flag polypeptide. Coating of the second solid phase is carried out so that the capture agent adheres to the second solid phase. The capture agent is generally a monoclonal antibody, but, as is described in the examples herein, polyclonal antibodies may also be used.

(e) The cell lysate obtained in step (c) of the above-mentioned KIRA stage of the assay is exposed to, or contacted with, the adhering capture agent so that the receptor or receptor construct adheres to (or is captured in) the second solid phase. Unlike the assay of Klein et al., the instant assay does not require the ligand for the receptor as well as kinase inhibitors to be present to achieve suitable immobilization of the receptor or receptor construct to the second solid phase.

(f) A washing step is then carried out, so as to remove unbound cell lysate, leaving the captured receptor or receptor construct.

(g) The adhering or captured receptor or receptor construct is then exposed to, or contacted with, an anti-phosphotyrosine antibody which identifies phosphorylated tyrosine residues in the tyrosine kinase receptor. In the preferred embodiment, the anti-phosphotyrosine antibody is conjugated (directly or indirectly) to an enzyme which catalyses a color change of a non-radioactive color reagent. Accordingly, phosphorylation of the receptor can be measured by a subsequent color change of the reagent. The enzyme can be bound to the anti-phosphotyrosine antibody directly, or a conjugating molecule (e.g., biotin) can be conjugated to the anti-phosphotyrosine antibody and the enzyme can be subsequently bound to the anti-phosphotyrosine antibody via the conjugating molecule.

(h) Finally, binding of the anti-phosphotyrosine antibody to the captured receptor or receptor construct is measured, e.g., by a color change in the color reagent.

The invention also pertains to a Rse.flag reagent which is particularly useful for use in the KIRA ELISA assay. The Rse.flag reagent is a polypeptide comprising a fusion of a flag polypeptide (usually the gD flag described herein) to the carboxyl terminus of the intracellular domain of the Rse rPTK. Generally, the tranemembrane domain of Rae and the extracellular domain of another rPTK of interest are also present in the fusion polypeptide reagent. The nucleic acid encoding this reagent and a cell transformed therewith are also claimed.

In yet a further aspect, the invention relates to a kit which can be used in the KIRA ELISA disclosed above which comprises an anti-flag polypeptide capture agent (e.g. a capture antibody) which is usually bound to the second solid phase as described herein. Thus, the kit generally provides an ELISA microtiter plate having an anti-flag polypeptide capture antibody adhering to a well thereof. Optionally, the kit also provides an anti-phosphotyrosine antibody which is often labelled, or reagents for labelling the anti-phosphotyrosine antibody are supplied with the kit. Sometimes, a homogeneous population of cells which have been transformed with a receptor construct as described herein are also provided with the kit. The kit also suitably includes instructions for carrying out the KIRA ELISA.

BRIEF DESCRIPTION OF THE DRAWINGS

FIGS. 1A–1C are diagrammatic representations of Roe.gD (FIG. 1A), Receptor ECD/Rse.gD chimera (FIG. 1B) and a CHO cell transformed with the Receptor ECD/Rse.gD chimera (FIG. 1C).

FIGS. 2A and 2B depict an alignment of the amino acid sequence (SEQ ID NO: 1) and nucleotide sequence (SEQ ID NO: 2) of Rse.gD. The residues of the signal sequence are indicated with an (*), the transmembrane domain of Rse is boxed and the ECD and ICD of Rse are also delineated. The residues of the gD flag sequence are underlined.

FIG. 3 is a flow diagram of an exemplary strategy for selecting a suitable capture agent for use in the assay.

FIG. 4 is a flow diagram of an exemplary strategy for selecting a transformed cell suitable for use in the assay, where the cell has a receptor construct with an amino-terminal flag polypeptide located in the cell membrane thereof.

FIG. 5 is a flow diagram of an exemplary strategy for selecting a transformed cell suitable for use in the assay, where the cell has a receptor construct with a carboxyl-terminal flag polypeptide located in the cell membrane thereof.

FIG. 6 is a flow chart and cartoon illustrating the KIRA ELISA assay for the HER2 receptor described in Example 1.

FIG. 7 depicts a p185$^{HER2}$/HRGβ1$_{177}$-244 KIRA ELISA standard curve obtained using the assay described in Example 1. To obtain the standard curve, MCF-7 cells (2×10$^5$) were stimulated with 3000, 1000, 333, 111, 37, 12, 4, or 0 pM HRGβ1$_{127-244}$, as determined by quantitative amino acid analysis (q.a.a.a.). Each calibrator concentration was run in triplicate.

The values derived from 10 such standard curves were averaged (total n+(3) and are presented as mean ABS$_{450/650}$ ±sd ad vs. HRGβ1$_{117-244}$ concentration.

FIG. 8 depicts heregulin specificity of p185$^{HER2}$/HRG KIRA ELISA of Example 1. In the assay, MCF-7 cells (2×10$_5$) were stimulated with either HRGβ1$_{117-244}$ (■) at 3000, 1000, 333, 111, 37, 12, 4 or 0 pM or IGF-1(▲), EGF (□), VEGF (●) or insulin (♦) at 30000, 10000, 3333, 1111, 370, 120, 40 or 0 pM. For all concentrations of ligands, n=3 and data are presented as average ABS$_{450/650}$ ±sd vs. ligand concentration.

FIG. 9 is a flow chart and cartoon illustrating the KIRA ELISA assay for the Rse receptor described in Example 2.

FIG. 10 depicts a Rse KIRA ELISA standard curve obtained using the assay described in Example 2. To obtain the standard curve, CHO cells transformed with the Rse.gD construct were stimulated with 1:100, 1:200, 1:400, 1:800, 1:1600, 1:3200 or 0 diluted, anti-Roe agonist antibody. Each calibrator concentration was run in triplicate. The values are presented as mean ABS$_{450/650}$ ±ad vs. 1/dilution agonist antibody.

FIG. 11 is a flow chart and cartoon illustrating the KIRA ELISA assay for the trk receptors (i.e., trk A, trk B, and trk C) described in Example 3.

FIGS. 12A–12D depict an alignment of the amino acid acid sequence (SEQ ID NO: 3) and nucleotide sequence (SEQ ID NO: 4) of gD.trk A used in the assay described in Example 3. The residues of the signal sequence are indicated with an (*), the residues of the gD flag sequence are underlined, the residues of the transmembrane domain of trk A are in bold and the ECD and ICD thereof are also delineated.

FIGS. 13A–13D depict an alignment of the amino acid sequence (SEQ ID NO: 5) and nucleotide sequence (SEQ ID NO: 6) of gD.trk B used in the assay described in Example 3. The residues of the signal sequence are indicated with an (*), the residues of the gD flag sequence are underlined, the residues of the transmembrane domain of trk B are in bold and the ECD and ICD thereof are also delineated.

FIGS. 14A–14D depict an alignment of the amino acid sequence (SEQ ID NO: 7) and nucleotide sequence (SEQ ID NO: 8) of gD.trk C used in the assay described in Example 3. The residues of the signal sequence are indicated with an (*), the residues of the gD flag sequence are underlined, the residues of the transmembrane domain of trk C are in bold and the ECD and ICD thereof are also delineated.

FIGS. 15A–15C depict standard curves for trk A, B and C, respectively, which were obtained using the assay described in Example 3. To obtain the standard curves, CHO cells transformed with the gD.trk constructs were stimulated with 3000, 1000, 333, 111, 37, 12, 4 or 0 pM of ligand, i.e. nerve growth factor (NGF, ■), neurotrophin 3 (NT3, ●) or neurotrophin 5 (NT5, ▲). The values are presented as mean ABS$_{450/650}$ ±sd vs. ligand concentration.

FIGS. 16A–16L depict the nucleotide sequence (SEQ ID NO: 9) of the pSVI17.ID.LL expression vector used for expression of Rse.gD in Example 2.

FIG. 17 is a diagrammatic representation of the MPL/Rse.gD chimeric receptor described in Example 4.

FIG. 18 is a flow chart and cartoon illustrating the KIRA ELISA for the MPL/Rse.gD chimeric receptor described in Example 4.

DETAILED DESCRIPTION OF THE PREFERRED EMBODIMENTS

1. Abbreviations and Definitions

"rPTK" means a receptor protein tyrosine kinase.

"ECD", "TM domain" and "ICD" refer to the extracellular domain, transmembrane domain and intracellular domain of a rPTK, respectively.

"Kinase Receptor Activation" or "KTIRA" when used throughout this application refers to the first stage of the instantly claimed assay wherein a cell-bound rPTK is exposed to a potential agonist/antagonist ligand which may (or may not) induce phosphorylation of tyrosine residues in the intracellular domain of the rPTK. The KIRA is generally carried out in the "first assay plate" as defined herein.

"Enzyme-Linked Immunosorbent Assay" or "ELISA" refers to the second stage of the instantly claimed assay and involves measuring tyrosine phosphorylation of the rPTK. The ELISA is normally carried out in the "second assay plate" as disclosed in this application. The ELISA is a "sandwich ELISA" insofar as it involves capturing the rPTK or receptor construct to the second solid phase (usually the well of an ELISA microtiter plate). ELISA assays generally involve the preparation of enzyme-antibody conjugates. The conjugated enzyme cleaves a substrate to generate a colored reaction product that can be detected spectrophotometrically. In this assay, the absorbance of the colored solution in individual microtiter wells is proportional to the amount of phosphotyrosines. A review of ELISA is found in *Current Protocols in Molecular Biology*, Vol. 2, chapter 11 (1991). While the term "ELISA" is used to describe the second stage of the instant assay, it is only a preferred embodiment of the invention, since, as disclosed herein, techniques other than enzymatic detection are available for measuring binding of the anti-phosphotyrosine antibody to the activated receptor.

The terms "receptor", "kinase receptor", "tyrosine kinase", "tyrosine kinase receptor", "receptor protein tyrosine kinase" and "rPTK" are used interchangeably herein and refer to a protein having at least one phosphate accepting phenolic group. The protein is usually a receptor insofar as it has a ligand-binding ECD, TM domain and ICD. The ICD usually comprises a catalytic kinase domain and has one or more phosphate accepting tyrosine residues. See FIGS. 1A and 1B, for example. Examples of tyrosine kinase receptors include the insulin receptor, insulin related receptor, epidermal growth factor receptor (EGF-R), platelet-derived growth factor receptors A and B (PDGF-R-A and PDGF-R-B), insulin-like growth factor 1 receptor (IGF-1-R), macrophage colony-stimulating factor receptor (M-CSF-R), HER2/neu/c-erbB-2 receptor, HER3/c-erbB-3 receptor, Xmrk receptor, IRR receptor, fibroblast growth factor (FGF) receptors bek and flg, c-kit receptor, Flk/kDR receptor, Rse receptor, the Eph, Elk, Eck, Eek, Erk, Cek4/Mek4/HEK and Cek5 receptors, Ax1 receptor, hepatocyte growth factor receptor (HGF-R), Flt1 VEGF receptor, SAL-S1 receptor, HpTK 5 receptor, trka receptor, trkb receptor, and trkc receptor. See, for example, Ullrich and Schlessinger Cell 81:203–212 (1990); Fantl et al., Annu. Rev. Biochem. 62:453–481 (1993); Mark et al., Journal of Biolocical Chemistry 269(14):10720–10728 (1994); and WO 93/15201.

The terms mentioned above encompass chimeric "receptor" molecules which comprise at least the extracellular domain of a selected tyrosine kinase and the intracellular domain, and optionally, the transmembrane domain of another tyrosine kinase. Of course, the tyrosine kinase of interest can provide the transmembrane domain and/or intracellular domain. The terms also encompass amino acid sequence variants and covalent derivatives of the various rPTKs provided they still display tyrosine kinase phosphorylation activity in the KIRA ELISA. Therefore, the variants will general have conservative amino acid alterations. The individual domains of the tyrosine kinase can be delineated based on sequence homology to known tyrosine kinases and hydrophobicity plots. For example, the hydrophobic transmembrane domain can be readily determined and the ECD and ICD are usually amino-terminal and carboxyl terminal to the transmembrane domain, respectively. Conveniently, the transmembrane domain and ICD of the Rse receptor can be fused to the ECD of a tyrosine kinase of interest, thereby forming a chimeric receptor which is encompassed by the terms denoting a receptor as mentioned above.

In the preferred embodiment, the rPTK is selected from the group consisting of HER2 receptor (Ullrich and Schlessinger, sugra), Rse receptor (Mark et al., supra and SEQ ID NO: 1), trk A receptor (SEQ ID NO: 3), trk B receptor (SEQ ID NO: 5) and trk C receptor (SEQ ID NO: 7).

By "autophosphorylation" is meant activation of the catalytic kinase domain of the rPTK, whereby at least one intrinsic tyrosine residue is phosphorylated. Generally, autophosphorylation will result when an agonist molecule binds to the extracellular domain of the kinase receptor. Without being limited to any particular mechanism of action, it is thought that binding of the agonist molecule may result in oligomerization of the kinase receptor which causes activation of the catalytic kinase domain.

By "solid phase" is meant a non-aqueous matrix to which the cells (in the KIRA stage of the assay) or the capture agent (in the ELISA stage of the assay) can adhere. Usually, the solid phase comprises the well of an assay plate but the invention is by no means limited to this embodiment. For example, the solid phase can comprise a discontinuous solid phase of discrete particles. The particles can be porous and formed from a number of different materials, e.g., polysaccharides (e.g. agarose), polyacrylamides, polystyrene, polyvinyl alcohol, silicones and glasses. For examples of suitable particulate solid phases, see U.S. Pat. No. 4,275, 149.

By "well" is meant a recess or holding space in which an aqueous sample can be placed. The well is provided in an "assay plate". The invention usually employs a "first assay plate" which is formed from a material (e.g. polystyrene) which optimizes adherence of cells (having the receptor or receptor construct) thereto. Generally, the individual wells of the first assay plate will have a high surface area to volume ratio and therefore a suitable shape is a flat bottom well (where the cells are adherent). The "second assay plate" is generally formed from a material (e.g. polystyrene) which optimizes adherence of the capture agent thereto. The second assay plate may have the same general construction and/or characteristics as the first assay plate. However, separate plates are used for the KIRA stage of the assay and the ELISA stage of the assay.

In the preferred embodiment of the invention, both the first assay plate and the second assay plate are "microtiter" plates. The term "microtiter" plate when used herein refers to an assay plate having between about 30 to 200 individual wells, usually 96 wells. Often, the individual wells of the microtiter plate will hold a maximum volume of about 250 $\mu$l. Conveniently, the first assay plate is a 96 well polystyrene or plastic, cell culture microtiter plate (such as that sold by Becton Dickinson Labware, Lincoln Park, N.J.), which allows for automation. Often, about 50 $\mu$l to 300 $\mu$l, more preferably 100 $\mu$l to 200 $\mu$l, of an aqueous sample comprising cell culture media with the cells suspended therein will be added to each well of the first assay plate in the KIRA stage of the assay. It is desirable to seed between about $1\times10^4$ to $3\times10^5$ cells per well. More preferably, $5\times10^4$ to $1\times10^5$ cells per well are seeded. Usually, the second assay plate will comprise a polystyrene microtiter ELISA plate such as that sold by Nunc Maxisorp, Inter Med, Denmark.

The term "homogeneous population of cells" refers to a substantially homogeneous population of cells wherein at least about 8%, and preferably about 90%, of the cells in the population are of the same cell type. Therefore, it is convenient to use a cell line. The cell line is a eukaryotic cell line, normally an animal cell line and desirably a mammalian cell line.

The cells have, or are transformed to produce, the selected receptor or a receptor construct. For example, where the kinase receptor is known to be present in a certain cell line (e.g., the HER2 receptor in the MCF-7 cell line) no transformation step is required. Conversely, it may be necessary to transform a cell with a nucleic acid encoding the receptor, where the cell does not make the receptor, or does not have suitable numbers of the receptor in the cell membrane thereof. Accordingly, the cell is transformed with a nucleic acid encoding the receptor (or receptor construct) and the nucleic acid is expressed so that the ECD of the receptor faces the external milieu of the cell, the transmembrane domain is located in the cell membrane and the kinase domain is located intracellularly.

Where the assay relies on activating the endogenous rPTK, a cell line is selected which is known to produce the rPTK of interest, provided sufficient levels of the rPTK are present in the cell membrane thereof to enable detection. As a general proposition, a minimum number of about $1\times10^4$ receptors/cell is required. For example, the MCF-7 cell line (ATCC-HTB 22) which produces the HER2 receptor was shown to be useful in the assay. There are $5\times10^4$ HER2 receptors/MCF-7 cell. Examples of other cell lines and their respective rPTKs include, embryonic mouse 3T3-C2 fibroblast cell line and the insulin receptor, and Hep 3B (ATCC # HB 8064) cell line and the Rse receptor. However, the degree of expression of the rPTK nucleic acid in the cell line is not so high that it results in constitutive phosphorylation of the rPTK. For example, the SK-BR-3 cell line (ATCC HTB30), which has $3\times10^6$ HER2 receptors/cell, was found to be unsuitable for use in the assay disclosed herein. Therefore, it may be useful to use a cell line which has less than about $3\times10^6$ receptors/cell, depending on the type of receptor. The number of receptors/cell can be measured using Scatchard analysis, for example (Scatchard, Ann. NY Acad. Sci. 51:660–672 [1949]; and Goodwin et al., Cell 73:447–456 [1993]). However, selection of a cell line having a suitable number of receptors/cell is possible using the techniques described herein.

The term "adherent" when used herein to describe the cell, refers to a cell which naturally adheres to the first solid phase (often the well of the first assay plate), thereby forming a fairly uniform coating of the cells on the inside surface of the well. The uniform coating of cells generally forms following incubation of the cells in the wells of the first assay plate for about 8–16 hours. After incubation, non-adhering cells and cell culture medium are decanted off the first assay plate. Incubation is usually carried out at a temperature which is optimal for cell growth, i.e, about 37° C. Examples of adherent cell lines include CHO cells (Urlaub and Chasin, *Proc. Natl. Acad. Sci. USA* 77:4216 [1980]), MCF-7 cells (ATCC HB 22), 293 cells (Graham et al., *J. Gen Virol.* 36:59 [1977]), Swiss albino 3T3 fibroblast cell line (ATCC No. CCL 92) and U937 macrophage cell line (ATCC No. CRL 1593).

A "flag polypeptide" comprises a short polypeptide which has enough residues to provide an epitope (preferably a linear epitope) against which a "capture agent" thereagainst can be made, yet is short enough such that it does not interfere with activity of the rPTK. The flag polypeptide is also sufficiently unique so that the capture agent thereagainst does not bind to other reagents in the assay. Selection of a "unique" flag polypeptide sequence can be accomplished by comparing the sequence of a proposed flag polypeptide against other known sequences in Genbank or EMBL, for example. Suitable flag polypeptides generally have at least 6 amino acid residues and usually between about 8–80 amino acid residues (preferably between about 9–30 amino acid residues).

By "receptor construct" is meant a polypeptide which comprises a fusion of a kinase receptor and a flag polypeptide as defined above. The flag polypeptide is provided at a location in the receptor construct such that: a) the flag polypeptide does not interfere with ligand binding to the receptor; b) the flag polypeptide does not interfere with autophosphorylation of the receptor and c) the flag polypeptide is presented in a suitable configuration so that it can bind to the capture agent in the ELISA stage of the assay. Often, the polypeptide flag will be present at the N-terminus of the receptor construct. See, for example, Example 3 which refers to the gD.trk constructs. Alternatively, the flag polypeptide may be present at the C-terminus of the receptor construct. See, for example, Example 2 which refers to the Rse.gD construct. See also FIGS. 1A–1C. The Rse construct disclosed herein is particularly useful, since the ICD (and optionally the transmembrane domain) thereof can be fused to the ECD of a kinase receptor of interest, thereby obviating the need to establish where the flag polypeptide should be located with respect to the kinase receptor of interest.

"Rse.gD" refers to a receptor construct which is the Rae receptor protein tyrosine kinase with the Herpes Simplex virus glycoprotein D (gD) flag polypeptide fused to the COOH-terminus thereof.

"Rse.flag reagent" refers to a polypeptide which comprises the ICD of the Rse receptor fused at its COOH-terminus to a flag polypeptide (normally the gD flag polypeptide). Sometimes, the TM domain of Rae and the ECD of a rPTK of interest will also be present in the Rse.gD. reagent. "Receptor ECD/Rse.gD Chimera" refers to a fusion of the ECD of a rPTK of interest to the TM and ICD domains of Rse which are fused COOH-terminally to the gD flag polypeptide.

"gD.trkA", "gD.trkB" and "gD.trkC" refer to each of the trk receptors (A–C) having the gD flag polypeptide fused to the amino-termini thereof.

By "capture agent" is meant a compound or agent which is able to adhere to the second solid phase, as herein defined, and which is selective for a rPTK or receptor construct. Thus, the capture agent captures the receptor or receptor construct to the wells of the second assay plate. Usually, the capture agent binds selectively to the flag polypeptide which has been fused to the receptor of interest. Binding of the capture agent is not affected by the presence or absence of ligand bound to the receptor and does not induce receptor activation upon capture. Furthermore, the capture agent does not sterically block access to the phosphorylated tyrosine(s) by the anti-phosphotyrosine antibody. Means for selecting suitable capture agents are described herein. Generally, the capture agent will comprise an antibody (e.g., an affinity purified polyclonal antibody or a monoclonal antibody), but other selective agents, such as streptavidin which binds selectively to the "strep-tag" polypeptide can also be used (see Schmidt et al., *Protein Engineering* 6(1):109–122 [1993]). Streptavidin can be purchased commercially from Zymed Laboratories, S. San Francisco, Calif., for example. Alternatively, the capture agent can comprise protein A (which binds specifically to immunoglobulins). In this embodiment of the invention, the activated receptor or receptor-construct present in the cell lysate is incubated with an antibody which binds specifically thereto, thereby forming a receptor-antibody complex. This complex can be captured by protein A by virtue of its specific binding to the antibody present in the complex. Protein A can be purchased commercially from Pharmacia Biotech, Inc., Piscataway, N.J., for example. A strategy for selecting a suitable capture agent is depicted in FIG. 3 and will be described in more detail later herein.

In the most preferred embodiment, the capture agent is a monoclonal antibody which binds specifically to a flag polypeptide (which is present in the receptor construct). Examples of suitable flag polypeptides and their respective capture antibodies include the flu HA flag and its antibody 12CA5, (Field et al., *Mol. Cell. Biol.* 8:2159–2165 [1988]); the c-myc flag and the 8F9, 3C7, 6E10, G4, B7 and 9E10 antibodies thereto (Evan et al., *Molecular and Cellular Biology* 5(12):3610–3616 [1985]); as well as the Herpes Simplex virus glycoprotein D (gD) flag and the 5B6 antibody thereto (Paborsky et al., *Protein Engineering* 3(6) :547–553 [1990] and Mark et al., *Journal of Biological Chemistry* 269(14):10720–10728 [1994]). other flag polypeptides have been disclosed. Examples include the Flag-peptide (Hopp et al., *BioTechnology* 6:1204–1210 [1988]); the KT3 epitope peptide (Martin et al., *Science* 255:192–194 [1992]); an α-tubulin epitope peptide (Skinner et al., *J. Biol. Chem* 266:15163–15166 [1991]); and the T7 gene 10 protein peptide tag (Lutz-Freyermuth et al., *Proc Natl. Acad. scia USA* 87:6393–6397 [1990]). Once the flag polypeptide has been selected as discussed above, a capture antibody thereto can be generated using the techniques disclosed herein.

The term "analyte" refers to a compound or composition to be studied, usually to investigate its ability to activate (or prevent activation of) the tyrosine kinase receptor of interest. The analyte can comprise a bodily fluid (such as plasma or amniotic fluid) or a composition known to contain, or suspected of containing, a ligand for the tyrosine kinase receptor. The analyte can also comprise a cell which has a ligand to the rPTK of interest.

"Ligand" when used herein refers to a molecule which is able to bind to the ECD of the tyrosine kinase of interest or to a known agonist for the tyrosine kinase of interest. The ligand will usually be an agonist or antagonist for the tyrosine kinase.

By "agonist" is meant a molecule which is able activate the intracellular kinase domain of the tyrosine kinase upon binding to the ECD. Often, the agonist will comprise a growth factor (i.e., a polypeptide that is able to stimulate cell division). Exemplary growth factors include heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), fibroblast growth factor (FGF), transforming growth factors alpha and beta (TGF-α and TGF-β), hepatocyte growth factor (HGF), and nerve growth factor (NGF). Alternatively, the agonist can be an antibody against the rPTK (see, e.g., Yarden, *Proc, Natl. Acad, Sci. USA* 87:2569–2573 [19901]). However, other non-protein agonists such as small organic molecules are also encompassed by the invention.

By "antagonist" is meant a molecule which blocks agonist action. Usually. the antagonist will either: (a) bind to the rPTK and thereby block binding and/or activation of the rPTK by an agonist thereto (the antagonist may bind to the ECD of the rPTK, but this is not necessarily the case) or (b) bind to the agonist and thus prevent activation of the rPTK by the agonist. This assay facilitates the detection of both types of antagonist. The antagonist may, for example, comprise a peptide fragment comprising the receptor binding domain of the endogenous agonist ligand for the receptor. The antagonist may also be an antibody which is directed against the ECD of the rPTK, or against a known agonist for the rPTK. However, other non-protein molecules are also encompassed by this term.

The term "antibody" is used in the broadest sense and specifically covers monoclonal antibodies and antibody compositions with polyepitopic specificity (i.e. polyclonal antibodies). The polyclonal antibodies are preferably "affinity purified" antibodies. The term "affinity purified" means that the antibodies have been purified using the antigen (e.g. the rPTK or fragment thereof or the flag polypeptide) to selectively purify the polyclonal antibodies. Affinity purification can be achieved by immobilizing the antigen on an affinity column (e.g. an agarose column) and passing the polyclonal antibodies through the column. The affinity purified antibodies can be subsequently eluted from the column by changing the elution conditions or by adding a chaotropic agent, for example. For a review of affinity purification techniques with respect to antibodies, see *Current Protocols in Immunology*, Ed. Coligen et al., Wiley publishers, Vols. 1 and 2, for example.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of a selected antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. [See, e.g. U.S. Pat. No. 4,816,567 and Mage & Lamoyi, in *Monoclonal Antibody Production Techniques and Apolications*, pp.79–97 (Marcel Dekker, Inc., New York (1987]).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler & Milstein, *Nature*, 256: 495 (1975), or may be made by recombinant DNA methods (U.S. Pat. No. 4,816,567). The "monoclonal antibodies" may can also be isolated from phage antibody libraries using the techniques described in Clackson et al., *Nature*, 352: 624–628 (1991) and Marks et al., *J. Mol. giol.*, 222: 581–597 (1991), for example.

The term "anti-phosphotyrosine antibody" refers to a molecule, usually an antibody, which binds selectively to phosphorylated tyrosine residues in the kinase domain of a rPTK. The antibody can be polyclonal, but is desirably a monoclonal antibody. Anti-phosphotyrosine polyclonal antibodies can be made using the techniques disclosed in White and Backer, *Methods in Enzymology* 201:65–67 [199] and monoclonal anti-phosphotyrosine antibodies can be obtained commercially from Upstate Biologicals, Inc. (UBI, Lake Placid, N.Y.), for example.

The word "label" when used herein refers to a detectable compound or composition which is conjugated directly or indirectly with a molecule (such as the anti-phosphotyrosine antibody). The label may be detectable by itself (e.g. radioisotope labels or fluorescent labels) or, in the case of an enzymatic label, may catalyze a chemical alteration of a substrate compound or composition which is detectable. The preferred label is an enzymatic one which catalyzes a color change of a non-radioactive color reagent.

By "washing" is meant exposing the solid phase to an aqueous solution (usually a buffer or cell culture media) in such a way that unbound material (e.g., non-adhering cells, non-adhering capture agent, unbound ligand, receptor, receptor construct, cell lysate, or anti-phosphotyrosine antibody) is removed therefrom. To reduce background noise, it is convenient to include a detergent (e.g. Triton X) in the washing solution. Usually, the aqueous washing solution is decanted from the wells of the assay plate following washing. Conveniently, washing can be achieved using an automated washing device. Sometimes, several washing steps (e.g., between about 1 to 10 washing steps) may be required.

By "block buffer" is meant an aqueous, pH buffered solution containing at least one blocking compound which is able to bind to exposed surfaces of the second solid phase which are not coated with capture agent. The blocking compound is normally a protein such as bovine serum albumin (BSA), gelatin, casein or milk powder and does not cross-react with any of the reagents in the assay (e.g., the anti-phosphotyrosine antibodies and detection reagents). The block buffer is generally provided at a pH between about 7 to 7.5 and suitable buffering agents include phosphate and TRIS.

By "lysis buffer" is meant an aqueous, pH buffered solution comprising a solubilizing detergent, one or more protease inhibitors and at least one phosphatase inhibitor (such as sodium orthovanadate). The term "solubilizing detergent" refers to a water miscible, non-ionic detergent which lyses cell membranes of eukaryotic cells but does not denature or activate the receptor or receptor construct. Examples of suitable non-ionic detergents include Triton-X 100, Tween 20, CHAPS and Nonidet P-40 (NP40) available from Calbiochem, La Jolla, Calif., for example. Many other non-ionic detergents are available in the art. Examples of suitable protease inhibitors include phenylmethylsulfonyl fluoride (PMSF), leupeptin, pepstatin, aprotinin, 4-(2-aminoethyl)-benzenesulfonyl fluoride hydrochloride-bestatin, chymostatin and benzamidine. Preservatives (e.g., thimerosal) and one or more compounds which maintain the isotonicity of the solution (e.g., sodium chloride [NaCl] or sucrose) and a buffer (e.g., Tris or PBS) are usually also present. Generally, the pH of the lysis buffer is in the range about 7 to 7.5.

Usually, following addition of the lysis buffer to the first assay plate, the first assay plate is "gently agitated" and this expression refers to the act of physically shaking the first assay plate (normally using a circular motion) at a substantially low velocity. Gentle agitation does not involve mechanically disrupting the cells (e.g. by homogenizing or centrifuging the cells). Exemplary shaking velocities are in the order of 200 to 500 rpm, preferably 300 to 400 rpm in a Bellco orbital shaker, for example.

II. Modes for Practicing the Invention

1. Kinase Receptor Activation—KIRA

The first stage of the assay involves phosphorylation of the kinase domain of a kinase receptor, wherein the receptor is present in the cell membrane of a eukaryotic cell. The receptor may be an endogenous receptor or nucleic acid encoding the receptor may be transformed into the cell. In one embodiment of the invention, nucleic acid encoding a receptor construct is transformed into the cell. Exemplary techniques for transforming the cell with either the receptor or the receptor construct nucleic acid follow.

A. Transformation of the Cells

The instant invention provides a substantial improvement over soluble kinase receptor assays insofar as it is considered to more accurately reflect the activity of the receptor in situ. It has been discovered that it is possible to transform eukaryotic cells with a receptor construct (comprising the kinase receptor and either an amino- or carboxyl-terminal flag polypeptide) so that the receptor construct assembles itself appropriately in the cell membrane and still retains tyrosine kinase activity which can be detected in the ELISA stage of the assay. This provides a generic assay for measuring tyrosine kinase activity of any tyrosine kinase of interest.

If a suitable capture agent as described herein is available for a selected rPTK, cells can be transformed with the nucleic acid encoding the receptor alone, without the flag polypeptide. Alternatively, if cells are available which produce the receptor (e.g., MCF-7 cells which produce the HER2 receptor), it is not necessary to transform the cells for use in the assay.

In order to transform the cells with the nucleic acid encoding the rPTK or receptor construct, nucleic acid encoding the rPTK and, optionally, the flag polypeptide, is isolated. This can be achieved by screening a cDNA or genomic library known to contain the DNA encoding the rPTK or flag polypeptide of interest with a selected labelled probe (e.g., an antibody or oligonucleotide- probe) for the rPTK or flag polypeptide, using standard procedures as described in chapters 10–12 of Sambrook et al., *Molecular Cloning: A Laboratory Manual* (New York: Cold Spring Harbor Laboratory Press, 1989), for example. Alternatively, the nucleic acid encoding the flag polypeptide can be made synthetically using an oligo-synthesizing machine (Applied Biosystems, CA). An alternative means to isolate the nucleic acid encoding the rPTK or flag polypeptide is to use PCR methodology as described in section 14 of Sambrook et al., supra. Isolation of only the ECD of the rPTK of interest is required, since this nucleic acid can be fused to the nucleic acid encoding the TM and ICD of the Rse-flag polypeptide construct disclosed herein. See FIGS. 1A–1C and SEQ ID NOS: 1 and 2. If necessary however, conventional primer extension procedures as described in section 7.79 of Sambrook et al., supra, can be used to detect precursors and processing intermediates of mRNA that may not have been reverse-transcribed into cDNA.

A preferred method of practicing this invention is to use carefully selected oligonucleotide sequences to screen cDNA libraries from various tissues, preferably mammalian cell lines having the rPTM of interest. The oligonucleotide sequences selected as probes should be of sufficient length and sufficiently unambiguous that false positives are minimized.

The oligonucleotide must be labeled such that it can be detected upon hybridization to DNA in the library being screened. The preferred method of labeling is to use $^{32}$P-labeled ATP with polynucleotide kinase, as is well known in the art, to radiolabel the oligonucleotide. However, other methods may be used to label the oligonucleotide, including, but not limited to, biotinylation or enzyme labeling.

In order to provide nucleic acid encoding a receptor construct, nucleic acid encoding the rPTK is fused at its 3' end to nucleic acid encoding the N-terminus of the flag polypeptide. Alternatively, the nucleic acid encoding the rPTM will be fused at its 5' end to nucleic acid encoding the carboxyl terminus of the flag polypeptide. Thus, the flag polypeptide is provided at either the carboxyl- or amino-terminus of the receptor construct. Examples of suitable flag polypeptides are provided above. Selection of other suitable flag polypeptides is possible using the techniques described herein.

In order to generate fusions between the Rse.flag reagent and a rPTK of interest, the nucleic acid encoding the ECD of the rPTK of interest is fused at its 3' end to the nucleic acid encoding the amino terminus of the Rse.flag reagent.

The nucleic acid (e.g., cDNA or genomic DNA) encoding the rPTK or receptor construct is then inserted into a replicable vector for further cloning (amplification of the DNA) or for expression. Many vectors are available to the skilled practitioner but must be compatible with the cell which is to be used in the assay. The vector will have vector components the presence of which will depend on various factors. Such components include, for example, a signal sequence, an origin of replication, one or more marker genes, an enhancer element, a promoter, and a transcription termination sequence. Selection of these vector components shall be described below.

Incorporation of a signal sequence into the expression vector is required since the rPTK or receptor construct must be transported to the cell membrane where it is positioned such that the ECD faces the external milieu of the cell. Therefore, a signal sequence suitable for positioning the rPTK or receptor construct in such a manner is used. The signal sequence is generally a component of the vector, or it may be a part of the rPTK or receptor construct DNA that is inserted into the vector. If a heterologous signal sequence is used, it is from those that are recognized and processed (i.e., cleaved by a signal peptidase) by the host cell.

For yeast secretion the native signal sequence may be substituted by, e.g., the yeast invertase leader, alpha factor leader (including saccharomyces and Kluyveromyces α-factor leaders, the latter described in U.S. Pat. No. 5,010,182 issued Apr. 23, 1991), or acid phosphatase leader, the C. albicans glucoamylase leader (EP 362,179 published Apr. 4, 1990), or the signal described in WO 90/13646 published Nov. 15, 1990. In mammalian cells expression of the DNA encoding the native signal sequence (e.g., the rPTK presequence that normally directs secretion of rPTK from mammalian cells in vivo) is satisfactory, although other mammalian signal sequences may be suitable, such as signal sequences from other animal rPTKs, and signal sequences from secreted polypeptides of the same or related species, as well as viral secretory leaders, for example, the herpes simplex gD signal.

The DNA for such precursor region is ligated in reading frame to DNA encoding the rPTK or receptor construct.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. The $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transformed into another organism for expression. For example, a vector is cloned in *E. coli* and then the same vector is transformed into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transformation of Bacillus with this vector results in homologous recombination with the genome and insertion of rPTK or receptor construct DNA. However, the recovery of genomic DNA encoding the rPTK or receptor construct is more complex than that of an exogenously replicated vector because restriction enzyme digestion is required to excise the rPTK or receptor construct DNA.

Expression and cloning vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

One example of a selection scheme utilizes a drug to arrest growth of a host cell. Those cells that are successfully transformed with a heterologous gene express the DNA encoding a protein conferring drug resistance and thus survive the selection regimen. Examples of such dominant selection use the drugs neomycin (Southern et al., *J. Molec, Appl. Gnet.* 1:327 [1982]), mycophenolic acid (Mulligan et al., *Science* 209:1422 [1980]) or hygromycin (Sugden et al., *Mol. Cell. Biol,* 5:410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the rPTK or receptor construct nucleic acid, such as DHFR or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the rPTK or receptor construct. Amplification is the process by which genes in greater demand for the production of a protein critical for growth are reiterated in tandem within the chromosomes of successive generations of recombinant cells. Increased quantities of rPTK or receptor construct are synthesized from the amplified DNA. Other examples of amplifiable genes include metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad Sci. USA* 77:4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the rPTK or receptor construct. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060).

Alternatively, host cells (particularly wild-type hosts that contain endogenous DHFR) transformed or co-transformed with DNA sequences encoding the rPTK or receptor construct, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the tzpl gene present in the yeast plasmid YRp7 (Stinchcomb et al., *Nature* 282:39 [1979]; Kingsman et al., *Gene* 7:141 [19791]; or Tschemper et al., *Gene* 10:157 [1980]). The trp1 gene provides a selection marker for a mutant strain of yeast lacking the ability to grow in tryptophan, for example, ATCC No. 44076 or PEP4-1 (Jones, *Genetics* 85:12 [1977]). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 $\mu$m circular plasmid pKD1 can be used for transformation of Kluyveromyces yeasts. Bianchi et al., *Curr. Genet.* 12:185 (1987). More recently, an expression system for large-scale production of recombinant calf chymosin was reported for K. lactis. Van den Berg, *Bio/Technology* 8:135 (1990). Stable multi-copy expression vectors for secretion of mature recombinant human serum albumin by industrial strains of Kluyveroiices have also been disclosed. Fleer et al., *Bio/Technology* 9:968–975 (1991).

Expression and cloning vectors usually contain a promoter that is recognized by the host organism and is operably linked to the rPTK or receptor construct nucleic acid. Promoters are untranslated sequences located upstream (5') to the start codon of a structural gene (generally within about 100 to 1000 bp) that control the transcription and translation of particular nucleic acid sequence, such as the rPTK nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to rPTK or receptor construct-encoding DNA by removing the promoter from the source DNA by restriction enzyme digestion and inserting the isolated promoter sequence into the vector. Both the native rPTK promoter sequence and many heterologous promoters may be used to direct amplification and/or expression of the rPTK or receptor construct DNA. The promoter will be one which results in the accumulation of suitable numbers of receptor or receptor construct in the cell membrane of the transformed cell (i.e. so that autophosphorylation of the receptor is detectable in the ELISA but constitutive phosphorylation does not occur). Selection of a suitable promoter to achieve this is possible following the guidelines herein for selecting cells for use in the KIRA ELISA.

Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.* 255:2073 [1980]) or other glycolytic enzymes (Hess et al., *J. Adv. Enzyme Rea.,* 7:149 [1968]; and Holland, *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

rPTK or receptor construct transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter or an immunoglobulin promoter, from heat-shock promoters, and from the promoter normally associated with the rPTK or receptor construct sequence, provided such promoters are compatible with the host cell systems.

The early and late promoters of the SV40 virus are conveniently obtained as an SV40 restriction fragment that also contains the SV40 viral origin of replication. Fiers et al., *Nature* 273:113 (1978); Mulligan and Berg, *Science* 209:1422–1427 (1980); Paylakis et al., *Proc. Natl. Acad. Sci. USA* 78:7398–7402 (1981). The immediate early promoter of the human cytomegalovirus is conveniently obtained as a HindIII E restriction fragment. Greenaway et al., *Gene* 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature* 295:503–508 (1982) on expressing cDNA encoding immune interferon in monkey cells; Reyes et al., *Nature* 297:598–601 (1982) on expression of human β-interferon cDNA in mouse cells under the control of a thymidine kinase promoter from herpes simplex virus; Canaani and Berg, *Proc. Natl. Acad. Sci. USA* 79:5166–5170 (1982) on expression of the human interferon β1 gene in cultured mouse and rabbit cells; and Gorman et al., *Proc. Natl. Acad. Sci. USA* 79:6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

Transcription of DNA encoding the rPTK or receptor construct by higher eukaryotes may be increased, if increased numbers of the rPTK or receptor construct per cell are required to facilitate detection in the ELISA stage of the assay. This may be achieved by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al., *Proc, Natl. Acad, Sci. USA* 78:993 [1981]) and 3' (Lusky et al., *Mol Cell Bio,* 3:1108 [19833]) to the transcription unit, within an intron (Banerji et al., *Cell* 33:729 [1983]), as well as within the coding sequence itself (Osborne et al., *Mol. Cell Bio,* 4:1293 [1981]). Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297:17–18 (1982) on enhancing elements for activation of eukaryotic promoters. The enhancer may be spliced into the vector at a position 5' or 3' to the rPTK or receptor construct-encoding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the rPTK or receptor construct.

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res*, 9:309 (1981) or by the method of Maxam et al., *Methods in Enzymology* 65:499 (1980).

Other methods, vectors, and host cells suitable for adaptation to the synthesis of the rPTK or receptor construct in recombinant vertebrate cell culture are described in Gething et al., *Nature* 293:620–625 (1981); Mantei et al., *Nature* 281:40–46 (1979); Levinson et al.; EP 117,060; and EP 117,056. A particularly useful plasmid for mammalian cell culture expression of rPTK or receptor construct DNA is pRKS (EP 307,247) or pSVI6B (PCT pub. no. WO 91/08291 published Jun. 13, 1991).

Examples of suitable eukaryotic cell lines for transformation include *saccharomyces cerevisiae, Schizosaccharomyces pombe* (Beach and Nurse, *Nature* 290:140 [1981]; EP 139,383 published May 2, 1985); Kluyveromyces hosts (U.S. Pat. No. 4,943,529; Fleer et al., *Bio/Technology* 9:968–975 [1991]) and Aspergillus hosts such as *A. nidulans* (Ballance et al., *Biochem. Biophys. Res, Commun.* 112:284–289 [1983]; Tilburn et al., *Gene* 26:205–221 [1983]; Yelton et al., *Proc. Natl. Acad. Sci. USA* 81:1470–1474 [1984]) and A. niger (Kelly and Hynes, *EMBO J*. 4:475–479 [1985]), among lower eukaryotic host microorganisms.

Examples of useful animal host cell lines for transformation include monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 [1977]); baby hamster kidney cells (BHK, ATCC CCL 10); Chinese hamster ovary cells/-DHFR (CHO, Urlaub and Chasin, *Proc. Natl. Acad. Sci. USA* 77:4216 [1980]); mouse sertoli cells (TM4, Mather, *Biol. Reprod.* 23:243–251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Rep G2, HB 8065); mouse mammary tumor (MMT 060562, ATCC CCL51); TRI cells (Mather et al., *Annals N.Y. Acad. Sci.* 383:44–68 [1982]); MRC 5 cells; FS4 cells; and a human hepatoma line (Hep G2).

Host cells are transformed with the above-described expression or cloning vectors of this invention and cultured in conventional nutrient media modified as appropriate for inducing promoters, selecting transformants, or amplifying the genes encoding the desired sequences. Transformation means introducing DNA into an organism so that the DNA is replicable, either as an extrachromosomal element or as a chromosomal integrant. Depending on the host cell used, transformation is done using standard techniques appropriate to such cells. Successful transformation is generally recognized when any indication of the operation of this vector occurs within the host cell.

For mammalian cells, the calcium phosphate precipitation method of Graham and Van der Eb, *Virology* 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.* 130:946 (1977) and Hsiao et al., *Proc. Natl. Acad. Sci. (USA)* 76:3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1989), Keown et al., *Methods in Enzymology* 185:527–537 (1990), and Mansour et al., *Nature* 336:348–352 (1988).

The mammalian host cells used to produce the rPTK or receptor construct may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth, Enz.* 58:44 (1979), Barnes and Sato, *Anal, Biochem* 102:255 (1980), U.S. Pat. Nos. 4,767,704; 4,657,866; 4,927, 762; or 25 4,560,655; WO 90/03430; WO 87/00195; U.S. Pat. Re. No. 30,985; or U.S. Pat. No. 5,122,469, the disclosures of each of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as REPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: a Practical Approach*, M. Butler, ed., IRL Press, 1991.

Gene amplification and/or expression may be measured in a sample directly, for example, by conventional Southern blotting, Northern blotting to quantitate the transcription of mRNA (Thomas, *Proc. Natl. Acad. Sci. USA* 77:5201–5205 [1980]), dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorophores, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining to quantitate directly the expression of gene product.

B. Selecting Cells for Use in the Assay

As mentioned above, the cells to be subjected to the assay can be (a) cells having an endogenous receptor, (b) cells which have been transformed with a rPTK, or (c) cells transformed with a receptor construct. The suitability of the cells for use in the assay is investigated.

Cells having the endogenous rPTK can be subjected to a test-run KIRA ELISA using a known ligand to the PTK (e.g. an agonist antibody) and a control (e.g. the diluent for the agonist antibody). A range of ligand concentrations such as those used herein (see Examples 1, 2 and 3) will be used to determine whether sufficient numbers of the receptor are present in the cells being tested. In order to discover whether a cell line is unsuitable because the receptor is constitutively phosphorylated, the cell line can be subjected to the KIRA ELISA disclosed herein, wherein it is exposed to both positive and negative controls (e.g. a known agonist ligand in cell culture media as described herein as a positive control and the cell culture media without the agonist ligand as the negative control). If phosphorylation of the receptor is detected for both positive and negative controls, this may be indicative that constitutive phosphorylation of the receptor is occurring. However, it is possible that a constituent of the serum in the cell culture media is activating the receptor. Thus, the cells can be "starved" in serum-free media for about 2–12 hours (depending on cell survival) and then the assay is repeated using the positive and negative controls. If activation is detected for both controls, the cell line may be considered unsuitable and another cell line can be tested.

If the cell line is transformed with the receptor (without the flag polypeptide) a strategy similar to that depicted in FIG. 4 can be used to discover whether or not the cell line is suitable for use in the assay. As a first step, successful transformation and expression of the nucleic acid encoding the rPTK is determined (see FIG. 4, step b). In order to identify whether the ECD of the rPTK is present on the surface of the cells, flow cytometric analysis can be performed using an antibody to the ECD of the receptor. The antibody can be made using the techniques for generating antibodies discussed herein. Flow cytometric analysis can be carried out using the techniques described in *Current Protocols in Immunology*, Ed. Coligen et al., Wiley publishers, Vols. 1 and 2, for example. Briefly, flow cytometric analysis involves incubating intact cells (having the receptor) with antibodies to the ECD thereof, followed by washing. The antibody-bound cells are then incubated with species specific anti-antibody antibodies conjugated to a fluorochrome. Following washing, the labeled cells are analyzed by fluorescence-activated flow cytometry to detect whether the ECD is present on the surface of the cells.

In the following step, i.e. FIG. 4, step (c), the ability of the cell-bound receptor to be activated is tested. In order to determine this, the transformed cells are exposed to a known agonist to the receptor (e.g. the endogenous ligand or an agonist antibody for the receptor). Following exposure, the cells are lysed in a suitable buffer (e.g. sodium dodecylbenzenesulfonate in phosphate buffered saline; SDS in PBS) and subjected to Western blotting with anti-phosphotyrosine antibodies as described in Wang, *Molecular and Cellular Biology* 5(12):3640–3643 (1985); Glenney et al., *Journal of Immunological Methods* 109:277–285 (1988); Kamps, *Methods in Enzymology* 201:101–110 (1991); Kozma et al., *Methods in Enzymology* 201:28–43 (1991); Holmes et al., *Science* 256:1205–10 (1992); or Corfas et al., *PNAS. USA* 90:1624–1628 (1993), for example.

Assuming the Western blotting step indicates that the rPTK can be activated, a KIRA ELISA test run can be performed, see FIG. 4 step (d), to further establish whether or not the transformed cell line can be used in the assay.

In the preferred embodiment of the invention, the KIRA ELISA is a "generic" assay insofar as any rPTK of interest can be studied regardless of the availability of receptor-specific reagents (i.e., capture agent). This embodiment employs a receptor construct having a flag polypeptide at either the amino or carboxyl terminus of the receptor.

If the flag polypeptide is provided at the $NH_2$-terminus (see, e.g., the gD.trk A, B and C receptor constructs disclosed in Example 3), the procedure for selecting a transformed cell line for use in the assay summarized in FIG. 4 can be performed. In this embodiment, the cells are transformed with the flag polypeptide-receptor construct as described earlier herein. See step (a). In step (b), successful transformation of the receptor and flag polypeptide (i.e. the receptor construct) is confirmed. In order to study this, two-dimensional flow cytometric analysis can be performed using antibodies to both the flag polypeptide and the ECD of the receptor. Techniques for two-dimensional flow cytometric analysis are disclosed in *Current Protocols in Immunology*, supra. Assuming successful transformation of the receptor construct is demonstrated, steps (c) and (d) of FIG. 4 are then performed. See the discussion above, for an explanation of steps (c) to (d) of FIG. 4.

A technique for identification of cells which have been successfully transformed with the receptor construct having a C-terminal flag polypeptide and which cells are also suitable for use in the assay is illustrated in FIG. 5. Following cell transformation [step (a)], successful transformation of the receptor is determined by flow cytometric analysis using an antibody directed against the ECD of the receptor of interest, for example. Flow cytometric analysis can be performed substantially as described above. This forms step (b) of the procedure outlined in FIG. 5.

Following step (b), successful transformation of the entire receptor construct (including the COOH-terminal flag polypeptide) is analyzed in step (c). This can be achieved by lysing the cells (using techniques for lysing cells disclosed herein) and immunoprecipitating the membrane extract with an antibody against the receptor of interest. This immoprecipitated membrane extract is then subjected to Western blot analysis with antibodies specific for the flag polypeptide. Alternatively, rPTK-specific ELISA analysis of anti-flag polypeptide captured membrane lysate can be carried out. Briefly, this involves coating ELISA wells with appropriate flag specific capture agent. The wells are blocked, washed, and the lysate is then incubated in the wells. Unbound receptor construct is removed by washing. The wells are then reacted with receptor-specific antibody or antibodies, either directly or indirectly conjugated to HRPO. The wells are washed and the HRPO is then exposed to the chromogenic substrate (e.g., TMB).

Steps (d) and (e), i.e., detecting receptor activation and KIRA ELISA test run, are essentially the same as those steps described above.

Once useful cells are identified, they are subjected to the KIRA stage of the instantly claimed assay.

C. Coating the First Solid Phase with the Cells

The first solid phase (e.g. a well of a first assay plate) is coated with cells having the endogenous receptor or cells which have been transformed pursuant to the preceding sections.

Preferably, an adherent cell line is chosen, so that the cells naturally adhere to the first solid phase. However, use of an adherent cell line is not essential. For example, non-adherent cells (e.g. red blood cells) can be added to round bottomed wells of an assay plate such as that sold by Becton Dickinson Labware, Lincoln Park, New Jersey, for example. The assay plate is then placed in a plate carrier and centrifuged so as to create a pellet of cells adhering to the base of the wells. The cell culture supernatants are removed using a pipette. Thus, use of an adherent cell is clearly advantageous over non-adherent cells since it reduces variability in the assay (i.e, the cells in the pellet of the round bottom wells may be taken up with the supernatant when the alternative method is used).

The cells to be added to the wells of the first assay plate may be maintained in tissue culture flasks and utilized when cells densities of about 70–9of confluency are achieved. Then, generally between about $1\times10^4$ to $3\times10^5$ (and preferably $5\times10^4$ to $1\times10^5$) cells are seeded per flat-bottom well, using a pipette, for example. It has been found that, contrary to expectations; addition of cell concentrations mentioned above is sufficient to enable activation of the rPTK to be measured in the ELISA stage of the assay, without the need to concentrate or clarify the cells or cell lysate prior thereto. Often, the cells are diluted in culture medium prior to seeding them in the wells of the microtiter plate to achieve the desired cell densities.

Usually, the cells are cultured in the microtiter plates for a sufficient period of time to optimize adherence to the wells thereof, but not too long such that the cells begin to deteriorate. Thus, incubation for about 8 to 16 hours at a temperature which is the physiological optimum for the cells (usually about 37° C.) is preferred. Suitable media for culturing the cells are described in Section 1A above. Culturing in 5% $CO_2$ is recommended.

Following incubation overnight, the well supernatants are decanted and excess supernatant may be further removed by lightly tamping the microtiter plates with an absorbent substrate, e.g., a paper towel, but a sponge works equally well. Thus, a substantially homogeneous layer of adhering cells remains on the internal surfaces of the individual wells of the microtiter plate. These adhering cells are then exposed to the analyte.

D. Preparation and Addition of the Analyte

As mentioned above, the analyte may comprise an agonist ligand (or suspected agonist) or an antagonist (or suspected antagonist) for the rPTK of interest. The ligand may be an endogenous polypeptide, or a synthetic molecule, such as an inorganic or organic molecule. Usually, the ligand is a polypeptide. This assay is useful for screening molecules which activate (or antagonize activation) of the tyrosine kinase receptor of interest. Thus, the assay can be used for developing therapeutically effective molecules.

Where the ligand is an agonist, the molecule can comprise the native growth factor e.g., heregulin (HRG), insulin, insulin-like growth factors I and II (IGF-I and IGF-II), epidermal growth factor (EGF), interleukins (e.g., IL-8), macrophage colony-stimulating factor (M-CSF), erythropoietin (EPO), platelet-derived growth factor (PDGF), transforming growth factors alpha and beta (TGF-α and TGF-β), hepatocyte growth factor (RGF), fibroblast growth factor (FGF) and nerve growth factor (NGF). Many of these growth factors are available commercially. Alternatively, the growth factor can be made by peptide synthesis or recombinant techniques which are described herein. Synthetic small molecule agonists can similarly be generated by those skilled in the art using conventional chemical synthesis techniques.

Where the ligand is present in a biological fluid, the analyte can be prepared using techniques which are well known in the art. Body fluid such as blood or amniotic fluid may be used directly, however concentration may be required. If the analyte to be tested comprises a particular tissue, the cells thereof can be grown in cell culture and the supernatant can be tested for secreted ligand.

Often, the ligand is diluted in an aqueous diluent (such as cell culture media) so that a standard curve can be generated. However, the ligand may be present in a cell or a cell component (e.g., the cell membrane). In particular, it has been found that the assay can be used to detect the presence of a ligand in the cell membrane of a selected cell line. This is clearly useful for discovering a novel endogenous ligand for a known rPTK.

The ligand composition is added to each well which contains the adhering cells using a pipette, for example. At least one control well (e.g. to which the aqueous diluent for the ligand is added) is included in the assay.

The adhering cells are usually stimulated for a sufficient period of time to optimize the signal, but not too long such that the signal decreases as a consequence of dephosphorylation of the rPTK by endogenous phosphatases. A suitable stimulation period is between about 10 to 60 minutes, preferably about 30 minutes at a physiologically optimal temperature for the cells (usually about 37° C.).

Following activation, well supernatants are decanted and the plates can then be lightly tamped with an absorbent substrate to remove excess supernatant.

The assay can be used to detect antagonist ligands for the rPTK of interest. Antagonists generally fall into two categories (a) ones which bind to the rPTK and thereby block binding and/or activation of the rPTK by an agonist thereto (the antagonist may bind to the ECD, but this is not necessarily the case) and (b) those which bind to the agonist and thus prevent activation of the rPTK by the agonist.

In order to detect antagonist molecules from category (a) above, the cells are exposed to the suspected antagonist ligand substantially as mentioned above. Following exposure to the antagonist, the well supernatants are decanted and the plates are lightly tamped. Then, a known agonist (e.g., the endogenous growth factor) is added to the washed cells essentially as discussed in the preceding paragraphs, following which, the well supernatants are decanted and plates are lightly tamped. Alternatively, a composition comprising both the antagonist and agonist can be added to the adhering cells substantially as discussed above. Ability of the suspected antagonist to block binding and/or activation of the rPTK can subsequently be measured by ELISA as discussed below.

To detect antagonist molecules from category (b) above, a known agonist is pre-incubated with the suspected antagonist prior to the KIRA stage of the assay. This incubation is carried out for a sufficient period of time to enable a complex of the antagonist-agonist to form; from 30 min. to 12 hours, for example. This complex is then subjected to the assay with the non-complexed agonist and antagonist used as controls.

Following exposure to the agonist (and optionally the antagonist) ligand, the cells are lysed, as discussed below.

E. Solubilizing the Cells

In this step of the assay, the cells are lysed so as to solubilize the rPTK such that it remains activated (i.e., the tyrosine residues remain phosphorylated) for the ELISA stage of the assay. Thus, the cells are lysed using a lysis buffer as described above which serves to solubilize the rPTK or receptor construct, yet does not dephosphorylate or denature the rPTK.

Where microtiter plates are used as mentioned above, about 75 to 200 µl of lysis buffer is added to each well. The plates can then be agitated gently using a plate shaker (e.g., such as that sold by Bellco Instruments, Vineland, N.J.) for about 1 to 2 hours. Shaking can be carried out at room temperature.

2. Enzyme-Linked Immunosorbent Assay—ELISA

The second stage of the assay involves a sandwich ELISA performed in the second assay plate. In order to carry out the BLISA, a capture agent is prepared.

A. Preparation of the Capture Agent

As mentioned above, the capture agent often comprises a polyclonal antibody (usually an affinity purified polyclonal antibody) or monoclonal antibody. Other capture agents are envisaged and are discussed in the definitions section above. The capture agent either binds specifically to the kinase receptor, or to the flag polypeptide (i.e. the antigen).

Polyclonal antibodies to the antigen (either the receptor or the flag polypeptide) generally are raised in animals by multiple subcutaneous (ac) or intraperitoneal (ip) injections of the antigen or an antigenic fragment thereof (often the ECD of the rPTK) and an adjuvant. It may be useful to conjugate the antigen or a fragment containing the target amino acid sequence to a protein that is immunogenic in the species to be immunized (e.g., keyhole limpet hemocyanin), using a bifunctional or derivatizing agent.

The route and schedule for administration of immunogen to the host animal or cultured antibody-producing cells therefrom are generally in keeping with established and conventional techniques for antibody stimulation and production. While mice are frequently employed as the test model, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant (or other suitable adjuvant) by subcutaneous injection at multiple sites. 7 to 14 days later animals are bled and the serum is assayed for anti-antigen titer. Animals are boosted until the titer plateaus. Preferably, the animal is boosted with the conjugate of the same antigen, but conjugated to a different protein and/or through a different cross-linking agent. Conjugates also can be made in recombinant cell culture as protein fusions. Also, aggregating agents such as alum are used to enhance the immune response.

After immunization, monoclonal antibodies can be prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones producing the desired antibody. The hybridoma technique described originally by Kohler and Milstein, *Eur. J Immunol.* 6:511 (1976), and also described by Hammerling et al., In: *Monoclonal Antibodies and T-Cell Hybridomas*, Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody producing cells and the myeloma be from the same species.

The hybrid cell lines can be maintained in culture in cell culture media. The cell lines of this invention can be selected and/or maintained in a composition comprising the continuous cell line in hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are then sterile filtered. Where the antibody is a polyclonal antibody, it is generally affinity purified using an affinity column generated from the antigen of interest so as to provide a substantially specific capture antibody. Affinity chromatography is usually preceded by other purification techniques, such as liquid chromatography.

In a further embodiment, antibodies or antibody fragments can be isolated from antibody phage libraries generated via the techniques described in McCafferty et al., *Nature*, 348:552–554 (1990), using the flag polypeptide, rPTK, or a fragment thereof, to select for a suitable antibody or antibody fragment. Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Mark et al., *Bio/Tecbhnol.* 10:779–783 [1992]), as well as combinatorial infection and in vivo recombination as a strategy for constructing very large phage libraries (Waterhouse et al., *Nuc. Acids Res.*, 21:2265–2266 [1993]). Thus, these techniques are viable alternatives to traditional monoclonal antibody hybridoma techniques for isolation of "monoclonal" antibodies which are encompassed by the present invention.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-rPTK or anti-flag polypeptide monoclonal antibody herein. Thus, the antibody may be made by recombinant DNA methods (Cabilly et al., U.S. Pat. No. 4,816,567).

Binding of the capture agent is not affected by the presence or absence of a ligand bound to the receptor and the capture agent does not sterically block access to the phosphorylated tyrosine(s) by the anti-phosphotyrosine antibody. Furthermore, the capture agent does not, of course, activate the receptor of interest. In order to screen for an antibody having these characteristics, the procedure outlined in FIG. 3 can be carried out.

First, once the capture agent (e.g. an antibody or streptavidin) has been chosen, binding to either the receptor or the flag polypeptide (where a receptor construct is to be used in the assay) is confirmed. This can be determined by flow cytometric analysis, immuno-precipitation or antigen-coat ELISA, for example. Flow cytometric analysis has been described above. Immunoprecipitation usually involves lysing the cells (having the receptor or receptor construct) in non-ionic detergent (e.g. 0.5% Triton X-100) in a suitable buffer (e.g. PBS) and the cell lysates thus obtained are then incubated with the potential anti-receptor or anti-flag polypeptide capture agent. The immune complexes are precipitated with either (a) anti-capture agent antibodies in the presence of polyethylene glycol (PEG) which enhances precipitation of the immune complex or with (b) insoluble (e.g. agarose bound) protein A or protein G. The immunoprecipitated material is then analyzed by polyacrylamide gel electrophoresis (PAGE). For antigen-coat ELISA, ELISA wells are coated overnight with either the purified receptor, purified flag polypeptide or purified receptor construct. The coated wells are then exposed to the potential capture agent and screened with HRPO-conjugated species specific anti-capture agent antibody.

The ability of the capture agent to bind to the receptor or flag polypeptide in the presence of a ligand to the receptor is also confirmed. This can be analyzed by incubating the receptor or receptor construct with a known ligand for the receptor (e.g. the endogenous growth factor or an agonist antibody thereto). Flow cytometric analysis, immunoprecipitation or antigen-coat ELISA can then be performed substantially as described above to investigate binding of the capture agent.

Assuming the capture agent is suitable as determined by the preceding two steps, it is then shown that the capture agent does not induce receptor activation (i.e. autophosphorylation) either before or after cell lysis. Thus, the cell-bound receptor or receptor construct is exposed to either the potential capture agent or a negative control (e.g. a control antibody which does not activate the receptor). Following cell lysis, the receptor or receptor construct can be subjected to western blot analysis using labeled anti-phosphotyrosine antibodies. See, e.g., Glenney et al., *Journal of Immunological Methods* 109:277–285 (1988); Kamps, *Methods in Enzymoloy* 201:101–110 (1991); Kozma et al., *Methods in Enzymology* 201:28–43 (1991); or Holmes et al., *Science* 256:1205–10 (1992). To establish whether the capture agent induces receptor activation following cell lysis, a trial run of the KIRA ELISA (with both the capture agent and a negative control as discussed above) can be performed.

Finally, the ability of an anti-phosphotyrosine antibody (e.g. biotinylated anti-phosphotyrosine antibody) to bind the activated receptor in the presence of the potential capture agent is confirmed by a trial run in the KIRA ELISA disclosed herein.

Assuming the capture agent meets all the criteria specified above, it has good potential for use in the KIRA ELISA.

Once a suitable capture agent has been prepared, the second solid phase is coated therewith. Between about 0.1 to 10 µg/ml of capture agent can be added to each well of the second assay plate using a pipette, for example. The capture agent is often provided in a buffer at a high pH (e.g., between about 7.5 to 9.6) so that it has an increased overall charge and therefore displays enhanced binding to the second assay plate. Usually, the capture agent will be incubated in the wells for between about 8 to 72 hours to enable a sufficient coating of the capture agent to form on the inside walls of the wells. This incubation is generally carried out at low temperatures (e.g., between about 3–8° C.) to avoid or reduce degradation of the capture agent.

Following incubation, the wells of the plate are decanted and tamped lightly with an absorbent substrate. Non-specific binding is then blocked. In order to achieve this, a block buffer, is added to the wells. For example, a block buffer containing bovine serum albumin (BSA) such as that sold by Intergen Company, Purchase, N.Y., is suitable. It has been found that addition of between about 100 to 200 µl of block buffer to each well followed by gentle agitation at room temperature for between about 1–2 hours is sufficient to block non-specific binding. It is also possible to add the block buffer directly to the cell lysate obtained in the previous step rather than to the second assay plate.

Following this, the capture agent-coated plates are washed several times (usually between about 3–8 times) with a wash buffer. The wash buffer can comprise phosphate buffered saline (PBS) at pH 7.0 to 7.5, for example. However, other wash buffers are available which can also be used. Conveniently, an automated plate washer, such as the ScanWasher 300 (Skatron Instruments, Inc., Sterling, Va.) can be used for this, and other, washing steps of the assay.

B. Measuring Tyrosine Phosphorylation

The activated, solubilized rPTK (or receptor construct) is then added to the wells having the capture agent adhering thereto. As a general proposition, about 80% of cell lysate obtained as mentioned under Section 1E above can be added to each well (i.e., about 60 to 160 µl depending on the original volume of the wells). The lysate is incubated with the capture agent for an adequate period of time to enable the rPTK to be captured in the wells, e.g., from 1 to 3 hours. Incubation can be carried out at room temperature.

Unbound cell lysate is then removed by washing with wash buffer. Following this washing step, an amount of the anti-phosphotyrosine antibody which is equal to, or less than, the amount of block buffer added previously, is added to each well. For example, about 50 to 200 µl of an anti-phosphotyrosine antibody preparation having between about 0.3 to 0.5 µg/ml of antibody in a suitable buffer (e.g., PBS with a detergent such as those included in the lysis buffer) is added to the well. This is followed by a washing step to remove unbound anti-phosphotyrosine antibody.

Tyrosine phosphorylation is then quantified by the amount of anti-phosphotyrosine antibody binding to the second solid phase. Many systems for detecting the presence of an antibody are available to those skilled in the art. Some examples follow.

Generally, the anti-phosphotyrosine antibody will be labelled either directly or indirectly with a detectable label. Numerous labels are available which can be generally grouped into the following categories:

(a) Radioisotopes, such as $^{35}S$, $^{14}C$, $^{125}I$, $^3H$, and 131I. The antibody can be labeled with the radioisotope using the techniques described in *Current Protocols in Immunology*, supra, for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in *Current Protocols in Immunology*, supra, for example. Fluorescence can be quantified using a fluorimeter (nynatech).

(c) Various enzyme-substrate labels are available and U.S. Pat. No. 4,275,149 provides a review of some of these. The enzyme generally catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a Dynatech ML3000 chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., methods for the Preparation of Enzyme-Antibody Conjugates for use in Enzyme Immunoassay, in *Methods in Enzym.* (ed J. Langone & H. Van Vunakis), Academic press, New York, 73: 147–166 (1981) and *Current Protocols in Immunology*, supra.

Examples of enzyme-substrate combinations include, for example:

(i) Horseradish peroxidase (HRPO) with hydrogen peroxidase as a substrate, wherein the hydrogen peroxidase oxidizes a dye precursor (e.g. orthophenylene diamine [OPDD or 3,3'5,5'-tetramethyl benzidine hydrochloride [TMB]).

(ii) alkaline phosphatase (AP) with para-Nitrophenyl phosphate as chromogenic substrate.

(iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. Nos. 20 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. See, *Current Protocols in immunology*, supra, for a review of techniques involving biotin-avidin conjugation. Alternatively, to achieve indirect conjugation of the label with the antibody, the antibody is conjugated with a small hapten (e.g. digoxin) and one of the different types of labels mentioned above is conjugated with an anti-hapten antibody (e.g. anti-digoxin antibody). Thus, indirect conjugation of the label with the antibody can be achieved.

In another embodiment of the invention, the anti-phosphotyrosine antibody need not be labeled, and the presence thereof can be detected using a labeled anti-antiphosphotyrosine antibody (e.g. anti-mouse anti-phosphotyrosine antibody conjugated with HRPO).

In the preferred embodiment, the anti-phosphotyrosine antibody is labeled with an enzymatic label which catalyzes a color change of a substrate (such as tetramethyl benzimidine [TMB], or orthaphenylene diamine [OPD]). Thus, the use of radioactive materials is avoided. A color change of the reagent can be determined spectrophotometrically at a suitable wavelength (e.g. 450 nm for TMB and 490 nm for OPD, with a reference wavelength of 650 nm).

3. Intracellular Kinase Activity

The assay described herein is also useful for measuring phosphorylation and/or activation of intracellular kinases (e.g. cytoplasmic tyrosine kinases and/or cytoplasmic serine-threonine kinases). Phosphorylation of these molecules can occur as a consequence of trans-phosphorylation of the intracellular kinase by a kinase receptor or "receptor complex" (which comprises one or more kinase receptors residing in a cell membrane). Examples of intracellular tyrosine kinases include insulin receptor substrate I (IRS-1), Shc, Ras and GRB2, for example. Antibodies to human Shc, human Ras and GRB2 can be obtained commercially from UBI, N.Y., which can be used as capture agents for these tyrosine kinases. Examples of intracellular serine-threonine kinases include MEK and MAPK.

In order to measure phosphorylation of these kinases, the procedure is essentially as described above except that a chimera of the intracellular kinase and the flag polypeptide is normally formed (i.e. a "kinase construct"). Alternatively, the cell has an endogenous intracellular kinase or is transformed with nucleic acid encoding an intracellular kinase of interest. Generally, a eukaryotic cell will be transformed with nucleic acid encoding a kinase construct. Upon expression of the nucleic acid, the kinase or kinase construct will reside intracellularly (i.e. in the cytoplasm). The cells comprising the kinase or kinase construct are subjected to the KIRA as discussed above. Exposure to the agonist may result in trans-phosphorylation of the intracellular kinase which can be quantified in the ELISA as elaborated above. The capture agent in the ELISA binds to either the intracellular kinase or to the flag polypeptide.

4. Serine-Threonine Kinase Activity

This assay is further useful for measuring phosphorylation and/or activation of serine-threonine kinases. The term "serine-threonine kinases" refers to a kinase which phosphorylates a substrate which has at least one phosphate accepting alcohol group. The serine-threonine kinase is usually a "receptor" insofar as it has a ligand-binding ECD, TM domain and ICD. The ICD usually comprises a catalytic kinase domain and generally has one or more phosphate accepting serine and/or threonine residues. Examples of intracellular serine-threonine kinases include MEK and MAPK. See section 3 above for a discussion as to measuring phosphorylation of intracellular serine-threonine kinases. Examples of serine-threonine kinase receptors include daf-1, activin type II receptor (ActR-II), activin type IIB receptor (ActR-IIB), TGF-β type II receptor (TβR-II), activin receptor-like kinase (ALK) -1, -2, -3, -4 and TGF-β type I receptor (TβR-1)/ALK-5. See ten Dijke et al., supra. The serine-threonine kinase assay is essentially the same as described above for tyrosine kinases, except that phosphorylation is quantified using anti-phosphoserine and/or anti-phosphothreonine antibodies. Anti-phosphoserine and anti-phosphothreonine monoclonal antibodies can be purchased from Sigma Immuno Chemicals, St. Louis, Mo., for example.

5. Phosphatase Activity

Phosphatase activity can similarly be measured using the assay described herein. Phosphatase enzymes are able to dephosphorylate phosphorylated tyrosine, serine and/or threonine residues (i.e. liberate inorganic phosphate from phosphoric esters of such amino acid residues). Generally the phosphatase enzyme is specific for either tyrosine residues or serine-threonine residues but sometimes can dephosphorylate tyrosine, serine and threonine residues. Sometimes "endogenous" phosphatase activity is measured and this refers to the activity of phosphatase enzyme(s) which exist in nature in a selected cell.

In order to quantify endogenous phosphatase activity, cells possessing at least one phosphatase are stimulated in the presence and absence of one or more phosphatase inhibitors. Examples of protein tyrosine phosphatase (PTPase) inhibitors include sodium orthovanadate and sodium molybdate (Sigma Chemical Co., St. Louis, Mo.). ICK Biochemicals supply okadaic acid which is a serine-threonine phosphatase inhibitor. As a general proposition, between about 1–10 $\mu$M phosphatase inhibitor can be added to each well of the assay plate. In all other respects, the assay is performed essentially as discussed above. Thus, the ability of endogenous phosphatases to dephosphorylate a kinase in the selected cell can be quantified.

In the preferred embodiment, a phosphatase enzyme of interest can be studied. Examples of protein tyrosine phosphatases (PTPases) include PTP1B, PTPMEG, PTP1c, Yop51, VH1, cdc25, CD45, HLAR, PTP18, HPTP$\alpha$ and DPTP10D. See Zhang and Dixon, *Adv. Enzym.* 68: 1–36 (1994). Examples of protein serine-threonine phosphatases include PP1, PP2A, PP2B and PP2C. See *Meth, Enzvm.*, ed Hunter & Sefton, Academic press, New York, 201:389–398 (1991). These proteins can be purchased commercially or made using the recombinant techniques described herein. To measure phosphatase activity, the KIRA ELISA can be performed essentially as described above with the following modifications. Following capture of the kinase or kinase construct (e.g. receptor construct) to the second solid phase and the washing step (to remove unbound cell lysate), the phosphatase of interest is added to the wells of the second assay plate and incubated with the adhering kinase or kinase construct. For example, between about 50–200 $\mu$l of the phosphatase in a suitable dilution buffer (see *Meth. Enzvm.*, ed Hunter & Sefton, Academic press, New York, 201:416-440 (1991) can be added to each well. This is generally followed by gentle agitation at room temperature (or 37° C.) for between about 30 min to 2 hours to allow the phosphatase to dephosphorylate the kinase. Following washing to remove the phosphatase, the decreased degree of phosphorylation of the kinase relative to the control (i.e. no phosphatase added) is quantified by ELISA as described earlier herein.

6. Kits

As a matter of convenience, the reagents can be provided in a kit, i.e., a packaged combination of reagents, for combination with the analyte in assaying the ability of the analyte to activate or prevent activation of a rPTK of interest. The components of the kit will be provided in predetermined ratios. Thus, a kit will comprise the specific second solid phase for the assay as well as the anti-flag polypeptide capture agent either packaged separately or captured to the second solid phase (e.g. a microtiter plate). Usually, other reagents, such as the anti-phosphotyrosine antibody labelled directly or indirectly with an enzymatic label will also be provided in the kit. Where the detectable label is an enzyme, the kit will include substrates and cofactors required by the enzyme (e.g. a substrate precursor which provides the detectable chromophore or fluorophore). In addition, other additives may be included such as stabilizers, buffers (e.g. a block buffer and a lysis buffer) and the like. Conveniently, the kit can also supply the homogeneous population of cells which have been transformed with the receptor construct. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration. The kit also suitably includes instructions for carrying out the KIRA ELISA.

7. Uses for the Assay

This application provides two assays which are useful for reliable, sensitive and quantitative detection of kinase activation. The first assay can be used where a kinase receptor-specific capture antibody having the desired characteristics herein described is available or has been prepared. The second assay is a generic assay which enables activation of any kinase receptor to be measured via the use of a flag polypeptide and a capture agent which binds specificity thereto.

These assays are useful for identifying novel agonists/antagonists for a selected kinase receptor. Also, the assay provides a means for studying ligand-receptor interactions (i.e., mechanism studies). Also the presence of an endogenous receptor in a selected cell line can be quantified using the assay. The assays are further useful for identifying the presence of a ligand for a selected kinase receptor in a biological sample and, e.g., establishing whether a growth factor has been isolated following a purification procedure. It is desirable to have an assay for measuring the ability of these growth factors to activate their respective receptors.

The assay also has clinical applications for detecting the presence of a ligand for a selected rPTK (e.g. the insulin receptor) in a biological sample taken from a human and thus patients having elevated or depressed levels of the ligand can be identified. This is particularly desirable where elevated or depressed levels of the ligand cause a pathological condition. Accordingly, candidates for administration of the selected ligand (e.g. insulin) can be identified through this diagnostic method. It is possible, using the assay disclosed herein, to assay the pK of agonists or antagonists administered to a patient. This assay also facilitates the detection of shed receptor in a biological sample.

The assay is also useful to quantify phosphatase activity of endogenous phosphatases or, in the preferred embodiment, a phosphatase of interest. This can be used for screening phosphatase inhibitors, for example.

Below are examples of specific embodiments for carrying out the present invention. The examples are offered for illustrative purposes only, and are not intended to limit the scope of the present invention in any way.

All publications, patents and patent applications cited herein, whether supra or infra, are hereby incorporated by reference in their entirety.

EXAMPLE 1

KIRA ELISA of the HER2 Receptor

The assay system described in this example was developed to measure the extent of autophosphorylation as a result of the interactions between the HER2 receptor and its specific activator, heregulin (HRG). The overexpression of pB185$^{HER2}$ has been correlated with poor clinical outcome in a number of epithelial-derived cancers. Heregulin and its rodent homologue, neu differentiation factor (NDF), were originally purified based on their ability to stimulate the autophosphorylation of a 185 kDa protein in the breast carcinoma cell lines MCF-7 and MDA-453, respectively. In this embodiment of the invention, the cell line expressing the tyrosine kinase receptor DNA (either endogenous or transformed) is adherent and there is an antibody (e.g. monoclonal or affinity purified polyclonal) capable of specifically binding the receptor such that it neither stimulates autophosphorylation in the absence of ligand nor suffers impaired binding due to the presence of bound ligand. Standard curve preparations and many samples may easily be run simultaneously in replicate and at several dilutions using this assay, readily allowing quantitation of ligand activity in a large number of unknown samples.

(i) Capture Agent Preparation

Polyclonal anti-HER2 antibody was isolated from pooled immune sera from New Zealand White rabbits immunized with the extracellular domain of the HER2 molecule (Fendly et al., *Journal of Biological Response Modifiars* 9:449–455 [1990]). The rHER2 ECD specific antibodies were affinity purified using an FPLC (Pharmacia Biotech, Inc, Piscataway, N.J.) with an affinity column generated from rHER2 ECD conjugated to Avidgel F (Bioprobe International, Inc, Tustin, Calif.). The resulting purified antibody stock was 0.829 mg/ml in phosphate buffered saline (PBS), pH 7.4, and was stored as 0.5 ml aliquots at −20° C.

(ii) Anti-phosphotvrosine Antibody Preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligand

The recombinant truncated form of β1heregulin (Mw= 7.88 Kd) corresponding to residues 177–244 (ERGβ1$_{177-224}$) was produced in *E. coli* and purified to homogeneity as described in Holmes et al., *Science*, 256: 1205–1210 (1992) and was stored at 4° C. as an 89.7 μM stock solution in 50 mM Tris/HCl, pH 7.5.

(iv) Adherent Cells

MCF-7 (ATCC-HTB 22), an adherent cell line isolated from a human breast adenocarcinoma, was obtained from American Type Culture Collection (ATCC, Rockville, Md.). MCF-7 cells have been shown to produce measurable levels of surface p185$^{HER2}$ by both FACS and ELISA analysis. The cells were maintained in 150 cm$^2$ tissue culture flasks (Corning Inc, Corning, N.Y.) and utilized when at cell densities of 60% to 75% confluency. For the assay, 2×10$^5$ cells were seeded per well in flat-bottom microtiter plates (Falcon 3072, Becton Dickinson Labware, Lincoln Park, N.J.) cultured overnight at 37° C. in 5% CO$_2$. Cells were grown in F12/ DMEM 50:50 Gibco as a custom formulation (Gibco/BRL, Life Technologies, Grand Island, N.Y.). The medium was supplemented with 10% FBS (HyClone, Logan, Utah), 25 mM HEPES (Gibco) and 2 mM L-glutamine (Gibco).

(v) KIRA ELISA

MCF-7 cells (2×10$^5$) in 100 μl media were added to each well in a flat-bottom-96 well culture plate and cultured overnight at 37° C. in 5% CO$_2$. The following morning the well supernatants were decanted, and the plates were lightly tamped on a paper towel. 50 μl of media containing either experimental samples or the recombinant HRGβ1$_{177-244}$ standards (3000, 1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 μM leupeptin (ICN Biochemicals), and 2 mM sodium orthovanadate (Na$_3$VO$_4$, Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the affinity-purified polyclonal anti-HER2 ECD (1.0 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-HER2 ECD coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized p185$^{HER2}$ from the cell-culture microtiter well was transferred (85 μl/well) to anti-rHER2 ECD coated and blocked ELISA well and was incubated for 2 h at room temperature with gentle agitation. The unbound receptor was removed by washing with wash buffer and 100 μl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e. 400 pg/ml, was added to each well. After incubation for 2 h at room temperature the plate was washed and 100 μl of HRPO-conjugated streptavidin (Zymed Laboratories, S. San Francisco, Calif.) diluted 1:10000 in dilution buffer was added to each well. The plate was incubated for 20 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 μl/well 1.0 M H$_3$PO$_4$. The absorbance at 450 nm was read with a reference wavelength of 650 nm (ABS$_{450/650}$) , using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 7 was generated by stimulating MCF-7 cells with 3000, 1000, 333, 111, 37, 12, 4, or 0 pM HRGβ1$_{177-244}$ and presented as pM HRGβ1$_{177-244}$ vs. mean ABS$_{450/650}$ ±sd using the DeltaSoft program. Sample concentrations were obtained by interpolation of their absorbance on the standard curve and are expressed in terms of pM HRGΘ1$_{177-244}$ activity.

When the data were fitted to a 4-parameter nonlinear least squares equation, they resulted in a correlation coefficient of 0.9998. For the data shown in FIG. 7, the EC$_{50}$ of receptor activation by HRGβ1$_{177-244}$ was 373 pM. To demonstrate the highly reproducible nature of the p185$^{HER2}$ KIRA ELISA, seven standard curves were generated over the period of one month and the $EC_{50}$'s are averaged. This gives an $EC_{50}$ave for HRGβ1$_{177-244}$ of 360 ±40 pM (average ±SD).

(vi) Intra- and Inter-assay Precision and Assay Specificity

The intra-assay variability was determined by performing the p185$^{HER2}$ KIRA ELISA on three separate days. For each test, the standard curve is run in triplicate. Controls with HRGβ1$_{177-224}$ corresponding to high (1000 pM), mid (200 pM) and low (40 pM) were assayed in 24 replicates. The ABS$_{450/650}$ of the individual test samples were converted to pM HRGβ1$_{177-244}$ activity and the 24 converted values for each test concentration were averaged. The data are expressed as averaged value and % coefficient of variation (% cv; [(intra-assay standard deviation/intra-assay averaged calculated value)×100]. See Table 1A below.

TABLE 1

Intra- and Inter-assay Variation

| High Value[a] | | Mid Value | | Low Value | |
|---|---|---|---|---|---|
| Average Value (pM) | | Average Value (pM) | % cv | Average Value (pM) | % cv |
| A. Intra-assay Precision (n = 24 per test) | | | | | |
| | % cv[b] | | | | |
| Test #1 1256 | 19.5% | 209 | 10.8% | 33 | 12.3% |
| Test #2 1078 | 10.0% | 196 | 5.1% | 38 | 7.5% |
| Test #3 999 | 14.3% | 196 | 6.3% | 35 | 11.3% |
| B. Inter-assay Precision (n = 3) | | | | | |
| | % cv[c] | | | | |
| 1100 | 4.3% | 200 | 6.3% | 34 | 9.0% |

[a]Expected high value: 1000 pM; mid value: 200 pM; low value: 40 pM
[b]Intra-assay % cv determined as intra-assay sd/intra-assay average × 100
[c]Inter-assay % cv determined as inter-assay sd/inter-assay average × 100

The intra-assay variability of the KIRA ELISA was within acceptable limits despite the fact that the assay actually consists of both bioassay and ELISA components. The coefficients of variance (%) for the highest values were under 20% and for the mid and low values were at or under 10%.

The inter-assay variability was determined by averaging the values from upper-most three adjacent wells (of the 24 wells run) for a given sample concentration from each run. The three separate averages for each test concentration were then averaged. The data were expressed as averaged value and % cv [(inter-assay standard deviation/inter-assay averaged value) ×100]. See Table 1B. above. The inter-assay variability of the KIRA ELISA was within acceptable limits.

In order to confirm the specificity of the assay, MCF-7 cells were stimulated with either HRGβ1$_{177-244}$ at 3000, 1000, 333, 111, 37, 12, 4 or 0 pM or insulin-like growth factor-1 (IGF-1), epidermal growth factor (EGF), vascular endothelial growth factor (VEGF), or insulin at 30000, 10000, 3333, 1111, 370, 120, 40 or 0 pM. The p185$^{HER2}$ KIRA ELISA was then performed as described above. The results are depicted in FIG. 8.

The p185$^{HER2}$ KIRA ELISA was clearly specific for heregulin. While HRGβ1$_{177-224}$ induced normal receptor stimulation and autophosphorylation, the closely related EGF gives only a slight stimulation (OD$_{450/650}$=0.239) at the highest concentration tested (100 nM). Since EGF-R is produced in MCF-7 cells, this signal is likely due to EGF receptor transphosphorylation of p185$^{HER2}$. Neither insulin-like growth factor-1 (IGP-1), vascular endothelial growth factor (VEGF) nor insulin have any detectable effect on the MCF-7 p185$^{HER2}$ KIRA ELISA, the latter despite the fact that MCF-7 cells produce active insulin receptors.

The results presented in this example demonstrate that the KIRA ELISA is a useful method for assaying ligand activation of a kinase receptor, e.g., heregulin activation of the p185$^{HER2}$ receptor. Levels of receptor activation in terms of tyrosine phosphorylation ate easily quantified and an $EC_{50}$ for a given ligand is readily determined. One potential use for this assay would be to screen compounds for receptor agonist or antagonist activities. The potential throughput for this assay greatly surpasses that of Western blot analysis. Since the cell-culture portion of the assay is conducted in 96-well plates, many samples may be run in replicate at different dilutions at one time in a one-day assay.

EXAMPLE 2

KIRA ELISA of the Rse Receptor

Mark et al., *Journal of Biological Chemistry* 269(14):10720–10728 (1994) describe isolation of the Rse receptor protein tyrosine kinase from human and murine tissues. This Rse receptor with a carboxyl-terminal flag polypeptide (i.e. Rse.gD) was subjected to the KIRA ELISA described herein. The experimental procedure is outlined below.

(i) Capture Agent Preparation

Monoclonal anti-gD (clone 5B6) was produced against a peptide from Herpes simplex virus glycoprotein D (Paborsky et al., *Protein Engineering* 3(6):547–553 [1990]). The purified stock preparation was adjusted to 3.0 mg/ml in phosphate buffered saline (PBS), pH 7.4 and 1.0 ml aliquots were stored at −20° C.

(ii) Anti-phosphotyrosine Antibody Preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Licand

Since the endogenous ligand for the Rse receptor was not available, an agonist antibody for the Rse receptor was prepared which forms the ligand for the KIRA ELISA described in this Example. To generate the agonist antibody, a Rse.IgG chimera was generated. Briefly, the coding sequence of the ECD of Rse was fused to that of the human IgG-γ1 heavy chain in a multi-step process. PCR was used to generate a fragment with a unique BstEII site 3' to the coding sequences of the Rae amino acid 428. The PCR product was joined to the human IgG-γ$_1$ heavy chain cDNA through a unique BstEII site in that construct (Mark et al., *J. Cell. Biol.*, 267: 26166–26171 [1992]). The resulting construct (termed pRK.bpTK3.IgG.fusion) contained the coding sequences for amino acids 375–428 of Rse joined to those encoding human IgG-γ$_1$ heavy chain. The remaining portion of the Rse ECD (amino acids 1–374) was then added by linkage through the Bam HI site in pRK.bpTK3.IgG.fusion to yield pRK.Rse.IgG.

To generate stable cell populations expressing Rse.IgG, the cDNA encoding Rse.IgG was subcloned into the episomal CMV-driven expression plasmid pCIS.EBON, a pRK5 derivative disclosed in Cachianes et al., *Bio. TechniAues*, 15: 225–259 (1993). Human fetal kidney 293 cells (obtained from ATCC, 12301 Parklawn Drive, Rockville, Md., USA) were transfected by the calcium phosphate technique. Cell monolayers were incubated for four hours in the presence of the DNA precipitate, glycerol shocked, and cultured in F12:DMEM (1:1) containing 2 mM glutamine, 10% fetal bovine serum, penicillin and streptomycin. After 48 hours, populations were replated in media containing G418 to select for a stable population of cells. Conditioned media was collected from cells expressing Rse.IgG nucleic acid that have been cultured in serum-free media for 72 hours in the absence of G418.

Rse.IgG was purified by affinity chromatography on a protein A column using procedures as described by Chamow, S. M., et al., *Biochemistry*, 29:9665–9891 (1990) with the following minor modifications. Conditioned media collected from cells expressing the Rse.IgG was adjusted to 0.1 M citrate pH 6.0 and loaded directly onto a protein A column (Repligen). The column was washed with 0.1 M citrate, pH 6.0, and was eluted with 3 M $MgCl_2$ with 10% glycerol. Fractions were pooled and desalted on a PD-10 column, dialyzed and concentrated against PBS. Protein concentrations were determined by an ELISA against human IgG (Fc). The protein was analyzed for purity by Coomassie staining of PAGE gels.

Polyclonal antibodies were generated in New Zealand white rabbits against the Rse.IgG formed as described above. 4 μg of Rse.IgG in 100μL PBS was emulsified with 100 μL Freund's adjuvant (complete adjuvant for the primary injection and incomplete adjuvant for all boosts). For the primary immunization and the first boost, the protein was injected directly into the popliteal lymph nodes (Sigel et al., *Methods Enzymol.*, 93, 3–12 [1981]). For subsequent boosts, the protein was injected into subcutaneous and intramuscular sites. 1.3 μg protein/kg body weight was injected every 3 weeks with bleeds taken 1 and 2 weeks following each boost. The polyclonal antisera generated was then precipitated in 50% ammonium sulphate.

The resultant, purified polyclonal antisera is called "19B" herein. To confirm the ability of the 19B antisera to induce autophosphorylation of the Rse receptor, serum starved 3T3.gD.R11 cells (transformed with nucleic acid encoding the Rse receptor with an amino terminal gD flag polypeptide [i.e. gD.Rse] using the techniques described in Mark et al., *Journal of Biological Chemistry* 269(14):10720–10728 [1994]) or NIH3T3 cells were exposed to pre-immune serum or 19B polyclonal antisera at a 1:200 dilution for 10 minutes. The gD.Rse protein was immunoprecipitated from extracts using the anti-gD monoclonal antibody 5B6. Proteins were fractionated on 7% SDS-PAGE under reducing conditions and transferred to nitrocellulose. Phosphorylation of Rse was detected with labelled anti-phosphotyrosine antibody. Treatment of the 3T3.gD.R11 cells with 19B antisera stimulated the phosphorylation of the 140 kD gD.Rse protein. This increase was not observed in cells treated with pre-immune sera.

The purified 19B polyclonal antisera was stored at 4° C. as an 2.8 mg/ml stock solution in PBS, pH 7.5.

(iv) Preparation of Rse.gD Nucleic Acid

Synthetic double stranded oligonucleotides were used to reconstitute the coding sequence for the C-terminal 10 amino acids (880–890) of human Rse and add an additional 21 amino acids containing an epitope for the antibody 5B6 and a stop codon. The final sequence of the synthetic portion of the fusion gene was: coding strand:
5'-TGCAGCAAGGGCTACTGCCACACTCGAGCTGC
  GCAGATGCTAGCCTCAAGATGGCT G ATC-
  CAAATCGATTCCGCGGCAAAGATCTTCCGG
  TCCTGTAGAAGCT-3' (SEQ ID NO: 10)
noncoding (anti-sense) strand:
5'-AGCTTCTACAGGACCGGAAGATCTTTGCCGCG
  GAATCGATTTGGATCAGCCATCTT G AGGCTAG-
  CATCTGCGCAGCTCGAGTGTGGCAGT
  AGCCCTTGCTGCA-3' (SEQ ID NO: 11).

The synthetic DNA was ligated with the cDNA encoding amino acids 1–880 of human Rse at the PstI site beginning at nucleotide 2644 of the published human Rse cDNA sequence (Mark et al., *Journal of Biological Chemistry* 269(14):10720–10728 [1994]) and HindIII sites in the polylinker of the expression vector pSVI7.ID.LL (See FIG. 16; SEQ ID NO: 9) to create the expression plasmid pSV.ID.Rse.gD. Briefly, the expression plasmid comprises a dicistronic primary transcript which contains sequence encoding DHFR bounded by 5' splice donor and 3' splice acceptor intron splice sites, followed by sequence that encodes the Rse.gD. The full length (non-spliced) message contains DHFR as the first open reading frame and therefore generates DHFR protein to allow selection of stable transformants.

(v) Cell Transformation dp12.CHO cells (EP 307,247 published Mar. 15, 1989) were electroporated with 20 μgs of pSV.ID.Rse.gD which had been linearized at a unique NotI site in the plasmid backbone. The DNA was ethanol precipitated after phenol/chloroform extraction and was resuspended in 20 μl 1/10 Tris EDTA. Then, 10 μg of DNA was incubated with $10^7$ CHO.dp12 cells in 1 ml of PBS on ice for 10 min. before electroporation at 400 volts and 330 μf. Cells were returned to ice for 10 min. before being plated into non-selective medium. After 24 hours cells were fed nucleoside-free medium to select for stable DRFR+clones.

(vi) Selection of Transformed Cells for Use in the KIRA ELISA

To identify a cell line that expresses Rse.gD nucleic acid, candidate clones were screened by fluorescence activated cell sorting (FACS) analysis using the polyclonal antiserum 19B generated as described above, which recognizes epitopes in the extracellular domain of Rse. See FIG. 5, step (b).

To confirm that clones that scored positive in the FACS assay express full-length Rse.gD nucleic acid, cell lysates were prepared (Lokker et al., *EMBO J*, 11:2503–2510 [1992]) and solubilized Rse.gD was immunoprecipitated with the 19B antisera. The immunoprecipitated proteins were fractionated under reducing conditions using 7% PAGE, blotted onto nitrocellulose and then probed with the anti-gD 5B6 antibody which was detected with a horseradish peroxidase conjugated anti-mouse IgG antibody. See FIG. 5, step (c). The ability of Rse.gD in cell clones to be activated to undergo autophosphorylation in response to the 19B agonistic antibody was determined. Briefly, serum starved dp.CHO cells transformed with Rse.gD nucleic acid as described above were exposed to pre-immune or 19B anti-sera at a 1:200 dilution for 10 min. The Rse.gD protein was immunoprecipitated from extracts using the anti-gD 5B6 monoclonal antibody. Proteins were fractionated on 7% SDS-PAGE under reducing conditions and transferred to nitrocellulose. Phosphorylation of Rae was detected with labelled antiphosphotyrosine antibody. See FIG. 5, step (d).

(vii) Media

Cells were grown in F12/DMM 50:50 (Gibco/BRL, Life Technologies, Grand Island, N.Y.). The media was supplemented with lot diafiltered FBS (HyClone, Logan, Utah), 25 mM HEPES and 2 mM L-glutamine.

(viii) KIRA ELISA

Rse.gD transformed dp12. CHO cells (EP 307,247 published Mar. 15, 1989) were seeded ($5 \times 10^4$ per well) in the wells of a flat-bottom-96 well culture plate in 100 μl media and cultured overnight at 37° C. in 5% $CO_2$. The following morning the well supernatants were decanted, and the plates were lightly tamped on a paper towel. 100μl of media containing either experimental samples or 1:100, 1:200, 1:400, 1:B00, 1:1600, 1:3200 or 0 diluted, anti-Rse agonist polyclonal antibody (19B pAb) was then added to each well. The cells were stimulated at 37° C. for 30 min., the well supernatants were decanted, and the plates were once again lightly tamped on a paper towel. To lyse the cells and solubilize the receptors, 100 μl of lysis buffer was added to each well. Lysis buffer consisted of 150 mM NaCl containing 50 mM KEPES (Gibco), 0.5% Triton-X 100 (Gibco), 0.01% thimerosal, 30 KIU/ml aprotinin (ICN Biochemicals, Aurora, Ohio), 1mM 4-(2-aminoethyl)-benzenesulfonyl fluoride hydrochloride (AEBSF; ICN Biochemicals), 50 μM leupeptin (ICN Biochemicals), and 2 mM sodium orthovanadate ($Na_3VO_4$; Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 μg/ml in 50 mM carbonate buffer, pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized Rse.gD from the cell-culture microtiter well was transferred (85 μl/well) to anti-gD 5B6 coated and blocked ELISA well and was incubated for 2 h at room temperature with gentle agitation. The unbound Rse.gD was removed by washing with wash buffer and 100 μl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e. 400 pg/ml was added to each well. After incubation for 2 h at room temperature the plate was washed and 100μl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for 10 minutes, after which the color development was stopped by the addition of 100 μl/well 1.0 M $H_3PO_4$. The absorbance at 450 nm was read with a reference wavelength of 650 nm ($ABS_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curve shown in FIG. 10 was generated by stimulating Rse.gD transformed CHO cells with 1:100, 1:200, 1:400, 1:800, 1:1600, 1:3200 or 0 diluted, anti-Rse agonist antibody (19B) and presented as 1/dilution anti-Rse agonist antibody (19B) vs. mean $ABS_{450/650}$±sd using the DeltaSoft program.

The results presented in this example demonstrate that the KIRA ELISA is a useful method for assaying ligand activation of a receptor construct having a carboxyl terminal flag polypeptide, e.g., activation of Rse.gD. Levels of receptor activation in terms of tyrosine phosphorylation are easily quantified and an $EC_{50}$ for a given ligand (e.g. an agonist antibody for the receptor) is readily determined.

EXAMPLE 3

KIRA ELISA of the trk A, R and C Receptors

Neurotrophins belong to a family of small, basic proteins which play a crucial role in the development and maintenance of the nervous system. The first identified and probably best understood member of this family is nerve growth factor (NGF). See U.S. Pat. No. 5,169,762, issued Dec. 8, 1992. Recently, sequentially related but distinct polypeptides with similar functions to NGF have been identified. For example, brain-derived neurotrophic factor (BDNF), now also referred to as neurotrophin-2 (NT2), was cloned and sequenced by Leibrock et al. (*Nature* 341: 149–152 [1989]). Several groups identified a neurotrophic factor originally called neuronal factor (NF), and now referred to as neurotrophin-3 (NT3). (Ernfors et al., *Proc, Natl. Acad. Sci. USA*, 87: 5454–5458 [1990]; Höhn et al., *Nature*, 344: 339 [1990]; Maisonpierre et al., *Science*, 247: 1446 [1990]; Rosenthal et al., *Neuron*, 4: 767 [1990]; Jones and Reichardt; *Proc, Natl. Acad, Sci. USA*, 87: 8060–8064 [1990]; Kaisho et al., *FEBS Lett.*, 266: 187 [1990]). Neurotrophins-4 and -5 (NT4 and NT5) have been recently added to the family (Hallbook et al., *Nuron*, 6: 845–858 [1991]; Berkmeier et al., *Neuron*, 7: 857–866 [1991]; Ip et al., *Proc. Natl. Acad. Sci. USA*, 89: 3060–3064 [1992]).

Neurotrophins, similarly to other polypeptide growth factors, affect their target cells through interactions with cell surface rPTKs (called Trk receptors). The first member of the trk receptor family, trkA, was initially identified as the result of an oncogenic transformation caused by the translocation of tropomyosin sequences onto its catalytic domain. Later work identified trkA as a signal transducing receptor for NGF. Subsequently, two other related receptors, mouse and rat trkb (Klein et al., *EMBO J.*, 8: 3701–3709 [1989]; Middlemas et al., *Mol. Cell. Biol.*, 11: 143–153 [1991]; EP 455,460 published Nov. 6, 1991) and porcine, mouse and rat trkC (Lamballe et al., *Cell*, 66: 967–979 [1991]; EP 522,530 published Jan. 13, 1993), were identified as members of the trk receptor family. The structures of the trk receptors are quite similar, but alternate splicing increases the complexity of the family by giving rise to two known forms of trkA, three known forms of trkB (two without functional tyrosine kinase domains) and at least four forms of trkC (several without functional tyrosine kinase domain, and two with small inserts in the tyrosine kinase domain). Human trk A, B and C receptor sequences are disclosed in U.S. patent application Ser. No. 08/215,139, filed Mar. 18, 1994, specifically incorporated herein by reference.

The following KIRA ELISA was performed using trk A, B and C receptor constructs having amino-terminal flag polypeptides.

(i) Capture Agent Preparation

Monoclonal anti-gD (clone 5B6) was produced against a peptide from Herpes simplex virus glycoprotein D as discussed above in Example 2. The purified stock preparation was adjusted to 3.0 mg/ml in phosphate buffered saline (PBS), pH 7.4 and 1.0 ml aliquots were stored at −20° C.

(ii) Anti-Phosphotyrosine Antibody Preparation

Monoclonal anti-phosphotyrosine, clone 4G10, was purchased from Upstate Biologicals, Inc (UBI, Lake Placid, N.Y.) and biotinylated using long-arm biotin-N-hydroxysuccinamide (Biotin-X-NHS, Research Organics, Cleveland, Ohio).

(iii) Ligands

Nerve growth factor (NGF), neurotrophin 3 (NT3), and neurotrophin 5 (NT5) were prepared by recombinant techniques using the sequence data provided for each of these proteins in the above-mentioned references. The purified NGF, NT3 and NT5 were stored at 4° C. as stock solutions (180 µM, 5 8.8 µM and 26.9 µM, respectively) in PBS, pH 7.5.

(iv) Preparation of gD.trk Nucleic Acid

In order to express the various trk receptors with gD flags (i.e. gD.trk constructs), DNA constructs were made which encoded the signal and epitope of gD (see Paborsky et al., supra) fused to the amino terminus of the various trk receptors. These were made by inserting the trk receptor and gD sequences into pRK5 or pRK7 (Suva et al., *Science,* 237: 893–896 1987]) using standard molecular biology techniques, to generate the constructs shown in FIGS. 12–14. In addition to the gD.trk constructs, constructs were also made to express gD tagged trk.IgG fusion proteins (i.e., gD.trk.IgG). DNA constructs encoding the chimeras of trk extracellular domain and IgG-1 Fc domains were made with the Fc region clones of human IgG-1(Ashkenazi et al., *Immunoadhesins Intern Rev. Immunol.,* 10: 219–227 [1993]). More specifically, the source of the IgG-1 encoding sequence was the CD4-IgG-1 expression plasmid pRKCD4$_2$Fc$_1$ (Capon et al., *Nature,* 334: 525 [1989]; Byrn et al., *Nature,* 344: 667 [1990]) containing a cDNA sequence encoding a hybrid polypeptide consisting of residues 1–180 of the mature human CD4 protein fused to human IgG-1 sequences beginning at aspartic acid 216 (taking amino acid 114 as the first residue of the heavy chain constant region; Kabat et al., *Sequences of Proteins of Immunological Interest* 4th ed. [1987]), which is the first residue of the IgG-1 hinge after the cysteine residue involved in heavy-light chain bonding, and ending with residues 441 to include the CH2 and CH3 Fc domains of IgG-1. The CD4-encoding sequence was deleted from the expression plasmid pRKCD4$_2$Fc$_1$ and the vector was fused to DNA encoding the trk receptors, with the splice between aspartate 216 of the IgG-1 and valine 402 of trkA, threonine 422 of trkB, or threonine 413 of trkC. The gD tag was added to the amino terminus of each trk.IgG in the same way as for the gD.trk constructs.

(y) Cell Transformation

Human embryonic kidney 293 cells (obtained from ATCC, Rockville, Md.) were transiently transfected with the nucleic acid encoding gD.trk.IgG using a calcium phosphate protocol (Gorman, *DNA Cloning A Practical Agrroach* [Glover, D., ed.] Vol II: 143–190, IRL Press, Washington, D.C.). After twelve hours, the transfected cells were rinsed three times with serum free F12/DMEM 50:50 media (Gibco) and then serum free media was added for a 48 hour collection.

Cell lines stably expressing each of the gD.trk constructs were made by co-transfecting dp12. CHO cells (EP 307,247 published Mar. 15, 1989) with the pRK plasmids encoding the gD tagged trk receptors and a plasmid encoding DHFR, again using calcium phosphate mediated transfection.

The media mentioned above (having the gD.trk.IgG) was used without further purification in binding assays to assess the effects of the presence of the gD flag polypeptide on neurotrophin binding to the gD.trk.IgG polypeptides. DNA encoding untagged trk.IgG polypeptide was run in parallel as a control. trk.IgG and gD tagged trk.IgG containing cell supernatants were prepared as described and used in competitive displacement assays with the appropriate iodinated neurotrophin. NGF is used as ligand for trka, NT5 is used as ligand for trkb, and NT3 is used as a ligand for trkc. A summary of the results obtained is shown in the following table.

TABLE 1

Binding of Neurotrophins to trk.IgG

| | IC50 without gD | IC50 with gD |
|---|---|---|
| trkA | 68.4 +/− 11.9 pM | 68.8 +/− 3.0 pM |
| trkB | 31.1 +/− 15.6 pM | 12.1 +/− 18 pM |
| trkC | 31.1 +/− 1.1 pM | 30.2 +/− 0.7 pM |

(vi) Selection of Transformed Cells for Use in the KIRA ELISA

It was apparent from the preceding experiment that there was no observable change in the affinity of interaction of neurotrophins with their receptor due to the presence of the gD flag polypeptide on the amino terminus. Based on this result, cells were transformed with the gD.trk constructs for use in the KIRA ELISA using the techniques described in the previous section.

After two days, dpl2.CHO cells (EP 307,247 published Mar. 15, 1989) transformed with gD.trk constructs were selected for by growth in media without GHT, and after two weeks, growing cells were sorted by FACS analysis using the 5B6 monoclonal to select cells expressing the gD flag polypeptide on their surface. gD positive cells were cloned by plating at limiting dilution and resultant colonies were then rescreened by FACS analysis (using the anti-gD 5B6 monoclonal antibody), neurotrophin binding (as discussed above), tyrosine phosphorylation indicated by Western blot using an anti-phosphotyrosine antibody, gD expression by Western blot using th anti-gD 5B6 antibody, and immunocytochemistry using the 5B6 antibody. Clones which were positive were then recloned by limiting dilution and were subjected to the KIRA ELISA as described below.

(vii) Media

Cells were grown in F12/DMEM 50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA gD.trk transformed dp12.CHO cells (EP 307,247 published Mar. 15, 1989) were seeded (5×10$^4$ per well) in a flat-bottom-96 well culture plate in 100 µl media and cultured overnight at 37° C. in 5% CO$_2$. The following morning the well supernatants were decanted, and the plates were lightly tamped on a paper towel. $^{100}$µl of media containing either experimental samples or the recombinant purified NGF, NT3, or NT5 standards (3000, 1000, 333, 111, 37, 12, 4, and 0 pM) was then added to each well. The cells were stimulated at 37° C. for 30 min., the well supernatants were decanted, and the plates were once again lightly tamped on a paper towel. To lyse the cells and solubilize the receptors, 100 µl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICN Biochemicals), 50 µM leupeptin (ICN Biochemicals). and 2 mM sodium orthovanadate (Na$_3$VO$_4$; Sigma Chemical Co, St. Louis, Mo.). pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (0.5 µg/ml in 50 mM carbonate buffer, pH 9.6, 100 µl/well) was decanted, tamped on a paper towel and blocked with 150 µl/well of Block Buffer [PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% thimerosal) using an automated plate washer (ScanWasher 300, Skatron Instruments, Inc, Sterling, Va.).

The lysate containing solubilized gD.trk from the cell-culture microtiter well was transferred (85 µl/well) to anti-gD 5B6 coated and blocked ELISA well and was incubated for 2 h at room temperature with gentle agitation. The unbound gD.trk was removed by washing with wash buffer and 100 µl of biotinylated 4G10 (anti-phosphotyrosine) diluted 1:2000 in dilution buffer (PBS containing 0.5% BSA, 0.05% Tween-20, 5 mM EDTA, and 0.01% thimerosal), i.e., 400 pg/ml, was added to each well. After incubation for 2 h at room temperature the plate was washed and 100 µl of HRPO-conjugated streptavidin (Zymed Laboratories, S. San Francisco, Calif.) diluted 1:10000 in dilution buffer was added to each well. The plate was incubated for 30 minutes at room temperature with gentle agitation. The free avidin-conjugate was washed away and 100 µl freshly prepared substrate solution (tetramethyl benzidine; 2-component substrate kit; Kirkegaard and Perry, Gaithersburg, Md.) was added to each well. The reaction was allowed to proceed for 10 minutes, after which the color development was stopped by the addition of 100 µl/well 1.0 M $H_3PO_4$. The absorbance at 450 nm was read with a reference wavelength of 650 nm ($AS_{450/650}$) using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The standard curves shown in FIGS. 15A–15C were generated by stimulating gD.trk transformed CHO cells with 3000, 1000, 333, 111, 37, 12, 4, and 0 pM NGF, NT3 or NT5 and were presented as pM neurotrophin vs. mean $ABS_{450/650}$ ±sd using the DeltaSoft program. Sample concentrations were obtained by interpolation of their absorbance on the standard curve and are expressed in terms of pM neurotrophin activity.

The results presented in this example demonstrate that the KIRA ELISA is a useful method for assaying ligand activation of a receptor construct having an amino terminal flag polypeptide, e.g., activation of gD.trk receptor constructs. Levels of receptor activation in terms of tyrosine phosphorylation are easily quantified and an ECso for a given ligand is readily determined.

EXAMPLE 4

KIRA ELISA of the MPL/Rse Chimeric Receptor

The human MPL receptor has been disclosed by Vigon et al., *PNAS. USA* 89:5640–5644 (1992). A chimeric receptor comprising the ECD of the MPL receptor and the TM and ICD of Rse (Mark et al., supra) with a carboxyl-terminal flag polypeptide (i.e. Rse.gD; see Example 2) was subjected to the IRA ELISA described herein. The experimental procedure is outlined below. See also FIGS. 16 and 17.

(i) Capture Agent Preparation

Monoclonal anti-gD (clone 5B6) was produced against a peptide from Herpes simplex virus glycoprotein D (Paborsky et al., *Protein Engineering* 3(6):547–553 [1990]). The purified stock preparation was adjusted to 3.0 mg/ml in phosphate buffered saline (PBS), pH 7.4 and 1.0 ml aliquots were stored at −20° C.

(ii) Anti-phosphotyrosine Antibody Preparation

Monoclonal anti-phosphotyrosine, clone 4G10, was purchased from UBI (Lake Placid, N.Y.) and biotinylated using long-arm biotin-N-hydroxysuccinamide (Biotin-X-NHS, Research Organics, Cleveland, Ohio).

(iii) Ligand

The MPL ligand [de Sauvage et al., *Nature* 369: 533–538 (1994)] was prepared by recombinant techniques. The purified MPL ligand was stored at 4° C. as a stock solution.

(iv) Preparation of MPL/RsegD Nucleic Acid

The expression plasmid pSV.ID.Rse.gD produced as described in Example 2 above was modified to produce plasmid pSV.ID.M.tmRd6 which contained the coding sequences of the ECD of human MPL (amino acids 1–491) fused to the transmembrane domain and intracellular domain of Rse.gD (amino acids 429–911). Synthetic oligonucleotides were used to join the coding sequence of a portion of the extracellular domain of human MPL to a portion of the Rse coding sequence in a two step PCR cloning reaction as described by Mark et al. in *J. Biol. Chem.* 267: 26166–26171 (1992). Primers used for the first PCR reaction were M1(5'-TCTCGCTACCGTTTACAG—SEQ ID NO:12) and M2 (5'-CAGGTACCCACCAGGCGGTCTCGGT—SEQ ID NO: 13) with a MPL cDNA template and R1 (5'-GGGCCATGACACTGTCAA—SEQ ID NO: 14) and R2 (5'-GACCGCCACCGAGACCGCCTGGTGGGTACCTGTG GTCCTT—SEQ ID NO: 15) with a Rse cDNA template. The PvuII-SmaI portion of this fusion junction was used for the construction of the full-length chimeric receptor.

(v) Cell Transformation dp12. CHO cells (BP 307,247 published Mar. 15, 1989) were electroporated with pSV.ID.M.tmRd6 which had been linearized at a unique NotI site in the plasmid backbone. The DNA was ethanol precipitated after phenol/chloroform extraction and was resuspended in 20 µl 1/10 Tris EDTA. Then, 10 µg of DNA was incubated with $10^7$ CHO.dp12 cells in 1 ml of PBS on ice for 10 min. before electroporation at 400 volts and 330 µf. Cells were returned to ice for 10 min. before being plated into non-selective medium. After 24 hours cells were fed nucleoside-free medium to select for stable DHFR+clones.

(vi) Selection of Transformed Cells for Use in the KIRA ELISA

Clones expressing MPL/Rse.gD were identified by western-blotting of whole cell lysates post-fractionation by SDS-PAGE using the antibody 5B6 which detects the gD epitope tag.

(vii) Media

Cells were grown in F12/DMEM 50:50 (Gibco/BRL, Life Technologies, Grand Island, N.Y.). The media was supplemented with 10% diafiltered FBS (HyClone, Logan, Utah), 25 mM HEPES and 2 mM L-glutamine.

(viii) KIRA ELISA

MPL/Rse.gD transformed dp12. CHO cells were seeded ($3 \times 10^4$ per well) in the wells of a flat-bottom-96 well culture plate in 100 µl media and cultured overnight at 37° C. in 5% $CO_2$. The following morning the well supernatants were decanted, and the plates were lightly tamped on a paper towel. 50 µl of media containing either experimental samples or 200, 50, 12.5, 3.12, 0.78, 0.19, 0.048 or 0 ng/ml MPL ligand was then added to each well. The cells were stimulated at 37° C. for 30 min., the well supernatants were decanted, and the plates were once again lightly tamped on a paper towel. To lyse the cells and solubilize the chimeric receptors, 100 µl of lysis buffer was added to each well. Lysis buffer consisted of 150 mM NaCl containing 50 mM HEPES (Gibco), 0.5% Triton-X 100 (Gibco), 0.01% thimerosal, 30 KIU/ml aprotinin (ICN Biochemicals, Aurora, Ohio), 1 mM 4-(2-aminoethyl)-benzenesulfonyl fluoride hydrochloride (AEBSF; ICK Biochemicals), 50 μM leupeptin (ICN Biochemicals), and 2 mM sodium orthovanadate (Na$_3$VO$_4$; Sigma Chemical Co, St. Louis, Mo.), pH 7.5. The plate was then agitated gently on a plate shaker (Bellco Instruments, Vineland, N.J.) for 60 min. at room temperature.

While the cells were being solubilized, an ELISA microtiter plate (Nunc Maxisorp, Inter Med, Denmark) coated overnight at 4° C. with the 5B6 monoclonal anti-gD antibody (5.0 μg/ml in 50 mM carbonate buffers pH 9.6, 100 μl/well) was decanted, tamped on a paper towel and blocked with 150 μl/well of Block Buffer [PBS containing 0.5% BSA (Intergen Company, Purchase, N.Y.) and 0.01% thimerosal] for 60 min. at room temperature with gentle agitation. After 60 minutes, the anti-gD 5B6 coated plate was washed 6 times with wash buffer (PBS containing 0.05% Tween-20 and 0.01% himerosal) using an automated plate washer (ScanWasher 300, Skatron nstruments, Inc, Sterling, Va.).

The lysate containing solubilized MPL/Rse.gD from the cell-culture icrotiter well was transferred (85 μl/well) to anti-gD 5B6 coated and blocked ELISA well and was incubated for 2 h at room temperature with gentle agitation. The unbound MPL/Rse.gD was removed by washing with wash buffer and 100 μl of biotinylated 4G10 (anti-phosphotyrosine) diluted 1:18000 in dilution buffer (PBS containing 0.5% BSA, 0.05% Tween-20, 5 mM EDTA, and 0.01% thimerosal), i.e. 56 ng/ml was added to each well. After incubation for 2 h at room temperature the plate was washed and 100 μl of HRPO-conjugated streptavidin (Zymed Laboratories, S. San Francisco, Calif.) diluted 1:60000 in dilution buffer was added to each well. The plate was incubated for 30 minutes at room temperature with gentle agitation. The free avidin-conjugate was washed away and 100 μl freshly prepared substrate solution (tetramethyl benzidine [TMB]; 2-component substrate kit; Kirkegaard and Perry, Gaithersburg, Md.) was added to each well. The reaction was allowed to proceed for minutes, after which the color development was stopped by the addition of 100 μl/well 1.0 M H$_3$PO$_4$. The absorbance at 450 nm was read with a reference wavelength of 650 nm (ABS$_{450/650}$), using a vmax plate reader (Molecular Devices, Palo Alto, Calif.) controlled with a Macintosh Centris 650 (Apple Computers, Cupertino, Calif.) and DeltaSoft software (BioMetallics, Inc, Princeton, N.J.).

The results demonstrated that MPL ligand was able to activate the MPL/Rse.gD chimeric receptor in a concentration-dependent and ligand-specific manner.

What is claimed is:

1. A method for measuring phosphorylation of a kinase polypeptide comprising the steps of:
   (a) coating a first solid phase with a homogeneous population of eukaryotic cells so that the cells adhere to the first solid phase, wherein the cells comprise a kinase polypeptide.
   (b) exposing the adhering cells to an analyte;
   (c) solubilizing the adhering cells, thereby releasing cell lysate therefrom;
   (d) coating a second solid phase with a capture agent which binds specifically to the kinase polypeptide so that the capture agent adheres to the second solid phase;
   (e) exposing the adhering capture agent to the cell lysate obtained in step (c) so that the kinase polypeptide adheres to the second solid phase;
   (f) washing the second solid phase so as to remove unbound cell lysate;
   (g) exposing the adhering kinase polypeptide to an antibody which identifies phosphorylated residues in the kinase polypeptide; and
   (h) measuring binding of the antibody to the adhering kinase polypeptide, wherein the amount of antibody binding to the adhering kinase polypeptide is proportional to the amount of phosphorylation of said kinase polypeptide.

2. The method of claim 1, wherein the cells are transformed with nucleic acid encoding the kinase polypeptide prior to step (a).

3. The method of claim 1, wherein said kinase polypeptide is a tyrosine kinase polypeptide.

4. The method of claim 1, wherein said kinase polypeptide is a serine kinase polypeptide.

5. The method of claim 1, wherein said antibody identifies phosphorylated tyrosine residues in the kinase polypeptide.

6. The method of claim 1, wherein said antibody identifies phosphorylated serine residues in the kinase polypeptide.

7. The method of claim 1, wherein the analyte comprises a compound to activate the phosphorylation of the kinase polypeptide.

8. The method of claim 1, wherein the cells comprise a mammalian cell line.

9. The method of claim 1, wherein the cells are adherent.

10. The method of claim 1, wherein the capture agent comprises a capture antibody.

11. The method of claim 1, wherein the first solid phase comprises a well of a first assay plate.

12. The method of claim 11, wherein the first assay plate is a cell culture assay plate.

13. The method of claim 11, wherein between about $1 \times 10^4$ to $3 \times 10^5$ cells are added to the well in step (a).

14. The method of claim 1, wherein the second solid phase comprises a well of a second assay plate.

15. The method of claim 1, wherein the cell lysate is not concentrated or clarified prior to step (e).

16. The method of claim 11, wherein step (c) comprises adding a lysis buffer to the well of the first assay plate and gently agitating the first assay plate.

17. The method of claim 16, wherein the lysis buffer comprises a solubilizing detergent.

18. The method of claim 1, wherein said antibody is labeled.

19. The method of claim 18, wherein the label comprises an enzyme which is exposed to a color reagent and the color change of the color reagent is determined in (h).

20. The method of claim 1, wherein said kinase polypeptide is an intracellular kinase polypeptide.

21. The method of claim 1, wherein a block buffer is added to the second solid phase following step (d).

22. The method of claim 1, wherein said kinase polypeptide comprises a flag polypeptide.

23. The method of claim 22, wherein the flag polypeptide is fused to the carboxyl terminus of the kinase polypeptide.

* * * * *

UNITED STATES PATENT AND TRADEMARK OFFICE
CERTIFICATE OF CORRECTION

PATENT NO. : 6,287,784 B1
DATED : September 11, 2001
INVENTOR(S) : Godowski et al.

It is certified that error appears in the above-identified patent and that said Letters Patent is hereby corrected as shown below:

Column 2,
Line 53, delete "Knutson and Suck" and insert therefor -- Knutson and Buck --.

Column 6,
Line 29, delete "tranemembrane domain of Rae" and insert therefor
-- transmembrane domain of Rse --.
Line 51, delete "Roe.gD" and insert therefor -- Rse.gD --.

Column 7,
Line 16, delete "(total n+(3)" and insert therefor -- (total n =30) --.
Line 17, delete " sd ad" and insert therefor -- sd --.
Line 33, delete "anti-Roe " and insert therefor -- anti-Rse --.

Column 8,
Line 20, delete "KTIRA" and insert therefor -- KIRA --.
Line 65, delete "Ax1" and insert therefor -- Axl --
Line 67, delete "trka receptor, trkb receptor" and insert therefor -- trkA receptor, trkB receptor --.

Column 9,
Line 1, delete "trkc" and insert therefor -- trkC --.

Column 11,
Lines 48 and 55, delete "Rae" and insert therefor -- Rse --.

Column 12,
Line 42, delete "other" and insert therefor -- Other --.

Column 14,
Line 55, delete "*J.Mol. giol*" and insert therefor -- *J.Mol. Biol.* --.
Line 22, delete "[199]" and insert therefor -- [1991] --.

Column 16,
Line 12, delete "CDNA" and insert therefor -- cDNA --.
Line 28, delete rPTM" and insert therefor -- rPTK --.

Column 18,
Line 46, delete "tzpl " and insert therefor -- trp1 --.

Column 22,
Line 29, delete "REPES " and insert therefor -- HEPES --.

UNITED STATES PATENT AND TRADEMARK OFFICE
CERTIFICATE OF CORRECTION

PATENT NO. : 6,287,784 B1
DATED : September 11, 2001
INVENTOR(S) : Godowski et al.

It is certified that error appears in the above-identified patent and that said Letters Patent is hereby corrected as shown below:

Column 25,
Line 13, delete "70-9of" and insert therefor -- 70-90% --.

Column 27,
Line 8, delete "BLISA" and insert therefor -- ELISA --.

Column 31,
Line 6, delete "(nyatech)" and insert therefor -- (Dynatech) --.

Column 35,
Line 31, delete "Anti-phosphotvrosine" and insert therefor -- Anti-phosphotyrosine --.

Column 36,
Line 61, delete "HRG$\theta$1 1$_{117-244}$" and insert therefor -- HRG$\beta$1$_{117-244}$ --.

Column 38,
Line 38, delete "Licand" and insert therefore -- Ligand --.
Line 47, delete "Rae" and insert therefor -- Rse --.
Line 60, delete "Bio.TechniAues" and insert therefor -- Bio.Techniques, --.

Column 40,
Lines 54, delete "Rae" and insert therefor -- Rse --.

Column 41,
Line 9, delete "KEPES" and insert therefor -- HEPES --.

Column 42,
Line 34, delete "trkb" and insert therfor -- trkB --.

Column 43,
Line 64, delete "trka" and insert therefor -- trkA --.
Line 65, delete "trkb" and insert therefor -- trkB --.
Line 65, delete "trkc" and insert therefor -- trkC --.

Column 44,
Line 45, delete "$^{100}$ µl" and insert therefor -- 100 µl --.

Column 45,
Line 46, delete "ECso" and insert therefor -- EC$_{50}$ --.

UNITED STATES PATENT AND TRADEMARK OFFICE
CERTIFICATE OF CORRECTION

PATENT NO. : 6,287,784 B1
DATED : September 11, 2001
INVENTOR(S) : Godowski et al.

It is certified that error appears in the above-identified patent and that said Letters Patent is hereby corrected as shown below:

Column 46,
Line 7, delete "MPL/RsegD" and insert therefor -- MPL/Rse.gD --.

Column 47,
Line 17, delete "himerosal" and insert therefor -- Thimerosal --.
Line 18, delete "nstruments" and insert therefor -- instruments --.
Line 20, delete "icrotiter" and insert therefor -- microtiter --.

Signed and Sealed this

Twelfth Day of March, 2002

*Attest:*

JAMES E. ROGAN
*Attesting Officer*  *Director of the United States Patent and Trademark Office*